(12) United States Patent
Furuya et al.

(10) Patent No.: US 6,413,972 B1
(45) Date of Patent: Jul. 2, 2002

(54) NITROGEN-CONTAINING HETEROCYCLIC COMPOUNDS, THEIR PRODUCTION AND USE

(75) Inventors: Shuichi Furuya; Toshihiro Imaeda, both of Tsukuba; Satoshi Sasaki, Ushiku, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/711,139

(22) Filed: Nov. 14, 2000

Related U.S. Application Data

(62) Division of application No. 09/147,616, filed as application No. PCT/JP98/05841 on Dec. 24, 1998, now Pat. No. 6,194,419.

(30) Foreign Application Priority Data

Dec. 26, 1997 (JP) .............................. 9-358998
Mar. 5, 1998 (JP) ........................... 10-054022

(51) Int. Cl.⁷ .................. C07D 487/04; A61K 31/519; A61P 5/02; A61P 15/18
(52) U.S. Cl. ....................... 514/258; 544/281
(58) Field of Search ........................ 544/281; 514/258

(56) References Cited

U.S. PATENT DOCUMENTS 5,208,141 A * 5/1993 Ikesu et al. .................. 430/558

FOREIGN PATENT DOCUMENTS

| EP | 166609 | 1/1986 |
|---|---|---|
| EP | 163240 | 12/1989 |
| WO | 95/28405 | 10/1995 |
| WO | 97 14682 | 4/1997 |
| WO | 97 14697 | 4/1997 |
| ZA | 8 609 289 | 12/1986 |

OTHER PUBLICATIONS

Abdalla et al., J. Heterocyclic Chemistry 24, 297–301, 1987.
R.J. Bienstock et al., "Conformational Analysis of a highly potent dicyclic gonadotropin releasing hormone Antagonist . . . dynamics", J. Med. Chem., vol. 36:22, pp. 3265–3273, 1993, XP–002101034.

L. Pecori Vettori et al., "Synthesis fo some 7–phenylpyrrolo [1,2–a] pyrimidine derivatives", 11 Farmaco, Ed. Sci. vol. 42:11, pp. 787–792, 1987, XP–002101035.

T. Pyl et al., "Elektrophile substitutionen an 7–meth–2–phenyl–imidazo[1.2–a]pyrimidinen", Justus Liebigs Annalen Der Chemie, Voll. 669, pp. 112–126, 1996, XP–002101036.

P. Vettori et al., Preparation and formulation of pyrrolo[1, 2–a]–pyrimidines as antiinflammatory, antipyretic, And analgesic agents, Chem. Absts. No. 110450y, 1998, XP–002101037.

* cited by examiner

Primary Examiner—Richard L. Raymond
Assistant Examiner—Venkataraman Balasubramanian
(74) Attorney, Agent, or Firm—Foley & Lardner

(57) ABSTRACT

A compound of the formula:

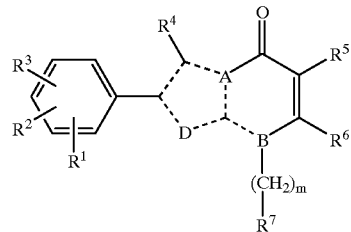

wherein one of A and D is N and the other is C, or both are N; B is N or C; m is 0–3; $R^1$, $R^2$ and $R^3$ each is (i) H or (ii) a group bound via C, N, O or S; $R^4$ is a group bound via C; $R^5$ is H or a group bound via C or O; $R^6$ is H or a group bound via C; $R^7$ is a homo- or hetero-cyclic group which may be substituted; or a salt thereof possesses excellent gonadotropin-releasing hormone antagonizing activity, and is useful as a prophylactic or therapeutic agent for sex hormone-dependent diseases, and so forth.

31 Claims, No Drawings

NITROGEN-CONTAINING HETEROCYCLIC COMPOUNDS, THEIR PRODUCTION AND USE

This is a divisional application of U.S. application Ser. No. 09/147,616, filed Feb. 2, 1999 which is now U.S. Pat. No. 6,194,419 and which is a §371 application of PCT/JP98/05841 filed Dec. 24, 1998.

TECHNICAL FIELD

The present invention relates to nitrogen-containing heterocyclic compounds exhibiting gonadotropin releasing hormone (GnRH) antagonizing activity, their production and pharmaceutical compositions containing them.

BACKGROUND ART

The secretion of hypophysial anterior lobe hormone is regulated by the peripheral hormone secreted by each target organ and the secretion-promoting or secretion-suppressing hormone secreted by the hypothalamus, which is the center superior to the hypophysial anterior lobe, and this group of hormones hereinafter generically referred to as hypothalamic hormone in this specification. To date, nine hypothalamic hormones have been identified, for example, thyroid-stimulating hormone-releasing hormone (TRH), and gonadotropin releasing hormone [GnRH, also known as luteinizing hormone releasing hormone (LH-RH)], etc. It is conjectured that these hypothalamic hormones exhibit their hormone actions etc. via receptors assumed to be present in the hypophysial anterior lobe, and analyses of receptor genes specific to these hormones, including humans, are ongoing. Antagonists or agonists that act specifically and selectively on these receptors would therefore regulate the action of hypothalamic hormones and hence regulate the secretion of hypophysial anterior lobe hormone. As a result, such antagonists or agonists are expected to prevent or treat diseases depending on these hypophysial anterior lobe hormone.

Known compounds possessing GnRH-antagonizing activity include GnRH-derived linear peptides (U.S. Pat. Nos. 5,140,009 and 5,171,835), a cyclic hexapeptide derivative (JP-A-61-191698), a bicyclic peptide derivative [Journal of Medicinal Chemistry, Vol. 36, pp. 3265–3273 (1993)), and so forth. Non-peptide compounds possessing GnRH-antagonizing activity include compounds described in WO 95/28405, WO 97/14697 and WO 97/14682, etc.

ZA 86/9289 describes 1,4-dihydro-1-ethyl-7-phenylpyrrolo[1,2-a]pyrimidin-4-one in Example 22.

Peptide compounds pose a large number of problems to be resolved with respect to oral absorbability, dosage form, dose volume, drug stability, sustained action, metabolic stability etc. There is strong demand for an oral GnRH antagonist, especially one based on a non-peptide compound, that has excellent therapeutic effect on hormone-dependent cancers, e.g., prostatic cancer, endometriosis, precocious puberty etc., and that does not show transient hypophysial-gonadotropic action (acute action).

DISCLOSURE OF INVENTION

The present inventors produced various nitrogen-containing heterocyclic derivatives, investigated their actions, and found that some nitrogen-containing heterocyclic compounds possess excellent GnRH-antagonizing activity. The inventors conducted further investigation based on this finding, and developed the present invention. Accordingly, the present invention relates to:

[1] A compound of the formula (I):

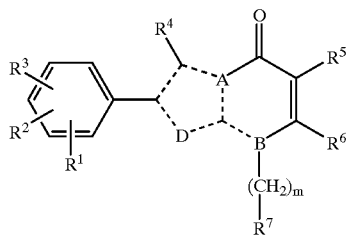

wherein
one of A and D represents a nitrogen atom and the other represents a carbon atom, or both represent a nitrogen atom;
B represents a nitrogen atom or a carbon atom; m represents an integer from 0 to 3;
$R^1$, $R^2$ and $R^3$ each represents (i) hydrogen or (ii) a group bound via a carbon atom, a nitrogen atom, an oxygen atom or a sulfur atom;
$R^4$ represents a group bound via a carbon atom;
$R^5$ represents (i) hydrogen, (ii) halogen or (iii) a group bound via a carbon atom or an oxygen atom;
$R^6$ represents hydrogen or a group bound via a carbon atom;
$R^7$ represents a homocyclic group which may be substituted or a heterocyclic group which may be substituted; and each dotted line represents a single bond or a double bond, [hereinafter sometimes referred to briefly as compound (I)] or a salt thereof;

[2] a compound of the above [1] or a salt thereof, wherein $R^1$, $R^2$ and $R^3$ each is
(1) hydrogen,
(2) a hydrocarbon group which may be substituted,
(3) an acyl group which may be substituted,
(4) a heterocyclic group having a bond in a carbon atom thereof which may be substituted,
(5) a group of the formula: —COOR$^{21}$ wherein R$^{21}$ is hydrogen, a hydrocarbon group which may be substituted or a heterocyclic group which may be substituted,
(6) a group of the formula: —CO—NR$^{15}$R$^{16}$ wherein R$^{15}$ is hydrogen, a hydrocarbon group which may be substituted or a $C_{1-10}$ alkoxy group; and R$^{16}$ is hydrogen or a hydrocarbon group which may be substituted; or R$^{15}$ and R$^{16}$ form, taken together with the adjacent nitrogen atom, a cyclic amino group which may be substituted,
(7) a cyano group,
(8) a nitro group,
(9) a group of the formula: —NR$^8$R$^9$ wherein R$^8$ is (i) hydrogen, (ii) a hydrocarbon group which may be substituted, (iii) an acyl group which may be substituted, (iv) a group of the formula: —O—R$^{13}$ wherein R$^{13}$ is hydrogen, a $C_{1-10}$ hydrocarbon group which may be substituted, a $C_{1-20}$ acyl group which may be substituted, a $C_{1-20}$ alkylsulfonyl group which may be substituted, a $C_{6-14}$ arylsulfonyl group which may be substituted or a heterocyclic group which may be substituted, (v) a heterocyclic group which may be substituted or (vi) a group of the formula: —S(O)t-R$^{12}$ wherein t is an integer from 0 to 2, and R$^{12}$ is hydrogen or a $C_{1-10}$ hydrocarbon group which may be substituted;
R$^9$ is hydrogen, a hydrocarbon group which may be substituted or an acyl group which may be substituted; or R⁸ and R⁹ form, taken together with the adjacent nitrogen atom, a cyclic amino group which may be substituted,
(10) a group of the formula: —O—R¹³ wherein R¹³ is as defined above, or
(11) a group of the formula: —S(O)t-R¹⁴ wherein t is an integer from 0 to 2, and R¹⁴ is hydrogen, a hydrocarbon group which may be substituted or a heterocyclic group which may be substituted;

R⁴ is
(1) a hydrocarbon group which may be substituted,
(2) an acyl group which may be substituted,
(3) a heterocyclic group having a bond in a carbon atom thereof which may be substituted,
(4) a group of the formula: —COOR²¹ wherein R²¹ is as defined above,
(5) a group of the formula: —CO—NR¹⁵R¹⁶ wherein each symbol is as defined above, or
(6) a cyano group;

R⁵ is
(1) hydrogen,
(2) halogen,
(3) a hydrocarbon group which may be substituted,
(4) an acyl group which may be substituted,
(5) a heterocyclic group having a bond in a carbon atom thereof which may be substituted,
(6) a group of the formula: —COOR²¹ wherein R²¹ is as defined above,
(7) a group of the formula: —CO—NR¹⁵R¹⁶ wherein each symbol is as defined above,
(8) a cyano group, or
(9) a group of the formula: —O—R¹³ wherein R¹³ is as defined above;

R⁶ is
(1) hydrogen,
(2) a hydrocarbon group which may be substituted,
(3) an acyl group which may be substituted,
(4) a heterocyclic group having a bond in a carbon atom thereof which may be substituted,
(5) a group of the formula: —COOR²¹ wherein R²¹ is as defined above,
(6) a group of the formula: —CO—NR⁵R¹⁶ wherein each symbol is as defined above, or
(7) a cyano group;

R⁷ is
(i) a $C_{6-10}$ aryl or $C_{3-7}$ cycloalkyl group, each of which may be substituted by 1 to 6 substituents selected from the group consisting of (1) $C_{1-15}$ alkyl which may be substituted by 1 to 3 halogen, (2) $C_{3-10}$ cycloalkyl, (3) $C_{2-10}$ alkenyl, (4) $C_{2-10}$ alkynyl, (5) $C_{3-10}$ cycloalkenyl, (6) $C_{6-10}$ aryl, (7) $C_{7-20}$ aralkyl, (8) nitro, (9) hydroxy, (10) mercapto, (11) oxo, (12) thioxo, (13) cyano, (14) carbamoyl, (15) carboxyl, (16) $C_{1-6}$ alkoxy-carbonyl, (17) sulfo, (18) halogen, (19) $C_{1-6}$ alkoxy, (20) $C_{6-10}$ aryloxy, (21) $C_{1-6}$ alkanoyloxy, (22) $C_{1-6}$ alkylthio, (23) $C_{6-10}$ arylthio, (24) $C_{1-6}$ alkylsulfinyl, (25) $C_{6-10}$ arylsulfinyl, (26) $C_{1-6}$ alkylsulfonyl, (27) $C_{6-10}$ arylsulfonyl, (28) amino, (29) $C_{1-6}$ alkanoylamino, (30) mono- or di- $C_{1-4}$ alkylamino, (31) $C_{3-8}$ cycloalkylamino, (32) $C_{6-10}$ arylamino, (33) $C_{1-6}$ alkanoyl, (34) $C_{6-10}$ aryl-carbonyl and (35) 5- to 6-membered heterocyclic group, or
(ii) a heterocyclic group which may be substituted, in which "hydrocarbon group" is a $C_{1-20}$ hydrocarbon group selected from $C_{1-15}$ alkyl, $C_{3-10}$ cycloalkyl, $C_{2-10}$ alkenyl, $C_{2-10}$ alkynyl, $C_{3-10}$ cycloalkenyl, $C_{6-14}$ aryl and $C_{7-20}$ aralkyl;

"$C_{1-10}$ hydrocarbon group" is a $C_{1-10}$ alkyl, $C_{3-10}$ cycloalkyl, $C_{2-10}$ alkenyl, $C_{2-10}$ alkynyl, $C_{3-10}$ cycloalkenyl, $C_{6-10}$ aryl or phenyl-$C_{1-4}$ alkyl group;

"acyl group" and "$C_{1-20}$ acyl group" each is formyl, $C_{1-6}$ alkyl-carbonyl, $C_{1-6}$ alkoxy-carbonyl, $C_{6-14}$ aryl-carbonyl, $C_{6-14}$ aryloxy-carbonyl, $C_{6-14}$ aryl-$C_{1-6}$ alkyl-carbonyl, $C_{6-14}$ aryl-$C_{1-6}$ alkoxy-carbonyl, $C_{2-4}$ alkenyl-carbonyl, $C_{3-6}$ cycloalkyl-carbonyl or tricyclic bridged $C_{9-10}$ hydrocarbon-carbonyl;

"heterocyclic group" is (1) a 5- to 8-membered heterocyclic group containing 1 to 4 hetero atoms selected from oxygen atoms, sulfur atoms, nitrogen atoms in addition to carbon atoms, (2) a bi- or tri-cyclic condensed heterocyclic group resulting from condensation of 2 or 3 of the above (1) heterocyclic group, whether identical or not, or (3) a bi- or tri-cyclic condensed heterocyclic group resulting from condensation of the above (1) heterocyclic group and 1 or 2 benzene rings;

"cyclic amino group" is a 5- to 7-membered cyclic amino group optionally containing 1 to 3 hetero atoms selected from oxygen atoms, sulfur atoms, nitrogen atoms in addition to carbon atoms and a nitrogen atom;

"substituent(s)" for the "hydrocarbon group which may be substituted", the "$C_{1-10}$ hydrocarbon group which may be substituted", the "acyl group which may be substituted", "$C_{1-20}$ acyl group which may be substituted", the "$C_{1-20}$ alkylsulfonyl group which may be substituted" or the "$C_{6-14}$ arylsulfonyl group which may be substituted" is selected from 1 to 6 of (1) halogen, (2) nitro, (3) nitroso, (4) cyano, (5)(i) $C_{1-6}$ alkyl which may be substituted by 1 to 3 substituents selected from the group consisting of hydroxy, $C_{1-6}$ alkoxy, $C_{13}$ alkoxy-$C_{1-3}$ alkoxy, $C_{1-3}$ alkylthio, hydroxy-$C_{1-3}$ alkoxy, $C_{1-6}$ alkyl-carbonyl, carboxy, carbamoyl, $C_{1-6}$ alkyl-carbamoyl, 5- to 8-membered heterocyclic group and halogen, (ii) $C_{1-4}$ alkanoyl or $C_{2-4}$ alkenoyl, (iii) $C_{6-14}$ aryl-$C_{1-6}$ alkyl which may be substituted by 1 to 3 substituents selected from the group consisting of halogen, $C_{1-3}$ alkoxy and $C_{1-4}$ alkyl, (iv) $C_{6-14}$ aryl which may be substituted by 1 to 3 halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkyl amino, (ix) $C_{2-6}$ alkenyl amino, (x) $C_{1-3}$ alkoxy-carbonyl, (xi) formyl or $C_{1-6}$ alkyl-carbonyl, or (xii) hydroxy which may be substituted by $C_{3-6}$ cycloalkyloxy-carbonyl, (6) a group of the formula: —S(O)t-R¹⁷ wherein t is an integer from 0 to 2, and R¹⁷ is (i) hydrogen or (ii) a $C_{1-6}$ alkyl, $C_{6-14}$ aryl or $C_{7-20}$ aralkyl group which may be substituted by 1 to 3 substituents selected from the group consisting of halogen, nitro, cyano, hydroxy, oxo, thioxo, carboxy, cyano-$C_{6-14}$ aryl and halogeno-$C_{6-14}$ aryl, (7) a group of the formula: —NR¹⁸R¹⁹ wherein R¹⁸ and R¹⁹ each is hydrogen, $C_{1-6}$ alkyl, $C_{1-6}$ alkylamino-$C_{1-6}$ alkyl, $C_{1-6}$ alkoxy, $C_{2-6}$ alkenyl, $C_{3-7}$ cycloalkyl, phenyl, phenyl-$C_{1-6}$ alkyl, $C_{1-6}$ alkanoyl, $C_{3-6}$ alkenoyl, $C_{4-7}$ cycloalkyl-carbonyl, phenyl-$C_{1-6}$ alkyl-carbonyl, $C_{1-6}$ alkoxy-carbonyl, phenyl-$C_{1-6}$ alkoxy-carbonyl or 5- to 8-membered heterocyclic group, (8) a group of the formula: —CO—$R^{20}$ wherein $R^{20}$ is (i) hydrogen, (ii) hydroxy, (iii) $C_{1-10}$ alkyl or (iv) $C_{1-6}$ alkoxy which may be substituted by $C_{6-14}$ aryl which may be substituted by 1 to 3 substituents selected from the group consisting of halogen and nitro, (v) $C_{3-6}$ cycloalkyl, (vi) $C_{6-14}$ aryl, (vii) $C_{6-14}$ aryloxy, (viii) $C_{7-20}$ aralkyl, (ix) a group of the formula: —$NR^{10}R^{11}$ wherein $R^{10}$ is hydrogen, a $C_{1-10}$ hydrocarbon group which may be substituted, a $C_{1-20}$ acyl group which may be substituted, a group of the formula: —O—$R^{13}$ wherein $R^{13}$ is as defined above, a heterocyclic group which may be substituted or a group of the formula: —S(O)t-$R^{12}$ wherein each symbol is as defined above; and $R^{11}$ is hydrogen or a $C_{1-10}$ hydrocarbon group; or $R^{10}$ and $R^{11}$ form, taken together with the adjacent nitrogen atom, a cyclic amino group which may be substituted, or (x) 5- to 8-membered heterocyclic group, (9) 5- to 8-membered heterocyclic group which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (10) sulfo, (11) $C_{6-14}$ aryl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (12) $C_{3-7}$ cycloalkyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (13) $C_{1-6}$ alkylenedioxy, (14) oxo, (15) thioxo, (16) $C_{2-4}$ alkynyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (17) $C_{3-10}$ cycloalkyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (18) $C_{2-10}$ alkenyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (19) $C_{7-20}$ aralkyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (20) amidino and (21) azido;

"substituent(s)" for the "heterocyclic group which may be substituted" or the "heterocyclic group having a bond in a carbon atom thereof which may be substituted" is selected from 1 to 6 of (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{6-10}$ aryl-$C_{1-5}$ alkyl, (7) $C_{6-14}$ aryl, (8) $C_{1-6}$ alkoxy, (9) $C_{6-14}$ aryloxy, (10) $C_{1-6}$ alkanoyl, (11) $C_{6-14}$ aryl-carbonyl, (12) $C_{1-6}$ alkanoyloxy, (13) $C_{6-14}$ aryl-carbonyloxy, (14) carboxyl, (15) $C_{1-6}$ alkoxy-carbonyl, (16) carbamoyl, (17) N-mono-$C_{1-4}$ alkylcarbamoyl, (18) N,N-di-$C_{1-4}$ alkylcarbamoyl, (19) 3- to 6-membered cyclic aminocarbonyl, (20) halogen, (21) mono-, di- or tri-halogeno-$C_{1-4}$ alkyl, (22) oxo, (23) amidino, (24) imino, (25) amino, (26) mono- or di-$C_{1-4}$ alkylamino, (27) 3- to 6-membered cyclic amino, (28) $C_{1-6}$ alkanoylamino, (29) benzamido, (30) carbamoylamino, (31) N-$C_{1-4}$ alkylcarbamoylamino, (32) N,N-di-$C_{1-4}$ alkylcarbamoylamino, (33) $C_{1-3}$ alkylenedioxy, (34) —$B(OH)_2$, (35) hydroxy, (36) epoxy, (37) nitro, (38) cyano, (39) mercapto, (40) sulfo, (41) sulfino, (42) phosphono, (43) sulfamoyl, (44) $C_{1-6}$ alkylsulfamoyl, (45) di-$C_{1-6}$ alkylsulfamoyl, (46) $C_{1-6}$ alkylthio, (47) phenylthio, (48) $C_{1-6}$ alkylsulfinyl, (49) phenylsulfinyl, (50) $C_{1-6}$ alkylsulfonyl and (51) phenylsulfonyl; and "substituent(s)" for the "cyclic amino group which may be substituted" is selected from 1 to 3 of $C_{1-6}$ alkyl, $C_{6-14}$ aryl, phenyl-$C_{1-4}$ alkyl, benzhydryl, $C_{16}$ alkyl-carbonyl, $C_{6-14}$ aryl-carbonyl and $C_{1-6}$ alkoxy-carbonyl;

[3] a compound of the above [1] or a salt thereof, wherein A is a nitrogen atom;

[4] a compound of the above [1] or a salt thereof, wherein B is a nitrogen atom;

[5] a compound of the above [1] or a salt thereof, wherein D is a nitrogen atom;

[6] a compound of the above [1] or a salt thereof, wherein m is 1;

[7] a compound of the above [1] or a salt thereof, wherein $R^1$ is (1) a $C_{1-15}$ alkyl group which may be substituted, (2) a $C_{3-10}$ cycloalkyl group which may be substituted, (3) a $C_{2-10}$ alkenyl group which may be substituted, (4) a $C_{2-10}$ alkynyl group which may be substituted, (5) a $C_{3-10}$ cycloalkenyl group which may be substituted, (6) a $C_{6-14}$ aryl group which may be substituted, (7) a $C_{7-20}$ aralkyl group which may be substituted, (8) a $C_{1-20}$ acyl group which may be substituted, (9) a nitro group, (10) a group of the formula: —$NR^{10}R^{11}$ wherein $R^{10}$ is hydrogen, a $C_{1-10}$ hydrocarbon group which may be substituted, a $C_{1-20}$ acyl group which may be substituted, a hydroxy group which may be substituted, a heterocyclic group which may be substituted or a group of the formula: —S(O)t-$R^{12}$ wherein t is an integer from 0 to 2, and $R^{12}$ is hydrogen or a $C_{1-10}$ hydrocarbon group which may be substituted; $R^{11}$ is hydrogen or a $C_{1-10}$ hydrocarbon group; or $R^{10}$ and $R^{11}$ form, taken together with the adjacent nitrogen atom, a cyclic amino group which may be substituted, or (11) a group of the formula: —O—$R^{13}$ wherein $R^{13}$ is hydrogen, a $C_{1-10}$ hydrocarbon group which may be substituted, a $C_{1-20}$ acyl group which may be substituted, a $C_{1-20}$ arylsulfonyl group which may be substituted, a $C_{6-14}$ arylsulfonyl group which may be substituted, or a heterocyclic group which may be substituted; and $R^2$ and $R^3$ each is hydrogen;

[8] a compound of the above [1] or a salt thereof, wherein $R^2$ and $R^3$ each is hydrogen;

[9] a compound of the above [8] or a salt thereof, wherein the position of $R^1$ is para-position;

[10] a compound of the above [1] or a salt thereof, wherein $R^1$ is (1) an amino group which may be substituted by (i) carbamoyl which may be substituted by $C_{1-6}$ alkyl or $C_{1-6}$ alkoxy, or (ii) $C_{1-6}$ alkyl-carbonyl, or (2) a $C_{1-6}$ alkoxy group which may be substituted by $C_{3-6}$ cycloalkyl;

[11] a compound of the above [1] or a salt thereof, wherein $R^4$ is a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted or a $C_{7-20}$ aralkyl group which may be substituted;

[12] a compound of the above [1] or a salt thereof, wherein $R^4$ is a $C_{1-6}$ alkyl group which may be substituted;

[13] a compound of the above [1] or a salt thereof, wherein $R^4$ is a $C_{1-6}$ alkyl group which may be substituted by halogen, hydroxy which may be substituted or amino which may be substituted;

[14] a compound of the above [1] or a salt thereof, wherein $R^4$ is a group of the formula: —$(CH_2)n$-$NR^{10}R^{11}$ wherein n is an integer from 1 to 3; $R^{10}$ is hydrogen, a $C_{1-10}$ hydrocarbon group which may be substituted, a $C_{1-20}$ acyl group which may be substituted, a hydroxy group which may be substituted, a heterocyclic group which may be substituted, or a group of the formula: —$S(O)t$-$R^{12}$ wherein t is an integer from 0 to 2, and $R^{12}$ is hydrogen or a $C_{1-10}$ hydrocarbon group which may be substituted; and $R^{11}$ is hydrogen or a $C_{1-10}$ hydrocarbon group; or $R^{10}$ and $R^{11}$ form, taken together with the adjacent nitrogen atom, a cyclic amino group which may be substituted;

[15] a compound of the above [1] or a salt thereof, wherein $R^4$ is a N—$C_{1-6}$ alkyl-N-benzylaminomethyl group;

[16] a compound of the above [1] or a salt thereof, wherein $R^5$ is hydrogen, halogen, a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted, a $C_{7-20}$ aralkyl group which may be substituted, a $C_{1-20}$ acyl group which may be substituted, a carboxy group which may be esterified or amidated, or a group of the formula: —O—$R^{13}$ wherein $R^{13}$ is hydrogen or a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted, a $C_{7-20}$ aralkyl group which may be substituted, a $C_{1-20}$ acyl group which may be substituted, a $C_{1-20}$ alkylsulfonyl group which may be substituted, a $C_{6-14}$ arylsulfonyl group which may be substituted or a heterocyclic group which may be substituted;

[17] a compound of the above [1] or a salt thereof, wherein $R^5$ is (1) a $C_{1-6}$ alkoxy-carbonyl group, (2) a $C_{6-10}$ aryl group which may be substituted by halogen or $C_{1-6}$ alkoxy, or (3) a phenyl-$C_{1-3}$ alkyl group;

[18] a compound of the above [1] or a salt thereof, wherein $R^6$ is hydrogen, a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted or a $C_{7-20}$ aralkyl group which may be substituted;

[19] a compound of the above [13] or a salt thereof, wherein $R^6$ is hydrogen or a $C_{1-6}$ alkyl group;

[20] a compound of the above [1] or a salt thereof, wherein $R^7$ is a $C_{6-14}$ aryl group which may be substituted;

[21] a compound of the above [1] or a salt thereof, wherein $R^7$ is a phenyl group which may be substituted by halogen(s);

[22] a compound of the above [1] or a salt thereof, wherein one of A and D represents a nitrogen atom and the other represents a carbon atom, or both represent a nitrogen atom; B represents a nitrogen atom or a carbon atom; m represents an integer from 0 to 3; $R^1$, $R^2$ and $R^3$ each represents (i) hydrogen or (ii) a group bound via a carbon atom, a nitrogen atom, an oxygen atom or a sulfur atom; $R^4$ represents a group bound via a carbon atom; $R^5$ represents hydrogen or a group bound via a carbon atom or an oxygen atom; $R^6$ represents hydrogen or a group bound via a carbon atom; $R^7$ represents a homocyclic group which may be substituted or a heterocyclic group which may be substituted; and each dotted line represents a single bond or a double bond;

[23] a compound of the above [1], which is represented by the formula (e):

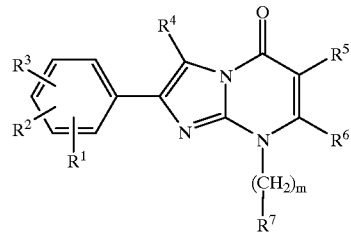

wherein each symbol is as defined above, or a salt thereof;

[24] a compound of the above [23] or a salt thereof, wherein $R^4$ is a group of the formula: —$(CH_2)n$-$NR^{10}R^{11}$ wherein n is an integer from 1 to 3; $R^{10}$ is hydrogen, a $C_{1-10}$ hydrocarbon group which may be substituted, a $C_{1-20}$ acyl group which may be substituted, a hydroxy group which may be substituted, a heterocyclic group which may be substituted, or a group of the formula: —$S(O)t$-$R^{12}$ wherein t is an integer from 0 to 2, and $R^{12}$ is hydrogen or a $C_{1-10}$ hydrocarbon group which may be substituted; and $R^{11}$ is hydrogen, a $C_{1-10}$ hydrocarbon group or a $C_{1-20}$ acyl group which may be substituted; or $R^{10}$ and $R^{11}$ form, taken together with the adjacent nitrogen atom, a cyclic amino group which may be substituted;

[25] a compound of the above [1], which is represented by the formula:

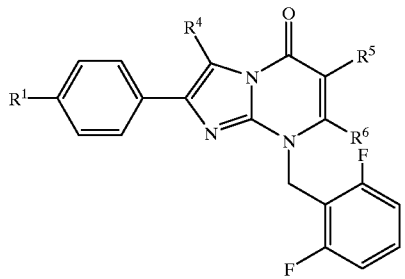

wherein each symbol is as defined above, or a salt thereof;

[26] a compound of the above [25] or a salt thereof, wherein
$R^1$ is (1) an amino group which may be substituted by (i) carbamoyl which may be substituted by $C_{1-6}$ allyl or $C_{1-6}$ alkoxy, or (ii) $C_{1-6}$ alkyl-carbonyl, or (2) a $C_{1-6}$ alkoxy group which may be substituted by $C_{3-6}$ cycloalkyl;
$R^4$ is a N—$C_{1-6}$ alkyl-N-benzylaminomethyl group
$R^5$ is (1) a $C_{1-6}$ alkoxy-carbonyl group, (2) a $C_{6-10}$ aryl group which may be substituted by halogen or $C_{1-6}$ alkoxy, or (3) a phenyl-$C_{1-3}$ allyl group; and
$R^6$ is hydrogen;

[27] a compound of the above [25] or a salt thereof, wherein $R^1$ is
(1) a nitro group,
(2) an amino group which may be substituted by 1 or 2 substituents selected from the group consisting of (i) $C_{1-6}$ alkyl which may be substituted by hydroxy, (ii) $C_{1-6}$ alkyl-carbonyl which may be substituted by hydroxy, halogen or thienyl, (iii) $C_{6-10}$ aryl-carbonyl which may be substituted by $C_{1-6}$ alkyl, $C_{1-6}$ alkoxy or halogen, (iv) $C_{3-6}$ cycloalkyl-carbonyl, (v) $C_{2-4}$ alkenyl-carbonyl, (vi) $C_{1-6}$ alkoxy-carbonyl, (vii) $C_{1-6}$ alkylamino-carbonyl, (viii) $C_{1-6}$ alkoxyamino-carbonyl, (ix) phenylaminocarbonyl, (x) an isoxazolylcarbonyl, thienylcarbonyl, thiazolylcarbonyl, pyrazolylcarbonyl or furylcarbonyl group which may be substituted by 1 or 2 substituents selected from the group consisting of $C_{1-6}$ alkyl, nitro and $C_{1-6}$ alkoxy, (xi) pyridylcarbonyl, (xii) $C_{1-6}$ alkylsulfonyl, (xiii) thienylsulfonyl and (xiv) phenylsulfonyl which may be substituted by $C_{1-6}$ alkyl,
(3) a pyrrolyl group or
(4) a hydroxy group which may be substituted by $C_{1-6}$ alkyl, $C_{3-6}$ cycloalkyl-$C_{1-3}$ alkyl or $C_{1-6}$ alkyl-carbonyl:
$R^4$ is a $C_{1-6}$ alkyl group which may be substituted by 1 or 2 substituents selected from the group consisting of (1) halogen. (2) hydroxy and (3) amino which may be substituted by 1 or 2 substituents selected from the group consisting of $C_{1-6}$ alkyl, phenyl-$C_{1-3}$ alkyl and di-$C_{1-6}$ alkylamino-$C_{1-3}$ alkyl;
$R^5$ is (1) halogen, (2) a phenyl group which may be substituted by halogen or $C_{1-6}$ alkyl, or (3) a carbonyl group substituted by (i) $C_{1-6}$ alkyl, (ii) amino substituted by $C_{1-6}$ alkyl and $C_{1-6}$ alkoxy or (iii) $C_{1-6}$ alkoxy; and
$R^6$ is hydrogen or a $C_{1-3}$ alkyl group;

[28] 8-(2,6-difluorobenzyl)-5,8-dihydro-2-[4-(ethylaminocarbonylamino)phenyl]-3-(N-methyl-N-benzylaminomethyl)-5-oxoimidazo[1,2-a]pyrimidine-6-carboxylic acid ethyl ester, 8-(2,6-difluorobenzyl)-5,8-dihydro-2-[4-(methoxyaminocarbonylamino)phenyl]-3-(N-methyl-N-benzylaminomethyl)-5-oxoimidazo[1,2-a]pyrimidine-6-carboxylic acid isopropyl ester, 8-(2,6-difluorobenzyl)-5,8-dihydro-2-[4-(ethylaminocarbonylamino)phenyl]-3-(N-methyl-N-benzylaminomethyl)-5-oxoimidazo[1, 2-a]pyrimidine-6-carboxylic acid isopropyl ester, or salts thereof;

[29] a process for producing a compound of the above [23] or a salt thereof, which comprises reacting a compound of the formula (iv):

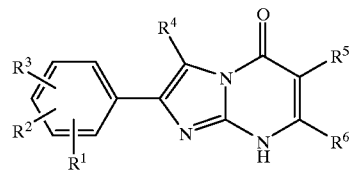

wherein each symbol is as defined above, or a salt thereof, with a compound of the formula: $X^2$—$(CH_2)m$-$R^7$ wherein $X^2$ is a leaving group; and the other symbols are as defined above, or a salt thereof;

[30] a pharmaceutical composition which comprises a compound of the above [1] or a salt thereof;

[31] a composition of the above (30) which is a gonadotropin-releasing hormone antagonist;

[32] a composition of the above [30] for preventing and/or treating a sex hormone dependent disease;

[33] a composition of the above [30] for preventing and/or treating a sex hormone dependent cancer.

[34] a composition of the above [30] for preventing and/or treating prostatic cancer, uterine cancer or breast cancer;

[35] a composition of the above [30] for preventing and/or treating prostatic hypertrophy, endometriosis, hysteromyoma or precocious puberty;

[36] a composition of the above [30] which is a pregnancy regulator;

[37] a composition of the above [30] which is a menstruation cycle regulator;

[38] a method for antagonizing gonadotropin-releasing hormone in a mammal in need thereof which comprises administering to said mammal an effective amount of a compound of the above [1] or a salt thereof with a pharmaceutically acceptable excipient, carrier or diluent;

[39] use of a compound of the above [1] or a salt thereof for manufacturing a pharmaceutical composition for antagonizing gonadotropin-releasing hormone; and so forth.

In the above formulas, the group bound via a carbon atom includes (1) a hydrocarbon group which may be substituted, (2) an acyl group which may be substituted, (3) a heterocyclic group having a bond in a carbon atom thereof which may be substituted, (4) a carboxy group which may be esterified or amidated, or (5) a cyano group.

In the above formulas, the group bound via a nitrogen atom includes (1) a nitro group or (2) a group of the formula: —$NR^8R^9$ wherein $R^8$ represents hydrogen, a hydrocarbon group which may be substituted; an acyl group which may be substituted, a hydroxy group which may be substituted, a heterocyclic group which may be substituted, or a group of the formula: —S(O)t-$R^{12}$ wherein t represents an integer from 0 to 2, and $R^{12}$ represents hydrogen or a $C_{1-10}$ hydrocarbon group which may be substituted; $R^9$ represents hydrogen, a hydrocarbon group which may be substituted or an acyl group which may be substituted; or $R^8$ and $R^9$ may form, taken together with the adjacent nitrogen atom, a cyclic amino group which may be substituted.

In the above formulas, the group bound via an oxygen atom includes a hydroxy group which may be substituted. The hydroxy group which may be substituted is represented by the formula: —O—$R^{13}$ wherein $R^{13}$ represents hydrogen or a $C_{1-10}$ hydrocarbon group which may be substituted, a $C_{1-20}$ acyl group which may be substituted, a $C_{1-20}$ alkylsulfonyl group which may be substituted, a $C_{6-14}$ arylsulfonyl group which may be substituted or a heterocyclic group which may be substituted.

In the above formulas, the group bound via a sulfur atom is a group of the formula: —S(O)t-$R^{14}$ wherein t represents an integer from 0 to 2, and $R^{14}$ represents hydrogen or a hydrocarbon group which may be substituted or a heterocyclic group which may be substituted.

The above-described carboxy group which may be esterified is a group of the formula: —COO—$R^{21}$ wherein $R^{21}$ represents hydrogen or a hydrocarbon group which may be substituted.

The above-described carboxy group which may be amidated is a group of the formula: —CO—$NR^{15}R^{16}$ wherein $R^{15}$ represents hydrogen, a hydrocarbon group which may be substituted, an alkoxy group; $R^{16}$ represents hydrogen or a hydrocarbon group which may be substituted; or $R^{15}$ and $R^{16}$ may form, taken together with the adjacent nitrogen atom, a cyclic amino group which may be substituted. The carboxy group which may be amidated is preferably exemplified by a group represented by —$CONH_2$, and mono- or di-$C_{1-15}$ alkylcarbamoyl groups, preferably mono- or di-$C_{1-10}$ alkylcarbamoyl groups (e.g., methylcarbamoyl, ethylcarbamoyl, hexylcarbamoyl, dimethylcarbamoyl, methylethylcarbamoyl).

The hydrocarbon group in the above-described hydrocarbon group which may be substituted is preferably a $C_{1-20}$ hydrocarbon group, preferably $C_{1-10}$ hydrocarbon group. The $C_{1-20}$ hydrocarbon group is exemplified by (1) $C_{1-15}$ alkyl groups (e.g., methyl, ethyl, n-propyl, isopropyl, n-butyl, sec-butyl, t-butyl, pentyl, hexyl, heptyl, octyl, nonyl, decyl, undecyl, dodecyl, tridecyl, tetradecyl, pentadecyl, etc.; preferably $C_{1-10}$ alkyls, more preferably $C_{1-6}$ alkyl groups), (2) $C_{3-10}$ cycloalkyl groups (e.g., cyclopropyl, cyclobutyl, cyclopentyl, cyclohexyl, cycloheptyl, cyclooctyl, cyclononyl, etc.; preferably $C_{3-6}$ cycloalkyl groups), (3) $C_{2-10}$ alkenyl groups (e.g., vinyl, allyl, isopropenyl, 1-butenyl, 2-butenyl, 3-butenyl, butadienyl, 2-methylallyl, hexatrienyl, 3-octenyl, etc.; preferably $C_{2-6}$ alkenyl groups, (4) $C_{2-10}$ alkynyl groups (e.g., ethynyl, 2-propynyl, isopropynyl, butynyl, t-butynyl, 3-hexynyl, etc.; preferably $C_{2-6}$ alkynyl groups), (5) $C_{3-10}$ cycloalkenyl groups (e.g., cyclopropenyl, cyclopentenyl, cyclohexenyl, etc.; preferably $C_{3-6}$ cycloalkenyl groups), (6) $C_{6-14}$ aryl groups (e.g., phenyl, naphthyl, anthryl, phenanthryl, acenaphthyl, anthracenyl, etc.; preferably phenyl and naphthyl), and (7) $C_{7-20}$ aralkyl groups (e.g., $C_{6-14}$ aryl-$C_{1-6}$ alkyls such as benzyl, phenethyl and benzhydryl, preferably phenyl-$C_{1-6}$ alkyls such as benzyl and phenethyl).

Such hydrocarbon groups may have 1 to 6, preferably 1 to 5, and more preferably 1 to 3 substituents at any possible positions. Such substituents include, for example, (1) halogen, (2) nitro, (3) nitroso, (4) cyano, (5) hydroxy which may be substituted, for example, hydroxy which may be substituted by (i) $C_{1-6}$ alkyl (the $C_{1-6}$ alkyl may be substituted by 1 to 3 substituents selected from the group consisting of hydroxy, $C_{1-6}$ alkoxy, $C_{1-3}$ alkoxy-$C_{1-3}$ alkoxy, $C_{1-3}$ alkylthio, hydroxy-$C_{1-3}$ alkoxy, $C_{1-6}$ alkyl-carbonyl, carboxy, carbamoyl, $C_{1-6}$ alkyl-carbamoyl, 5- to 8-membered heterocyclic group (same as the "5- to 8-membered heterocyclic group containing 1 to 4 hetero atoms selected from oxygen atoms, sulfur atoms, nitrogen atoms etc., in addition to carbon atoms" described below) and halogen, etc.], (ii) $C_{1-4}$ acyl (e.g., $C_{1-4}$ alkanoyl, $C_{2-4}$ alkenoyl), (iii) $C_{7-20}$ aralkyl (the $C_{7-20}$ aralkyl is $C_{6-14}$ aryl-$C_{1-6}$ alkyl and may be substituted by 1 to 3, preferably 1 halogen, $C_{1-3}$ alkoxy or $C_{1-4}$ alkyl), (iv) $C_{6-14}$ aryl (the $C_{6-14}$ aryl may be substituted by 1 to 3, preferably 1 halogen), (v) $C_{2-6}$ alkenyl, (vi) $C_{3-7}$ cycloalkyl, (vii) $C_{1-3}$ alkoxy-carbonyl, (viii) mono- or di-$C_{1-6}$ alkylamino, (ix) $C_{2-6}$ alkenylamino, (x) $C_{1-3}$ alkoxy-carbonyl, (xi) $C_{1-6}$ alkyl-carbonyl or (xii) $C_{3-6}$ cycloalkyloxy-carbonyl, (6) a group of the formula: —S(O)t-$R^{17}$ wherein t represents an integer from 0 to 2; $R^{17}$ represents hydrogen or a hydrocarbon group which may be substituted by 1 to 3, preferably 1 substituent (e.g., halogen, nitro, cyano, hydroxy, oxo, thioxo, carboxy, cyano-$C_{6-14}$ aryl, halogeno-$C_{6-14}$ aryl) at any possible positions; the hydrocarbon group is preferably $C_{1-20}$ hydrocarbon group, more preferably $C_{1-6}$ alkyl, $C_{6-14}$ aryl or $C_{7-20}$ aralkyl, (7) amino which may be substituted, for example, a group of the formula: —$NR^{18}R^{19}$ wherein $R^{18}$ and $R^{19}$ each represents hydrogen, $C_{1-6}$ alkyl, $C_{1-6}$ alkylamino-$C_{1-6}$ alkyl, $C_{1-6}$ alkoxy, $C_{2-6}$ alkenyl, $C_{3-7}$ cycloalkyl, phenyl, phenyl-$C_{1-6}$ alkyl, $C_{1-6}$ alkanoyl, $C_{3-6}$ alkenoyl, $C_{4-7}$ cycloalkyl-carbonyl, phenyl-$C_{1-6}$ alkyl-carbonyl, $C_{1-6}$ alkyloxy-carbonyl, phenyl-$C_{1-6}$ alkoxy-carbonyl, or a 5- to 8-membered heterocyclic group (the same as the "5- to 8-membered heterocyclic group containing 1 to 4 hetero atoms selected from oxygen atoms, sulfur atoms, nitrogen atoms etc., in addition to carbon atoms" described below.) (8) a group of the formula: —CO—$R^{20}$ wherein $R^{20}$ represents (i) hydrogen, (ii) hydroxy, (iii) $C_{1-10}$ alkyl, (iv) $C_{1-6}$ alkoxy (this alkoxy may be substituted by $C_{6-14}$ aryl which may be substituted by 1 to 3, preferably 1 halogen or nitro, at any possible position), (v) $C_{3-6}$ cycloalkyl, (vi) $C_{6-14}$ aryl, (vii) $C_{6-14}$ aryloxy, (viii) $C_{7-20}$ aralkyl, (ix) group of the formula: —$NR^{10}R^{11}$ wherein $R^{10}$ and $R^{11}$ have the same definitions as those given above, or (x) 5- to 8-membered heterocyclic group (the same as the above-described "5- to 8-membered heterocyclic group containing 1 to 4 hetero atoms selected from oxygen atoms, sulfur atoms, nitrogen atoms etc., in addition to carbon atoms") (e.g., $C_{1-6}$ alkanoyl, $C_{3-6}$ alkenoyl, $C_{1-6}$ alkoxy-carbonyl, etc. are preferred), (9) 5- to 8-membered heterocyclic group containing 1 to 4 hetero atoms selected from nitrogen atoms, oxygen atoms and sulfur atoms, (10) sulfo, (11) $C_{6-14}$ aryl, (12) $C_{3-7}$ cycloalkyl, (13) $C_{1-6}$ alkylenedioxy (e.g., methylenedioxy, ethylenedioxy, propylenedioxy, 2,2-dimethylenedioxy), (14) oxo, (15) thioxo, (16) $C_{2-4}$ alkynyl, (17) $C_{3-10}$ cycloalkyl, (18) $C_{2-10}$ alkenyl (preferably $C_{2-6}$ alkenyl), (19) $C_{7-20}$ aralkyl ($C_{6-14}$ aryl-$C_{1-6}$ alkyl), (20) amidino, and (21) azide.

Of the above-mentioned substituents on hydrocarbon groups having substituents, (9) 5- to 8-membered heterocyclic group containing 1 to 4 hetero atoms selected from nitrogen atoms, oxygen atoms and sulfur atoms, (11) $C_{6-14}$ aryl, (12) $C_{3-7}$ cycloalkyl, (16) $C_{2-4}$ alkynyl, (7) $C_{3-10}$ cycloalkyl, (18) $C_{2-10}$ alkenyl, (19) $C_{7-20}$ aralkyl etc. may further have 1 to 4, preferably 1 to 3 substituents at any possible positions. Such substituents which may be further contained include, for example, 1 to 3, preferably 1 to 2 groups selected from the group consisting of (1) hydroxy, (2)

amino, (3) mono- or di-$C_{1-4}$ alkylamino (e.g., methylamino, ethylamino, propylamino, dimethylamino, diethylamino), (4) $C_{1-4}$ alkoxy, (5) halogen, (6) nitro, and (7) $C_{1-6}$ alkyl, etc.

When the hydrocarbon group is a cycloalkyl, cycloalkenyl, aryl or aralkyl group, it may be substituted by 1 to 3 $C_{1-6}$ alkyl. The $C_{1-6}$ alkyl may be further substituted by 1 to 3 substituents selected from the group consisting of hydroxy, oxo, $C_{1-3}$ alkoxy, $C_{1-3}$ alkylthio, halogen, and carbamoyl, etc.

Such substituted $C_{1-6}$ alkyl is exemplified by formyl (resulting from methyl substitution by oxo), carboxy (resulting from methyl substitution by oxo and hydroxy), $C_{1-6}$ alkoxycarbonyl (resulting from methyl substitution by oxo and alkoxy) (e.g., $C_{1-6}$ alkoxycarbonyl such as methoxycarbonyl, ethoxycarbonyl and t-butoxycarbonyl), hydroxy-$C_{1-6}$ alkyl (e.g., hydroxymethyl, hydroxyethyl, hydroxybutyl, hydroxypropyl), and $C_{13}$ alkoxy-$C_{1-6}$ alkyl (e.g., methoxymethyl, ethoxymethyl, ethoxybutyl, propoxymethyl, propoxyhexyl), etc.

Although the number of such substituents ranges from 1 to 6, it is preferably 1 to 5, more preferably 1 to 3, and most preferably 1 to 2. The number of substituents which may be further contained in such substituents is preferably 1 to 4, more preferably 1 to 3, and most preferably 1 to 2.

The acyl group in the above acyl group which may be substituted, which is mentioned to exemplify the group bound via a carbon atom, $R^8$ and $R^9$, includes, for example, $C_{1-20}$ acyl groups such as formyl, $C_{1-6}$ alkyl-carbonyl (e.g., acetyl, ethylcarbonyl, propylcarbonyl, tert-propylcarbonyl), $C_{1-6}$ alkoxy-carbonyls (e.g., methoxycarbonyl, ethoxycarbonyl, t-butoxycarbonyl), $C_{6-14}$ aryl-carbonyl (e.g., benzoyl, naphthoyl), $C_{6-14}$ aryloxy-carbonyl (e.g., phenoxycarbonyl), $C_{7-15}$ aralkyl-carbonyl (e.g., $C_{6-14}$ aryl-$C_{1-6}$ alkyl-carbonyl such as benzylcarbonyl), $C_{7-19}$ aralkyloxy-carbonyl (e.g., $C_{6-14}$ aryl-$C_{1-6}$ alkoxy-carbonyl such as benzyloxycarbonyl), $C_{2-4}$ alkenyl-carbonyl (e.g., 2-propenylcarbonyl), tricyclic $C_{9-10}$ bridged hydrocarbon-carbonyl (e.g., adamantylcarbonyl), etc.

Substituents in the acyl group which may be substituted are exemplified by the same groups as those mentioned to exemplify substituents in the above-described hydrocarbon group which may be substituted.

In the above formulas, the heterocyclic group or the heterocyclic group in the heterocyclic group which may be substituted includes, for example, 5-to 8-membered heterocyclic groups containing 1 to 4 hetero atoms selected from oxygen atoms, sulfur atoms, nitrogen atoms etc., in addition to carbon atoms, bicyclic or tricyclic condensed heterocyclic groups resulting from condensation of 2 or 3 of such heterocyclic groups, whether identical or not, and bicyclic or tricyclic condensed heterocyclic groups resulting from condensation of such a heterocyclic group and 1 or 2 benzene rings.

Examples of the heterocyclic group include, for example, (1) 5-membered heterocyclic groups containing 1 to 4 hetero atoms selected from oxygen atoms, sulfur atoms, nitrogen atoms etc., in addition to carbon atoms, such as thienyl, furyl, pyrrolyl, pyrrolinyl, oxazolyl, thiazolyl, pyrazolyl, imidazolyl, imidazolinyl, isoxazolyl, isothiazolyl, 1,2,4-oxadiazolyl, 1,3,4-oxadiazolyl, furazanyl, 1,2,4-thiadiazolyl, 1,2,3-thiadiazolyl, 1,2,5-thiadiazolyl, 1,2,3-triazolyl, 1,2,4-triazolyl, triazinyl, triazolidinyl, and 1H- or 2H-tetrazolyl; and (2) 6-membered heterocyclic groups containing 1 to 4 hetero atoms selected from oxygen atoms, sulfur atoms, nitrogen atoms etc., in addition to carbon atoms, such as pyridyl, pyrimidinyl, thiomorpholinyl, morpholinyl, triazinyl, pyrrolidinyl, piperidinyl, pyranyl, thiopyranyl, 1,4-oxazinyl, 1,4-thiazinyl, 1,3-thiazinyl, piperazinyl, triazinyl, oxatriazinyl, pyridazinyl and pyrazinyl. (3) Bicyclic or tricyclic condensed heterocyclic groups include bicyclic or tricyclic condensed heterocyclic groups containing 1 to 4 hetero atoms selected from oxygen atoms, sulfur atoms, nitrogen atoms etc., in addition to carbon atoms, such as benzofuryl, benzothiazolyl, benzoxazolyl, tetrazolo[1,5-b]pyridazinyl, triazolo[4,5-b]pyridazinyl, benzimidazolyl, quinolyl, isoquinolyl, cinnolinyl, phthalazinyl, quinazolinyl, quinoxalinyl, indolizinyl, indolyl, quinolizinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl and phenoxazinyl.

Examples of substituents of the heterocyclic group which may be substituted include, for example (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{7-11}$ aralky ($C_{6-10}$ aryl-$C_{1-5}$ alkyl such as benzyl and phenethyl, preferably benzyl), (7) $C_{6-14}$ aryl (phenyl, naphthyl, anthryl, phenanthryl, acenaphtyl, anthracenyl, etc., preferably phenyl), (8) $C_{1-6}$ alkoxy, (9) $C_{6-14}$ aryloxy (e.g., phenoxy), (10) $C_{1-6}$ alkanoyl (e.g., formyl, acetyl, propionyl, n-butyryl, iso-butyryl), (11) $C_{6-14}$ arylcarbonyl (e.g., benzoyl), (12) $C_{1-6}$ alkanoloxy (e.g., formyloxy, acetyloxy, propionyloxy, n-butylyloxy, iso-butylyloxy), (13) $C_{6-14}$ aryl-carbonyloxy (e.g., benzoyloxy), (14) carboxy, (15) $C_{1-6}$ alkoxy-carbonyl (e.g., methoxycarbonyl, ethoxycarbonyl, n-propoxycarbonyl, iso-propoxycarbonyl, n-butoxycarbonyl, isobutoxycarbonyl, tert-butoxycarbonyl), (16) carbamoyl, (17) N-mono-$C_{1-4}$ alkylcarbamoyl (e.g., N-methylcarbamoyl, N-ethylcarbamoyl, N-propylcarbamoyl, N-isopropylcarbamoyl, N-butylcarbamoyl), (18) N,N-di-$C_{1-4}$ alkylcarbamoyl (e.g., N,N-dimethylcarbamoyl, N,N-diethylcarbamoyl, N,N- dipropylcarbamoyl, N,N-dibutylcarbamoyl), (19) 3- to 6-membered cyclic aminocarbonyl (e.g., 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl), (20) halogen, (21) mono-, di- or tri-halogeno-$C_{1-4}$ alkyl (e.g., chloromethyl, dichloromethyl, trifluoromethyl, trifluoroethyl), (22) oxo, (23) amidino, (24) imino, (25) amino, (26) mono- or di-$C_{1-4}$ alkylamino (e.g., methylamino, ethylamino, propylamino, isopropylamino, butylamino, dimethylamino, diethylamino, dipropylamino, diisopropylamino, dibutylamino), (27) 3- to 6-membered cyclic amino which may contain 1 to 3 hetero atoms selected from oxygen atoms, sulfur atoms, nitrogen atoms etc., in addition to carbon atoms and a nitrogen atom (e.g., aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl, N-ethylpiperazinyl), (28) $C_{1-6}$ alkanoylanino (e.g., formamido, acetamido, trifluoroacetamido, propionylamido, butyrylamido, isobutyrylamido), (29) benzamido, (30) carbamoylamino, (31) N-$C_{1-4}$ alkylcarbamoylamino (e.g., N-methylcarbamoylamino, N-ethylcarbamoylamino, N-propyl-carbamoylamino, N-isopropylcarbamoylamino, N-butylcarbamoylamino), (32) N,N-di-$C_{1-4}$ alkylcarbamoylamino (e.g., N,N-dmethylcarbamoylamino, N,N-diethylcarbamoylamino, N,N-dipropylcarbamoylamino, N,N-dibutylcarbamoylamino), (33) $C_{1-3}$ alkylenedioxy (e.g., methylenedioxy, ethylenedioxy), (34) —B(OH)$_2$, (35) hydroxy, (36) epoxy (—O—), (37) nitro, (38) cyano, (39) mercapto, (40) sulfo, (41) sulfino, (42) phosphono, (43) sulfamoyl, (44) $C_{1-6}$ alkylsulfamoyl (e.g., N-methylsulfamoyl, N-ethylsulfamoyl, N-propylsulfamoyl, N-isopropylsulfamoyl, N-butylsulfamoyl), (45) di-$C_{1-6}$ alkylsulfamoyl (e.g., N,N-dimethylsulfamoyl, N,N-diethylsualfamoyl, N,N-dipropylsulfamoyl, N,N-dibutylsulfamoyl), (46) $C_{1-6}$ alkylthio (e.g., methylthio, ethylthio, propylthio, isopropylthio, n-butylthio, sec-butylthio, tert-butylthio), (47) phenylthio, (48) $C_{1-6}$ alkylsulfinyl (e.g., methylsulfinyl, ethylsulfinyl, propylsulfinyl, butylsulfinyl), (49) phenylsulfinyl, (50) $C_{1-6}$ alkylsulfonyl (e.g., methylsulfonyl, ethylsulfonyl, propylsulfonyl, butylsulfonyl), and (51) phenylsulfonyl.

The number of substituents which may substitute the heterocyclic group is 1 to 6, preferably 1 to 3, and more preferably 1 to 2.

The heterocyclic group in the heterocyclic group having a bond in a carbon atom thereof which may be substituted is exemplified by 5- to 8-membered heterocyclic groups containing 1 to 4 hetero atoms selected from oxygen atoms, sulfur atoms, nitrogen atoms etc., in addition to carbon atoms, bicyclic or tricyclic condensed heterocyclic groups resulting from condensation of 2 or 3 of such heterocyclic groups, whether identical or not, and bicyclic or tricyclic condensed heterocyclic groups resulting from condensation of such a heterocyclic group. and 1 or 2 benzene rings, which condensed heterocyclic groups have a bond in a constituent carbon atom thereof.

Examples of the heterocyclic group having a bond in a carbon atom thereof include, for example, (1) 5-membered heterocyclic groups containing 1 to 4 hetero atoms selected from oxygen atoms, sulfur atoms, nitrogen atoms etc., in addition to carbon atoms, such as thienyl (e.g., 2- or 3-thienyl), furyl (e.g., 2- or 3-furyl), pyrrolyl (e.g., 2- or 3-pyrrolyl), oxazolyl (e.g., 2-, 4- or 5-oxazolyl), thiazolyl (e.g., 2-, 4- or 5-thiazolyl), pyrazolyl (e.g., 3-, 4- or 5-pyrazolyl), pyrrolidinyl (e.g., 2- or 3-pyrrolidinyl), imidazolyl (e.g., 2-, 4- or 5-imidazolyl), imidazolinyl (e.g., 2-imidazolinyl, 2-imidazolidinyl), isoxazolyl (e.g., 3-, 4- or 5-isoxazolyl), isothiazolyl (e.g., 3-, 4- or 5-isothiazolyl), oxadiazolyl [e.g., 3- or 5-(1,2,4-oxadiazolyl), 2-, 5- or 6-(1,3,4-oxadiazolyl)], thiadiazolyl [e.g., 3- or 5-(1,2,4-thiadiazolyl), 2- or 5-(1,3,4-thiadiazolyl), 4- or 5-(1,2,3-thiadiazolyl), 3- or 4-(1,2,5-thiadiazolyl)], and triazolyl (e.g., 2- or 5-(1,2,3-triazolyl), 3- or 5-(1,2,4-triazolyl)], tetrazolyl [e.g., 5-(1H- or 2H-tetrazolyl)]; (2) 6-membered heterocyclic groups containing 1 to 4 hetero atoms selected from oxygen atoms, sulfur atoms, nitrogen atoms etc., in addition to carbon atoms, such as pyridyl (e.g., 2-, 3- or 4-pyridyl), pyrimidinyl (e.g., 2-, 4- or 5-pyrimidinyl), thiomorpholinyl (e.g., 2- or 3-thiomorpholinyl), morpholinyl (e.g., 2- or 3-morpholinyl), triazinyl (e.g., 3- or 6-triazinyl), piperidinyl (e.g., 2-, 3- or 4-piperidinyl), pyranyl (e.g., 2- or 3-pyranyl), thiopyranyl (e.g., 2- or 3-thiopyranyl), oxazinyl [e.g., 2-or 3-(1,4-oxazinyl)], thiazinyl [e.g., 2- or 3-(1,4-thiazinyl), 1- or 4-(1,3-thiazinyl)], piperazinyl (e.g., 2- or 3-piperazinyl), triazinyl (e.g., 3- or 6-triazinyl), and pyridazinyl (e.g., 3- or 4-pyridazinyl); and (3) bicyclic or tricyclic condensed heterocyclic groups containing 1 to 4 hetero atoms selected from oxygen atoms, sulfur atoms, nitrogen atoms etc., in addition to carbon atoms, and having a bond in a constituent carbon atom thereof, such as benzofuryl, benzothiazolyl, benzoxazolyl, tetrazolo[1,5-b]pyridazinyl, triazolo[4, 5-b]pyridazinyl, benzimidazolyl, quinolyl, isoquinolyl, cinnolinyl, phthalazinyl, quinazolinyl, quinoxalinyl, indolizinyl, indolyl, quinolizinyl, 1,8-naphthylidinyl, purinyl, pteridinyl, dibenzofuranyl, carbazolyl, acridinyl, phenanthridinyl, chromanyl, benzoxazinyl, phenazinyl, phenothiazinyl and phenoxazinyl.

The substituents in the heterocyclic group having a bond in a carbon atom thereof which may be substituted is exemplified by the same substituents mentioned to exemplify the above-described heterocyclic group which may be substituted.

The cyclic amino group and the cyclic amino group in the above-described cyclic amino group which may be substituted is exemplified by 5- to 7-membered nitrogen-containing cyclic groups which may have additional hetero atoms selected from oxygen atoms, sulfur atoms and nitrogen atoms. Examples of such groups include, for example, pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, azepinyl, hexamethyleneimino, oxazolidino, morpholino, thiazolidino and thiomorpholino. Preferred is 5- to 6-membered cyclic amino group, e.g., pyrrolidinyl, pyrazolinyl, pyrazolyl, piperidinyl, piperazinyl, morpholino and thiomorpholino.

The cyclic amino group may have 1 to 3 substituents at any possible positions, such substituents including, for example, (1) $C_{1-6}$ alkyl, (2) $C_{6-14}$ aryl, (3) $C_{7-10}$ aralkyl (phenyl-$C_{1-4}$ alkyl), (4) benzhydryl, (5) $C_{1-6}$ alkyl-carbonyl, (6) $C_{6-14}$ aryl-carbonyl, (7) $C_{1-6}$ alkoxy-carbonyl, etc. Preferred is $C_{1-6}$ alkyl, more preferred is $C_{1-3}$ alkyl.

The homocyclic group in the homocyclic group which tmay be substituted is exemplified by 3- to 7-membered carbocyclic groups which may be condensed, such as $C_{6-10}$ aryl groups (e.g., phenyl, naphtlhyl), $C_{3-7}$ cycloalkyl groups (e.g., cyclopropyl, cyclobutyl, cyclopentyl, cyclohexyl, cycloheptyl) and $C_{3-7}$ cycloalkenyl gropus (e.g., cyclopronyl, cyclobutenyl, cyclopentenyl, cyclohexenyl, cycloheptenyl).

Such homocyclic groups may have 1 to 6, preferably 1 to 3, and more preferably 1 to 2 substituents at any possible positions. Such substituents include, for example, (1) $C_{1-15}$ alkyl which may be substituted by 1 to 3, preferably 1 to 2 halogen(s), preferably $C_{1-6}$ alkyl which may be substituted by halogen, (2) $C_{3-10}$ cycloalkyl, (3) $C_{2-10}$ alkenyl, (4) $C_{2-10}$ alkynyl, (5) $C_{3-10}$ cycloalkenyl, (6) $C_{6-10}$ aryl, (7) $C_{7-20}$ aralkyl, (8) nitro, (9) hydroxy, (10) mercapto, (11) oxo, (12) thioxo, (13) cyano, (14) carbamoyl, (15) carboxy, (16) $C_{1-6}$ alkoxy-carbonyl (e.g., methoxycarbonyl, ethoxycarbonyl), (17) sulfo, (18) halogen, (19) $C_{1-6}$ alkoxy, (20) $C_{6-10}$ aryloxy (e.g., phenoxy), (21) $C_{1-6}$ acyloxy (e.g., $C_{1-6}$ alkanoyloxy such as acetoxy and propionyloxy), (22) $C_{1-6}$ alkylthio (e.g., methylthio, ethylthio, n-propylthio, isopropylthio, n-butylthio, t-butylthio), (23) $C_{6-10}$ arylthio (e.g., phenylthio), (24) $C_{1-6}$ alkylsulfinyl (e.g., methylsulfinyl, ethylsulfinyl), (25) $C_{6-10}$ arylsulfinyl (e.g., phenylsulfinyl), (26) $C_{1-6}$ alkylsulfonyl (e.g., methylsulfonyl, ethylsulfonyl, (27) $C_{6-10}$ arylsulfonyl (e.g., phenylsulfonyl), (28) amino, (29) $C_{1-6}$ acylamino (e.g., $C_{1-6}$ alkanoylamino such as acetylamino and propionylamino), (30) mono- or di-$C_{1-4}$ alkylamino (e.g., methylamino, ethylamino, n-propylamino, isopropylamino, n-butylamino, dimethylamino, diethylamino), (31) $C_{3-8}$ cycloalkylamino (e.g., cyclopropylamino, cyclobutylamino, cyclopentylamino, cyclohexylamino), (32) $C_{6-10}$ arylamino (e.g., anilino), (33) $C_{1-6}$ alkanoyl (e.g., formyl, acetyl, hexanoyl), (34) $C_{6-10}$ aryl-carbonyl (e.g., benzoyl), and (35) 5- to 6-membered heterocyclic groups containing 1 to 4 hetero atoms selected from oxygen atom, sulfur atom, and nitrogen atom, in addition to carbon atoms [e.g., thienyl (e.g., 2- or 3-thienyl), furyl (e.g., 2- or 3-furyl), pyrazolyl (e.g., 3-, 4- or 5-pyrazolyl), thiazolyl (e.g., 2-, 4- or 5-thiazolyl), isothiazolyl (e.g., 3-, 4- or 5-isothiazolyl), oxazolyl (e.g., 2-, 4- or 5-oxazolyl), isoxazolyl (e.g., 3-, 4- or 5-isoxazolyl), imidazolyl (e.g., 2-, 4- or 5-imidazolyl), triazolyl (e.g., 1,2,3- or 1,2,4-triazolyl), tetrazolyl (e.g., 1H- or 2H-tetrazolyl), pyridyl (e.g., 2-, 3- or 4-pyridyl), pyrimidyl (e.g., 2-, 4- or 5-pyriraidyl), pyridazinyl (e.g., 3- or 4-pyridazinyl), quinolyl, isoquinolyl, indolyl, etc.], and so forth.

The hydroxy group which may be substituted for $R^8$ and $R^{10}$ includes a group of the formula: —$OR^{13}$ wherein $R^{13}$ is defined as above.

In the above formulas, $R^1$, $R^2$ and $R^3$ each is preferably (i) hydrogen or (ii) the above-described group bound via a carbon atom, a nitrogen atom or an oxygen atom. Preference is given to the case wherein $R^1$ is a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted, a $C_{7-20}$ aralkyl group which may be substituted, a $C_{1-20}$ acyl group which may be substituted, a nitro group, a group of the formula: —$NR^{10}R^{11}$ wherein $R^{10}$ is hydrogen, a $C_{1-10}$ hydrocarbon group which may be substituted, a $C_{1-20}$ acyl group which may be substituted, a hydroxy group which may be substituted, a heterocyclic group which may be substituted, or a group of the formula: —$S(O)t$-$R^{12}$ wherein t is an integer from 0 to 2, and $R^{12}$ is hydrogen, a $C_{1-10}$ hydrocarbon group which may be substituted or a heterocyclic group; $R^{11}$ is hydrogen or a $C_{1-10}$ hydrocarbon group; or $R^{10}$ and $R^{11}$ may form, taken together with the adjacent nitrogen atom, a cyclic amino group which may be substituted, or a group of the formula: —O—$R^{13}$ wherein $R^{13}$ is hydrogen or a $C_{1-10}$ hydrocarbon group which may be substituted, a $C_{1-20}$ acyl group which may be substituted, a $C_{1-20}$ alkylsulfonyl group which may be substituted, a $C_{6-14}$ arylsulfonyl group which may be substituted or a 5- to 8-membered heterocyclic group (the same as the above-described "5- to 8-membered heterocyclic group containing 1 to 4 hetero atoms selected from oxygen atoms, sulfur atoms, nitrogen atoms etc., in addition to carbon atoms"), and wherein at least one of $R^2$ and $R^3$ is hydrogen, and the other is the above group bound via a carbon atom, a nitrogen atom, or an oxygen atom, preferably $R^2$ and $R^3$ are both hydrogen.

$R^1$ is preferably a Cllo alkyl group (preferably $C_{1-6}$ alkyl group) which may be substituted by 1 to 3, preferably 1 hydroxy, a nitro group, an amino group, a group of the formula: —$NR^{10}R^{11}$ wherein $R^{10}$ represents hydrogen; $R^1$ represents a $C_{1-6}$ alkyl-carbonyl group which may be substituted by 1 to 3, preferably 1 hydroxy, a $C_{1-6}$ alkylaminocarbonyl group or a $C_{6-14}$ arylamino-carbonyl group), or a group of the formula: —O—$R^{13}$ wherein $R^{13}$ represents hydrogen, a $C_{1-10}$ alkyl group which may be substituted by 1 to 3, preferably 1 hydroxy, a $C_{1-6}$ alkyl-carbonyl which may be substituted by $C_{3-10}$ cycloalkyl or 1 to 3, preferably 1 hydroxy, a $C_{1-6}$ alkylsulfonyl group, or a $C_{6-10}$ arylsulfonyl group.

In the above formulas, $R^4$ is preferably (1) a $C_{1-20}$ hydrocarbon group which may be substituted, (2) a $C_{1-20}$ acyl group which may be substituted, (3) a heterocyclic group having a bond in a carbon atom thereof which may be substituted, (4) a carboxy group which may be esterified or amidated, or (5) a cyano group. More preferably, $R^4$ is a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted or a $C_{7-20}$ aralkyl group which may be substituted. Still more preferred is a $C_{1-6}$ alkyl group which may be substituted such as an aminoalkyl group which may be substituted. A preferred example of $R^4$ is the formula: —$(CH_2)n$-$NR^{10}R^{11}$ wherein n is an integer from 1 to 3; $R^{10}$ is hydrogen, a $C_{1-10}$ hydrocarbon group which may be substituted, a $C_{1-20}$ acyl group which may be substituted, a hydroxy group which may be substituted (group of the formula: —O—$R^{13}$ above), a heterocyclic group which may be substituted, or a group of the formula: —$S(O)t$-$R^{12}$ wherein t is an integer from 0 to 2; $R^{12}$ is hydrogen or a $C_{1-10}$ hydrocarbon group which may be substituted; $R^{11}$ is hydrogen or a $C_{1-10}$ hydrocarbon group; or $R^{10}$ and $R^{11}$ may form, taken together with the adjacent nitrogen atom, a cyclic amino group which may be substituted. $R^4$ is more preferably a halogen atom, a hydroxy group which may be substituted by $C_{1-20}$ acyl, or a $C_{1-3}$ alkyl group which may be substituted by amino group which may be substituted by $C_{1-10}$ alkyl and/or $C_{6-14}$ aryl-$C_{1-10}$ alkyl. $R^4$ is most preferably N-$C_{1-6}$ alkyl-N-benzylaminomethyl.

In the above formulas, $R^5$ is preferably hydrogen or a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted, a $C_{7-20}$ aralkyl group which may be substituted, a $C_{1-20}$ acyl group which may be substituted, a carboxy group which may be esterified or amidated, or a group of the formula: —O—$R^{13}$ wherein $R^{13}$ is hydrogen, a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted, a $C_{7-20}$ aralkyl group which may be substituted, a $C_{1-20}$ acyl group which may be substituted, a $C_{1-20}$ alkylsulfonyl group which may be substituted, a $C_{6-14}$ arylsulfonyl group which may be substituted or a heterocyclic group which may be substituted. Preferred examples of $R^5$ include hydrogen, a $C_{1-15}$ alkyl group which may be substituted by 1 to 3, preferably 1 $C_{6-14}$ aryl or $C_{1-6}$ alkoxy, or a $C_{1-6}$ alkyl-carbonyl, $C_{1-6}$ alkoxycarbonyl (e.g., methoxycarbonyl, ethoxycarbonyl, t-butoxycarbonyl), $C_{6-14}$ aryl-carbonyl (e.g., benzoyl), $C_{6-14}$ aryloxy-carbonyl (e.g., phenoxycarbonyl), $C_{7-15}$ aralkyl-carbonyl (e.g., benzylcarbonyl), $C_{7-19}$ aralkyloxy-carbonyl (e.g., benzyloxycarbonyl), N-$C_{1-10}$ alkyl-N-($C_{1-10}$ alkoxy)amino-carbonyl (e.g., N-methyl-N-methoxyamino-carbonyl), $C_{1-15}$ alkyloxy and $C_{1-20}$ arylsulfonyl group which may be substituted by 1 to 3, preferably 1 hydroxy. More preferred is (1) a $C_{1-6}$ alkoxy-carbonyl group, (2) a $C_{6-10}$ aryl group which may be substituted by halogen or $C_{1-6}$ alkoxy, or (3) a phenyl-$C_{1-3}$ alkyl group.

In the above formulas, $R^6$ is preferably hydrogen, a $C_{1-15}$ alkyl group which may be substituted, a $C_{3-10}$ cycloalkyl group which may be substituted, a $C_{2-10}$ alkenyl group which may be substituted, a $C_{2-10}$ alkynyl group which may be substituted, a $C_{3-10}$ cycloalkenyl group which may be substituted, a $C_{6-14}$ aryl group which may be substituted or a $C_{7-20}$ aralkyl group which may be substituted. More preferably, $R^6$ is hydrogen or a $C_{1-10}$ alkyl group. Still more preferably, $R^6$ is hydrogen or a $C_{1-6}$ alkyl group.

In the above formulas, $R^7$ is a homocylic group or heterocyclic group which may be substituted, preferably a $C_{6-14}$ aryl group which may be substituted. More preferably, $R^7$ is a phenyl group which may be substituted by 1 to 3, preferably 1 to 2 halogen or $C_{1-6}$ alkoxy. Particularly preferred is a phenyl group which may be substituted by 1 to 2 halogen(s).

In the above formula (I), m is 0 to 3, preferably 0 to 2, and more preferably 0 or 1.

In the above formula, n is an integer from 1 to 3, preferably 1 or 2, and more preferably 1.

In the above formula or the following formula, each of X, $X^1$ and $X^2$ represents a leaving group (e.g., halogen atoms, mesyl, tosyl), preferably halogen atoms (e.g., chlorine, bromine).

In the following formula, $X^3$ represents a leaving group, for example, N,N-di-$C_{1-4}$ alkylamino (e.g., dimethylamino), $C_{1-10}$ alkoxy (e.g., methoxy, ethoxy), $C_{1-10}$ acyl (e.g., $C_{1-10}$ alkanoyl such as acetyl), $C_{1-10}$ acyloxy (e.g., $C_{1-10}$ alkanoyloxy such as acetoxy), halogen atoms (e.g., chlorine, bromine), mesyl, tosyl, etc. Preferably, $X^3$ is N,N-di-$C_{1-4}$ alkylamino (e.g., dimethylamino) and $C_{1-10}$ alkoxy (e.g., methoxy, ethoxy).

In the above formula (I), one of A and D represents a nitrogen atom and the other represents a carbon atom, or both represent a nitrogen atom; B represents a nitrogen atom or a carbon atom. Compounds represented by the formula (I) are therefore exemplified by compounds represented by the following formulas:

(a)
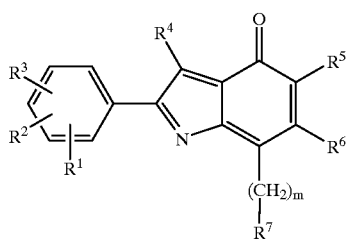

(b)
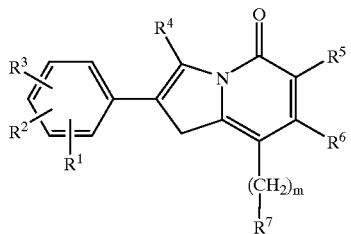

(c)
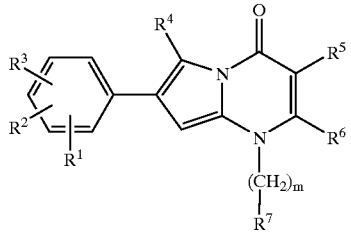

(d)
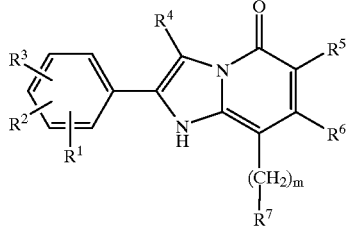

(e)
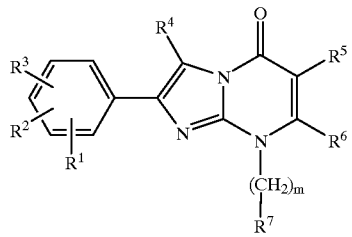

(f)
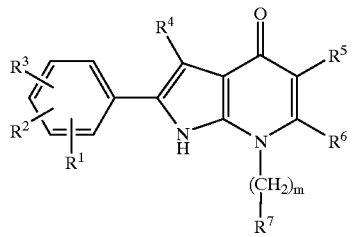

(g)
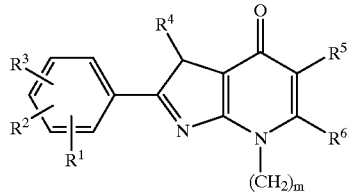

wherein the symbols have the same definitions as those given above, preferably compounds represented by the formula (a), (b), (c), (d), (e) or (g).

Among others, preferred is a compound of formula (I) wherein B is a nitrogen atom, more preferred is a compound represented by the formula (c) or (e), and most preferred is a compound represented by the formula (e).

In compound (I), preferred is a compound of the formula:

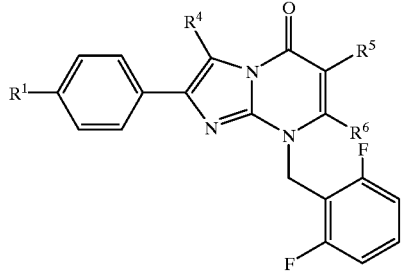

wherein each symbol is as defined above, or a salt thereof. Among others, preferred is a compound wherein $R^1$ is (1) an amino group which may be substituted by (i) carbamoyl which may be substituted by $C_{1-6}$ alkyl or $C_{1-6}$ alkoxy, or (ii) $C_{1-6}$ alkyl-carbonyl, or (2) a $C_{1-6}$ alkoxy group which may be substituted by $C_{3-6}$ cycloalkyl; $R^4$ is a N-$C_{1-6}$ alkyl-N-benzylaminomethyl group $R^5$ is (1) a $C_{1-6}$ alkoxy-carbonyl group, (2) a $C_{6-10}$ aryl group which may be substituted by halogen or $C_{1-6}$ alkoxy, or (3) a phenyl-$C_{1-3}$ alkyl group; and $R^6$ is hydrogen.

Another preferable example is a compound or a salt thereof, wherein $R^1$ is (1) a nitro group, (2) an amino group which may be substituted by 1 or 2 substituents selected from the group consisting of (i)

$C_{1-6}$ alkyl which may be substituted by hydroxy, (ii) $C_{1-6}$ alkyl-carbonyl which may be substituted by hydroxy, halogen or thienyl, (iii) $C_{6-10}$ aryl-carbonyl which may be substituted by $C_{1-6}$ alkyl, $C_{1-6}$ alkoxy or halogen, (iv) $C_{3-6}$ cycloalkyl-carbonyl, (v) $C_{2-4}$ alkenyl-carbonyl, (vi) $C_{1-6}$ alkoxy-carbonyl, (vii) $C_{1-6}$ alkylamino-carbonyl, (viii) $C_{1-6}$ alkoxyamino-carbonyl, (ix) phenylaminocarbonyl, (x) an isoxazolylcarbonyl, thienylcarbonyl, thiazolylcarbonyl, pyrazolylcarbonyl or furylcarbonyl group which may be substituted by 1 or 2 substituents selected from the group consisting of $C_{1-6}$ alkyl, nitro and $C_{1-6}$ alkoxy, (xi) pyridylcarbonyl, (xii) $C_{1-6}$ alkylsulfonyl, (xiii) thienylsulfonyl and (xiv) phenylsulfonyl which may be substituted by $C_{1-6}$ alkyl, (3) a pyrrolyl group or (4) a hydroxy group which may be substituted by $C_{1-6}$ alkyl, $C_{3-6}$ cycloalkyl-$C_{1-3}$ alkyl or $C_{1-6}$ alkyl-carbonyl;

$R^4$ is a $C_{1-6}$ alkyl group which may be substituted by 1 or 2 substituents selected from the group consisting of (1) halogen, (2) hydroxy and (3) amino which may be substituted by 1 or 2 substituents selected from the group consisting of $C_{1-6}$ alkyl, phenyl-$C_{1-3}$ alkyl and di-$C_{1-6}$ alkylamino-$C_{1-3}$ alkyl;

$R^5$ is (1) halogen, (2) a phenyl group which may be substituted by halogen or $C_{1-6}$ alkyl, or (3) a carbonyl group substituted by (i) $C_{1-6}$ alkyl, (ii) amino substituted by $C_{1-6}$ alkyl and $C_{1-6}$ alkoxy or (iii) $C_{1-6}$ alkoxy; and $R^6$ is hydrogen or a $C_{1-3}$ alkyl group.

As compound (I), concretely mentioned are 8-(2,6-difluorobenzyl)-5,8-dihydro-2-[4-(ethylaminocarbonylamino)phenyl]-3-(N-methyl-N-benzylaminomethyl)-5-oxoimidazo[1,2-a]pyrimidine-6-carboxylic acid ethyl ester, 8-(2,6-difluorobenzyl)-5,8-dihydro-2-[4-(methoxyaminocarbonylamino)phenyl]-3-(N-methyl-N-benzylaminomethyl)-5-oxoimidazo[1,2-a]pyrimidine-6-carboxylic acid isopropyl ester, 8-(2,6-difluorobenzyl)-5,8-dihydro-2-[4-(ethylaminocarbonylamino)phenyl]-3-(N-methyl-N-benzylaminomethyl)-5-oxoimidazo[1,2-a]pyrimidine-6-carboxylic acid isopropyl ester, or salts thereof.

The compound of the present invention can be produced by the methods described below or analogous thereto, per se known methods such as methods described in WO 95/28405, or combination thereof.

Production Method 1

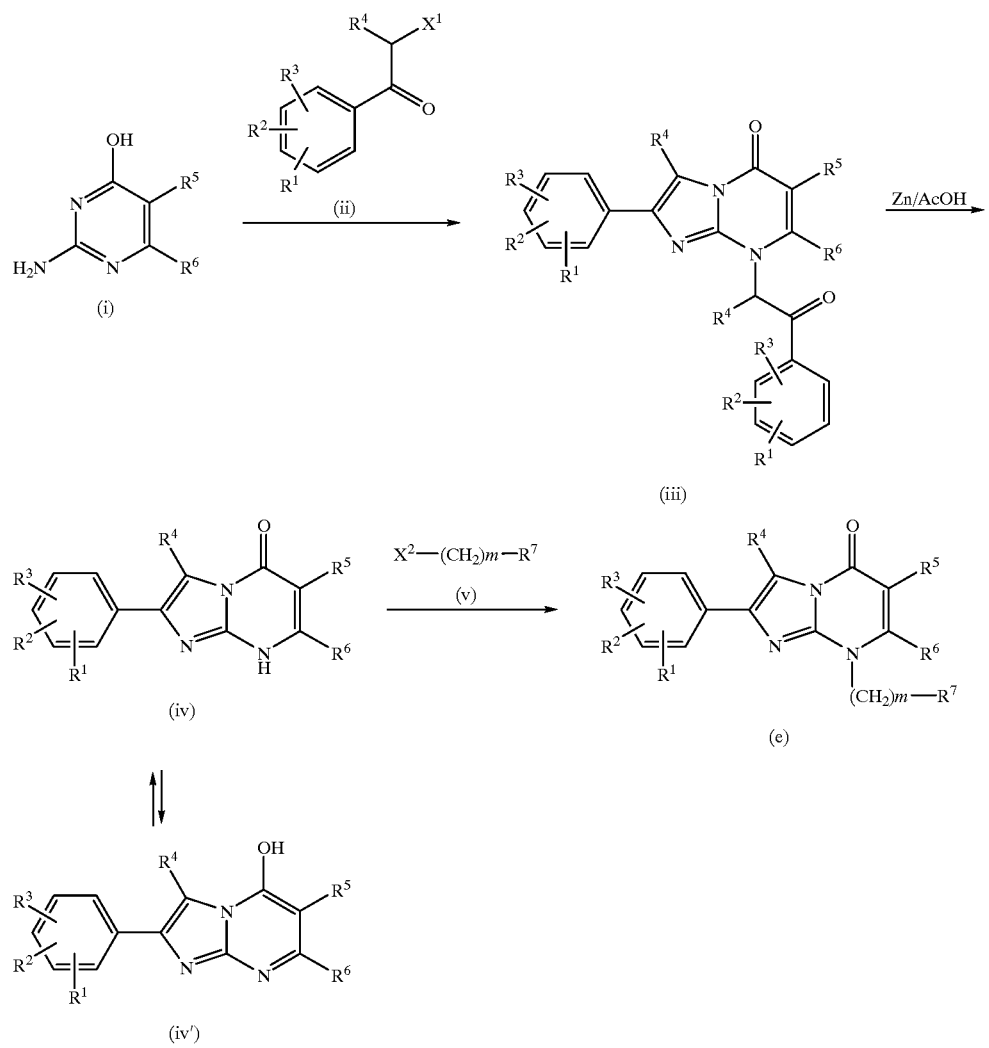

wherein the symbols have the same definitions as those given above

2-Aminopyrimidine derivative (i) is dissolved in an appropriate inert solvent (e.g., ethers such as ethyl ether, dioxane, dime thoxye thane and tetrahydrofuran, aromatic hydrocarbons such as benzene and toluene, amides such as dimethylformamide and dimethylacetamide, alcohols such as methanol and ethanol, dichloromethane, acetone, etc.), and then, 1 eq. to slight excess (about 1 to 3 mol) of α-haloketone derivative (ii) is added, followed by stirring at about 0 to 40° C. for about 1 to 4 hours, to yield cyclized derivative (iii). This (iii) is added little by little to an appropriate solvent (e.g., acetic acid), followed by addition of an appropriate metal (e.g., zinc powder) during stirring at about 0 to 80° C., to yield condensed derivative (iv). The aminopyrimidine derivative can be produced by a per se known methods, for example, methods described in the Journal of the Indian Chemical Society, 2, 61–70 (1925).

The derivative (iv) or its tautomer (iv') is dissolved in an appropriate inert solvent (e.g., dimethylformamide, dichloromethane, tetrahydrofuran, ethyl ether, dioxane and acetone), and then 1 eq. to slight excess (about 1 to 3 mol) of a base (e.g., potassium carbonate, triethylamine and sodium hydride) and 1 eq. to excess of compound (v) (e.g., halogenated alkyl derivatives such as benzyl iodide) are added, followed by stirring at about 0 to 80° C. Desired compound (e) can be thus produced.

This reaction is also carried out in the presence of a base. The base is exemplified by inorganic bases such as sodium carbonate, sodium hydrogen carbonate, potassium carbonate, potassium hydrogen carbonate, sodium hydroxide, potassium hydroxide and thallium hydroxide, and organic bases such as triethylamine. Reaction temperature is normally about 0 to 150° C., preferably about 15 to 25° C. (about 20° C.). Reaction time is about 1 to 12 hours.

Production Method 2

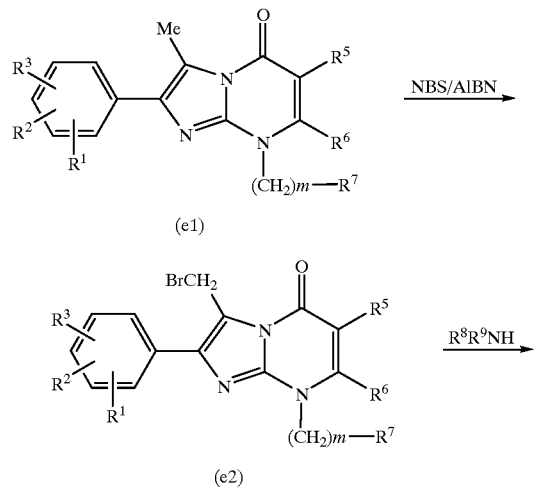

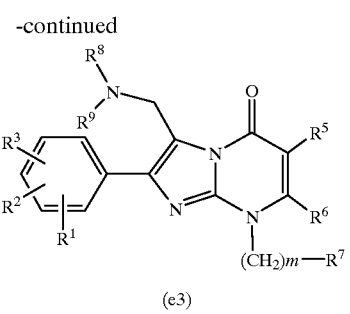

wherein the symbols have the same definitions as those given above

Conversion of 3-position substituent on imidazopyrimidine backbone:

Compound (e1) is stirred with N-bromosuccinimide (NBS) in a solvent that does not affect the reaction (e.g., halogenated hydrocarbons such as carbon tetrachloride and chloroform) in the presence of α, α'-azobisisobutyronitrile (AIBN) at 30 to 100° C. for 0.5 to 6 hours, to yield compound (e2).

By reacting compound (e2) or a salt thereof with an amine ($R^8R^9NH$) in a nearly equimolar amount, compound (e3) of the present invention or a salt thereof is produced. This reaction is carried out in an appropriate inert solvent. The appropriate solvent is exemplified by amides such as dimethylformamide and dimethylacetamide, nitriles such as acetonitrile, alcohols such as ethanol, ethers such as dimethoxyethane, tetrahydrofuran, dioxane and dimethoxyethane, halogenated hydrocarbons such as dichloromethane, nitrites such as acetonitrile, ketones such as acetone, and esters such as ethyl acetate. This reaction is carried out in the presence of a non-nucleophilic base. The base is exemplified by tertiary organic amines (e.g., triethylamine, trimethylamine, diisopropylethylamine, N-methylmorpholine). Reaction temperature is normally about 10 to 100° C. Reaction time is about 1 to 10 hours. Preferably, this reaction is carried out during stirring. Compound (e3) can be thus produced.

Production Method 3

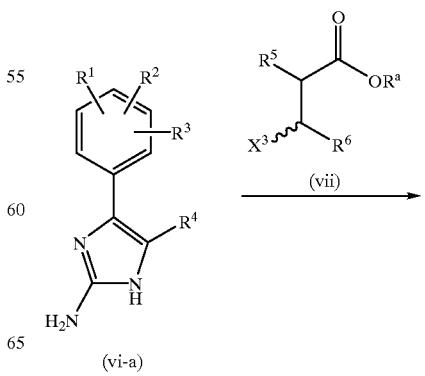

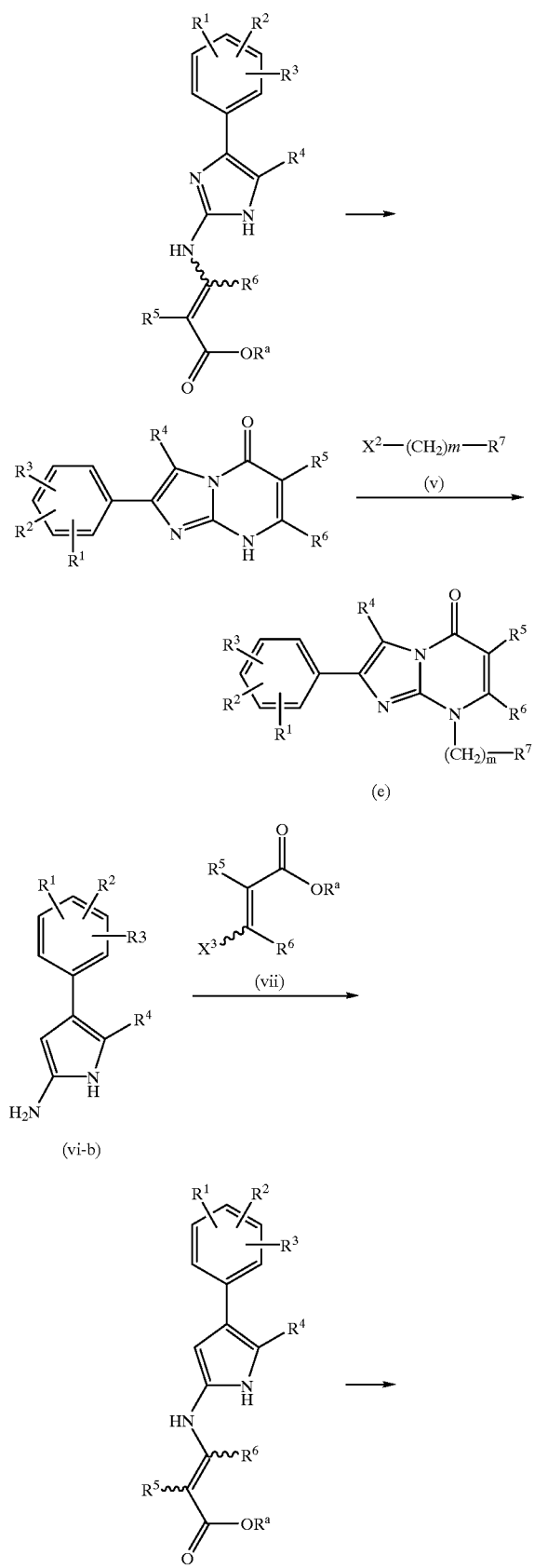

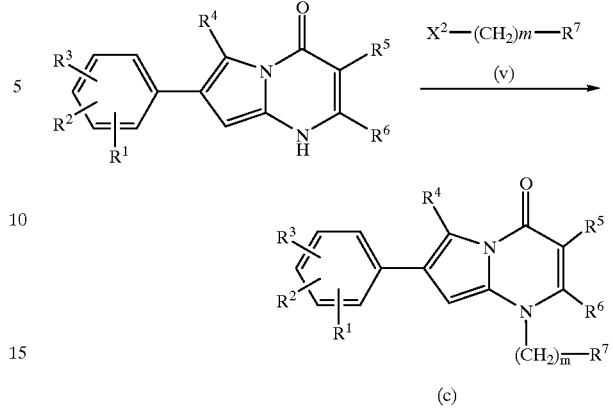

(c)

wherein $R^a$ represents a $C_{1-6}$ alkyl group; the other symbols have the same definitions as those given above In compound (I), compound (e) or (c) or a salt thereof can be produced by reacting 2-aminoimidazole derivative (vi-a) or 2-aminopyrrole derivative (vi-b) or a salt thereof with acrylic acid compound (vii) such as an ethoxymethylenecarboxylic acid derivative, then reacting with compound (v).

In this reaction, acrylic acid compound (vii) is used at 1 to 3 mol per mol of compound (vi-a) or (vi-b) or a salt thereof. The reaction is carried out in the absence of a solvent or in an appropriate inert solvent. The appropriate solvent is exemplified by ethers such as ethyl ether, dioxane, dimethoxyethane and tetrahydrofuran, aromatic hydrocarbons such as benzene and toluene, amides such as dimethylformamide and dimethylacetamide, and alcohols such as methanol and ethanol. This reaction is also carried out in the presence of a base. The base is exemplified by inorganic bases such as sodium carbonate, sodium hydrogen carbonate, potassium carbonate, potassium hydrogen carbonate, sodium hydroxide, potassium hydroxide and thallium hydroxide, and organic bases such as triethylamine. Reaction temperature is normally about 0 to 150° C., preferably about 15 to 25° C. Reaction time is about 1 to 12 hours. To produce the desired condensed ring compound, there may be added an additional process wherein the adduct between 2-aminoimidazole derivative (vi-a) or 2-aminopyrrole derivative (vi-b) or a salt thereof and acrylic acid compound (vii) is once isolated and reacted with compound (v) in an appropriate inert solvent. The appropriate solvent is exemplified by polyphosphoric acid (PPA), polyphosphoric acid ester (PPE), diphenyl ether, etc.

Compounds (e) and (c) thus produced can be subjected to alkylation or amino group introducing reaction shown for the above-described production methods, production methods 1 and 2.

Production Method 4-1

Compounds wherein $R^5$ is a carboxylic acid ester:

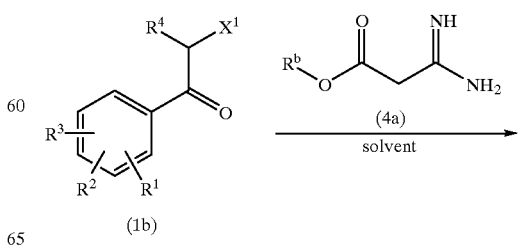

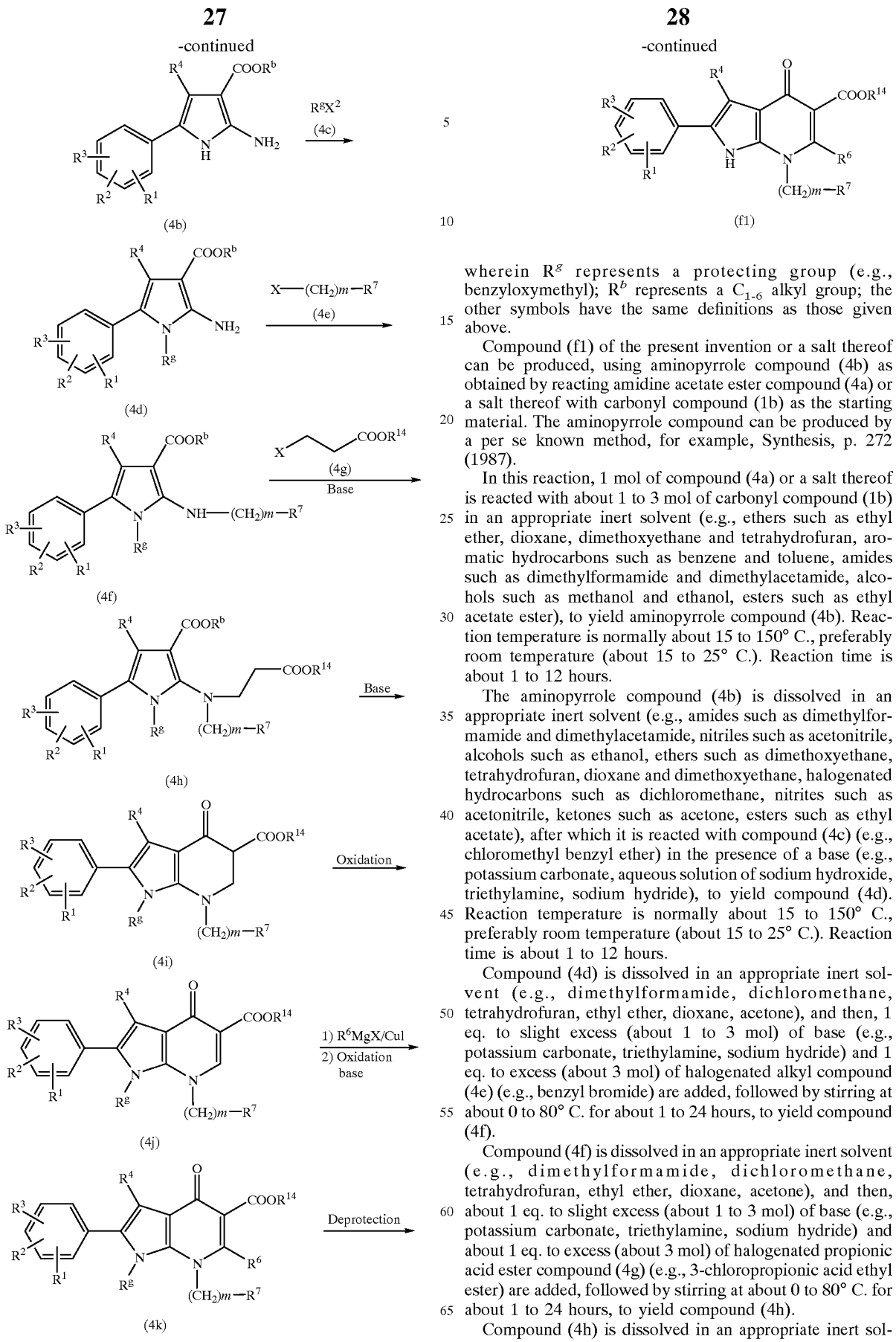

wherein $R^g$ represents a protecting group (e.g., benzyloxymethyl); $R^b$ represents a $C_{1-6}$ alkyl group; the other symbols have the same definitions as those given above.

Compound (f1) of the present invention or a salt thereof can be produced, using aminopyrrole compound (4b) as obtained by reacting amidine acetate ester compound (4a) or a salt thereof with carbonyl compound (1b) as the starting material. The aminopyrrole compound can be produced by a per se known method, for example, Synthesis, p. 272 (1987).

In this reaction, 1 mol of compound (4a) or a salt thereof is reacted with about 1 to 3 mol of carbonyl compound (1b) in an appropriate inert solvent (e.g., ethers such as ethyl ether, dioxane, dimethoxyethane and tetrahydrofuran, aromatic hydrocarbons such as benzene and toluene, amides such as dimethylformamide and dimethylacetamide, alcohols such as methanol and ethanol, esters such as ethyl acetate ester), to yield aminopyrrole compound (4b). Reaction temperature is normally about 15 to 150° C., preferably room temperature (about 15 to 25° C.). Reaction time is about 1 to 12 hours.

The aminopyrrole compound (4b) is dissolved in an appropriate inert solvent (e.g., amides such as dimethylformamide and dimethylacetamide, nitriles such as acetonitrile, alcohols such as ethanol, ethers such as dimethoxyethane, tetrahydrofuran, dioxane and dimethoxyethane, halogenated hydrocarbons such as dichloromethane, nitrites such as acetonitrile, ketones such as acetone, esters such as ethyl acetate), after which it is reacted with compound (4c) (e.g., chloromethyl benzyl ether) in the presence of a base (e.g., potassium carbonate, aqueous solution of sodium hydroxide, triethylamine, sodium hydride), to yield compound (4d). Reaction temperature is normally about 15 to 150° C., preferably room temperature (about 15 to 25° C.). Reaction time is about 1 to 12 hours.

Compound (4d) is dissolved in an appropriate inert solvent (e.g., dimethylformamide, dichloromethane, tetrahydrofuran, ethyl ether, dioxane, acetone), and then, 1 eq. to slight excess (about 1 to 3 mol) of base (e.g., potassium carbonate, triethylamine, sodium hydride) and 1 eq. to excess (about 3 mol) of halogenated alkyl compound (4e) (e.g., benzyl bromide) are added, followed by stirring at about 0 to 80° C. for about 1 to 24 hours, to yield compound (4f).

Compound (4f) is dissolved in an appropriate inert solvent (e.g., dimethylformamide, dichloromethane, tetrahydrofuran, ethyl ether, dioxane, acetone), and then, about 1 eq. to slight excess (about 1 to 3 mol) of base (e.g., potassium carbonate, triethylamine, sodium hydride) and about 1 eq. to excess (about 3 mol) of halogenated propionic acid ester compound (4g) (e.g., 3-chloropropionic acid ethyl ester) are added, followed by stirring at about 0 to 80° C. for about 1 to 24 hours, to yield compound (4h).

Compound (4h) is dissolved in an appropriate inert solvent (e.g., dimethylformamide, dichloromethane, tetrahydrofuran, ethyl ether, dioxane, acetone), and then, about 1 eq. to slight excess (about 1 to 3 mol) of base (e.g., bistrimethylsilylamide sodium salt) is added, followed by stirring at about 0 to 80° C. for about 1 to 24 hours, to yield compound (4i).

Compound (4i) is dissolved in an appropriate inert solvent (e.g., ethanol, dimethylformamide, dichloromethane, tetrahydrofuran, dioxane, acetone), and then, about 1 eq. to slight excess (about 1 to 3 mol) of base (e.g., potassium acetate, triethylamine, sodium hydride) and 1 eq. to excess (about 3 to 5 mol) of oxidant (e.g., iodine, bromine) are added, followed by stirring at about 0 to 80° C. for about 1 to 12 hours, to yield compound (4j).

Compound (4j) is dissolved in an inert solvent (e.g., dichloromethane, tetrahydrofuran), and then, about 1 eq. to slight excess (about 1 to 3 mol) of copper iodide and 1 to 10 eq. of Grignard reagent $R^6MgX$ are added, followed by stirring at about 0 to 80° C. for about 1 to 12 hours, to yield a 1,4-adduct compound.

The adduct compound is dissolved in an inert solvent (e.g., tetrahydrofuran, dimethylformamide, dioxane, toluene, benzene), and then, about 1 eq. to slight excess (about 1 to 3 mol) of base (e.g., sodium hydroxide, sodium hydride) and 1 eq. to slight excess (about 1 to 3 mol) of oxidant (e.g., iodine, bromine) are added, followed by stirring at about 0 to 80° C. for about 1 to 12 hours, to yield compound (4k).

By subjecting the compound (4k) to a per se known deprotection (e.g., catalytic reduction), compound (f1) or a salt thereof can be produced.

Production Method 4-2

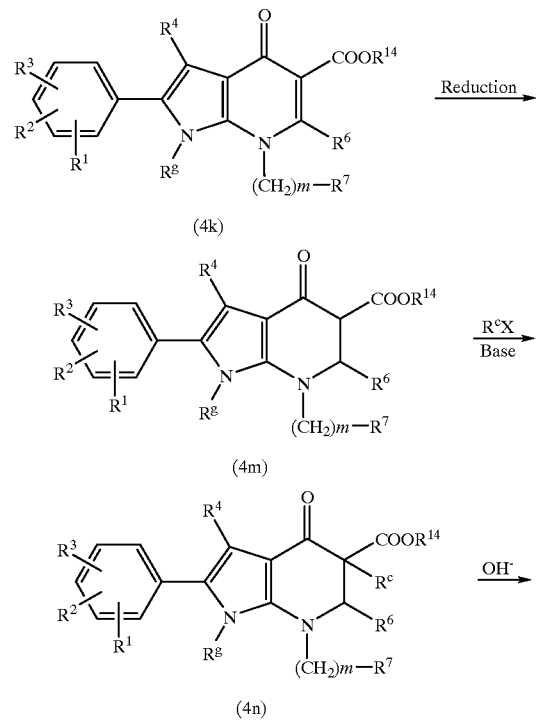

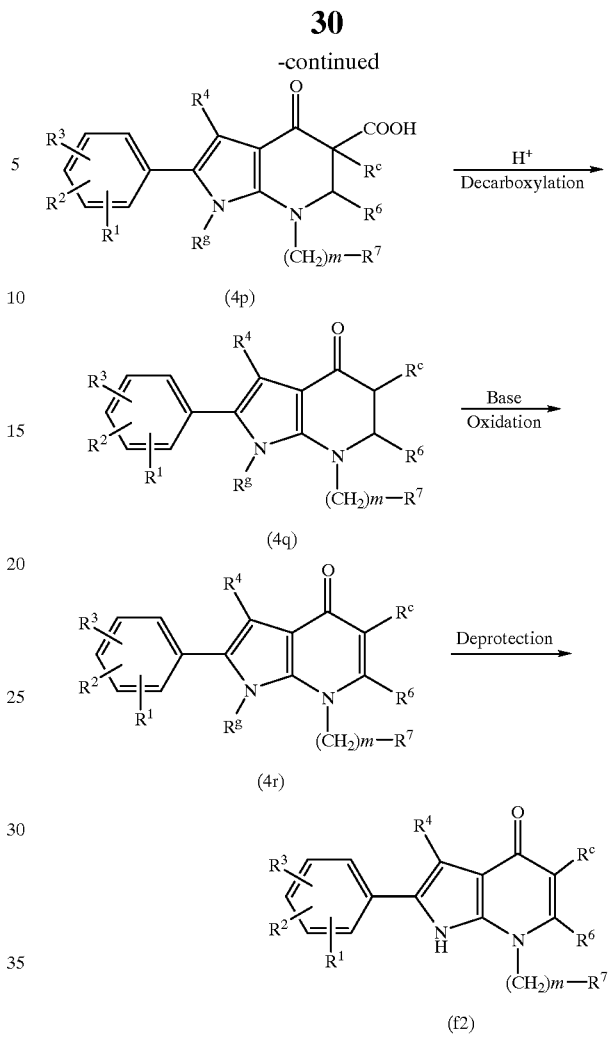

wherein $R^g$ represents a protecting group (e.g., benzyloxymethyl group); $R^c$ represents a group bound via a carbon atom but other than a carboxylic acid ester group (e.g., $C_{1-10}$ alkyl groups, $C_{1-20}$ acyl groups); the other symbols have the same definitions as those given above.

Compound (4k) is dissolved in an appropriate inert solvent (e.g., ethanol, methanol, dimethylformamide), and then a reducing agent (e.g., sodium borohydride, dibutylaluminum hydride) in excess is added, followed by stirring at about 0 to 60° C. for about 1 to 12 hours, to yield compound (4m).

Next, 1 mol of compound (4m) is reacted with about 1 to 3 mol of halogenated carbon compound $R^cX$ (e.g., halogenated $C_{1-20}$ acyl, halogenated $C_{1-10}$ alkyl) in an appropriate inert solvent (e.g., ethers such as ethyl ether, dioxane, dimethoxyethane and tetrahydrofuran, aromatic hydrocarbons such as benzene and toluene, amides such as dimethylformamide and dimethylacetamide, esters such as ethyl acetate ester) in the presence of 1 eq. to slight excess (about 1 to 3 mol) of base (e.g., potassium carbonate, triethylamine, sodium hydride) to yield compound (4n). Reaction temperature is normally about 15 to 150° C., preferably room temperature (about 15 to 25° C.). Reaction time is about 1 to 12 hours.

The compound (4n) is dissolved in an appropriate inert solvent (e.g., ethanol, tetrahydrofuran, ethyl ether, dioxane), and then, an aqueous solution of alkali (e.g., aqueous solution of potassium hydroxide, sodium hydroxide etc.) in excessis added, followed by stirring at about 15 to 150° C. for about 1 to 24 hours, to yield compound (4p).

The compound (4p) is dissolved in an appropriate inert solvent (e.g., tetrahydrofuran, dimethylformamide, dioxane, toluene, benzene), and then, an acid (e.g., hydrochloric acid, tosic acid, trifluoroacetic acid) is added, followed by stirring at about 15 to 150° C. for about 1 to 24 hours, to yield decarboxylated compound (4q).

The compound (4q) is dissolved in an appropriate inert solvent (e.g., tetrahydrofuran, dimethylformamide, dioxane, toluene, benzene), and then, about 1 eq. to slight excess of base (e.g., sodium hydroxide, sodium hydride) and 1 eq. to slight excess (about 1 to 3 mol) of oxidant (e.g., iodine, bromine), are added, followed by stirring at about 0 to 80° C. for about 1 to 12 hours, to yield compound (4r).

By subjecting the compound (4r) to a per se known deprotection (e.g., catalytic reduction), compound (f2) or a salt thereof can be produced.

Production Method 4-3

Compounds wherein $R^5$ is a group bound via an oxygen atom:

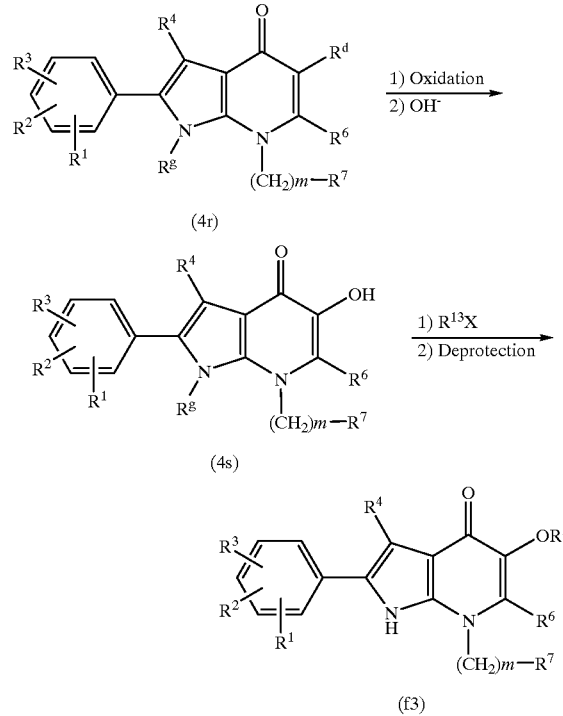

(4r)

(4s)

(f3)

wherein $R^g$ represents a protecting group (e.g., benzyloxymethyl); $R^d$ represents $C_{1-20}$ acyl; the other symbols have the same definitions as those given above Compound (4r) is dissolved in an appropriate inert solvent (e.g., dichloromethane, dimethylformamide), and then, about 1 eq. to slight excess (about 1 to 3 mol) of oxidant (e.g., metachloroperbenzoic acid) is added, followed by stirring at about 0 to 100° C. for about 1 to 24 hours, to yield a rearrangement product. Thus obtained rearrangement product is dissolved in an appropriate inert solvent (e.g., tetrahydrofuran, ethanol, dimethylformamide), and then, great excess (about 3 to 5 mol) of aqueous solution of alkali (e.g., aqueous solution of potassium hydroxide, sodium hydroxide etc.) is added, followed by stirring at about 15 to 150° C. for about 1 to 12 hours, to yield compound (4s).

The compound (4s) is dissolved in an appropriate inert solvent (e.g., dichloromethane, tetrahydrofuran, dimethylformamide, dioxane, toluene, benzene), and then, about 1 eq. to slight excess (about 1 to 3 mol) of base (e.g., sodium hydride, potassium carbonate) and about 1 eq. to slight excess (about 1 to 3 mol) of halogenated compound $R^{13}X$ (e.g., halogenated $C_{1-20}$ acyl, halogenated $C_{1-20}$ alkylsulfonyl, halogenated $C_{1-15}$ alkyl) are added, followed by stirring at about 0 to 80° C. for about 1 to 24 hours, after which a per se known deprotection (e.g., catalytic reduction) is carried out, to yield compound (f3) or a salt thereof.

Production method 4-4

Compounds wherein $R^5$ is a $C_{6-14}$ aryl group:

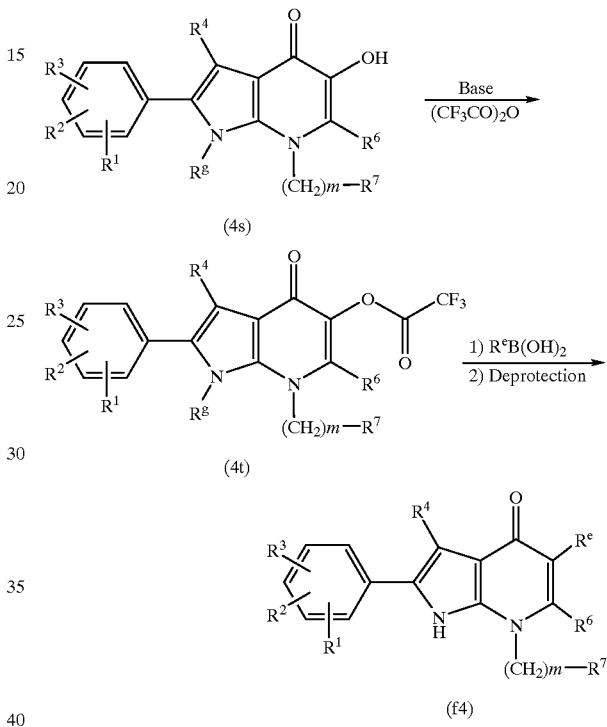

(4s)

(4t)

(f4)

wherein $R^g$ represents a protecting group (e.g., benzyloxymethyl); $R^e$ represents $C_{6-14}$ aryl; the other symbols have the same definitions as those given above Compound (4s) is dissolved in an appropriate inert solvent (e.g., tetrahydrofuran, dichloromethane, dimethylformamide), and then, about 1 eq. to slight excess (about 1 to 3 mol) of base (e.g., sodium hydride, potassium carbonate) and about 1 eq. to slight excess (about 1 to 3 mol) of trifluoroacetic anhydride are added, followed by stirring at about 0 to 80° C. for about 1 to 12 hours, to yield compound (4t).

Compound (4t) is dissolved in an appropriate inert solvent (e.g., tetrahydrofuran, dimethoxyethane), and then, about 1 to 10 eq. of aqueous solution of alkali (e.g., aqueous solution of potassium carbonate, sodium carbonate etc.), 1 eq. to slight excess (about 1 to 3 mol) of $R^eB(OH)_2$ (e.g., $C_{6-14}$ arylboric acid compounds such as phenylboric acid), and 0.1 to 0.5 eq. of tetrakistriphenylphosphine palladium [$(Ph_3P)_4$] are added, followed by stirring at about 15 to 150° C. for about 1 to 24 hours, after which a per se known deprotection (e.g., catalytic reduction) is carried out, to yield compound (f4) or a salt thereof.

Production Method 5

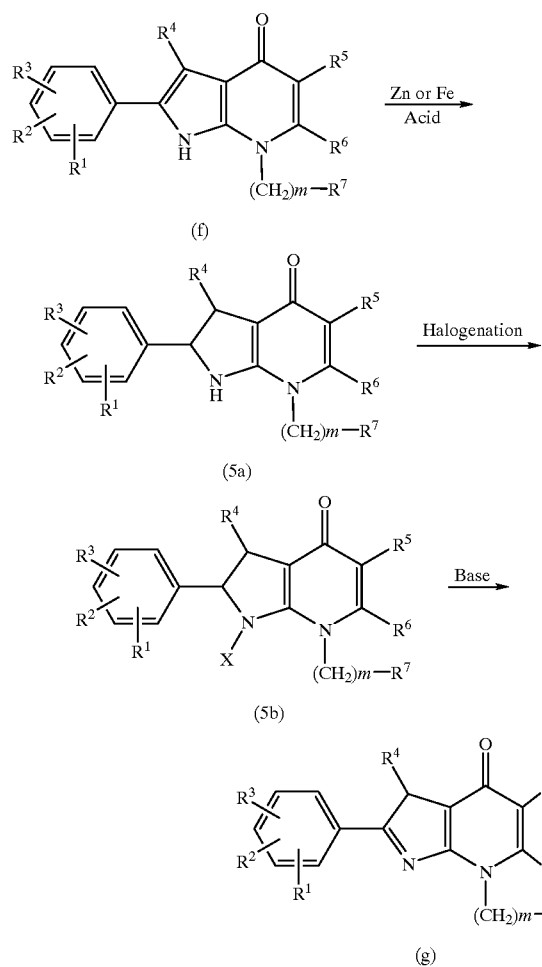

wherein X represents a halogen atom; the other symbols have the same definitions as those given above Compound (g) of the present invention or a salt thereof can be produced, using compound (f) or a salt thereof as the starting material.

In this reaction, 1 mol of compound (f) or a salt thereof is reacted with about 1 to 10 mol of zinc or iron and about 1 to 10 mol of a strong acid (e.g., hydrochloric acid, sulfuric acid) in an appropriate inert solvent (e.g., organic acids such as acetic acid, alcohols such as methanol and ethanol). Reaction temperature is normally about 15 to 150° C., preferably room temperature (about 15 to 25° C.). Reaction time is about 1 to 12 hours. Compound (5a) obtained is dissolved in an appropriate inert solvent (e.g., dimethylformamide, dichloromethane, tetrahydrofuran, ethyl ether, dioxane, acetone), and then, a halogenating agent (e.g., sodium hypochlorite, t-butyl hypochlorite, trichloroisocyanuric acid) is added, followed by stirring at about 15 to 150° C. Compound (5b) obtained is dissolved in an appropriate inert solvent (e.g., dimethylformamide, dichloromethane, tetrahydrofuran, ethyl ether, dioxane, acetone, ethanol), and then, about 1 eq. to slight excess (about 1 to 3 mol) of base (e.g., potassium carbonate, triethylamine, sodium hydride) is added, followed by stirring at about 0 to 80° C., to yield compound (g) or a salt thereof.

Production Method 6

Other methods:

Substituents in groups in the compound of the present invention can be converted to other substituents by per se known methods in common use. Examples of this method are given below.

(i) The nitro group as a substituent can be converted to the amino group. For example, the starting compound is dissolved in an appropriate solvent (e.g., methanol, ethanol), after which (a) palladium-carbon is added and a reaction is carried out in a hydrogen stream at about 15 to 25° C. for 1 to 12 hours, or (b) iron powder and hydrochloric acid are added to the above solution and a reaction is carried out at about 15 to 25° C. for 1 to 12 hours.

(ii) The amino group as a substituent can be converted to an acylated amino group. For example, the starting compound is dissolved in an appropriate solvent (e.g., tetrahydrofuran, dimethyl sulfoxide), and then, potassium carbonate and the bases pyridine and triethylamine are added, then, an acid anhydride or an acid halide is added. The mixture is reacted during stirring at about 15 to 25° C. for 1 to 10 hours.

(iii) A compound having the amino group can be converted to an alkenylamino compound. For example, the starting compound is dissolved in an appropriate solvent (e.g., acetic acid, dimethylformamide, dichloromethane, tetrahydrofuran, dioxane, acetonitrile), and, a diazotizing agent (e.g., sodium nitrate, isoamyl nitrate) is added, and then a palladium catalyst [e.g., bis(dibenzylideneacetone) palladium)] and 1 eq. to slight excess of alkenyl derivative are added and a reaction is carried out at about 15 to 80° C. for 1 to 12 hours.

(iv) A carbon atom can be introduced to the amino group. For example, the starting compound is dissolved in an appropriate solvent (e.g., acetic acid, dimethylformamide, dichloromethane, tetrahydrofuran, dioxane), and then, an acrylic acid derivative or an oxirane derivative (e.g., epoxide compounds) is added and a reaction is carried out during stirring at 0 to 80° C. for 6 to 24 hours.

(v) The formyl group as a substituent can be converted to the methyl group. For example, the starting compound is dissolved in an appropriate solvent (e.g., tetrahydrofuran), and then, an organic borane derivative (e.g., dimethyl sulfide borane) is added and a reaction is carried out during refluxing at about 15 to 80° C. for several hours (e.g., 1 to 3 hours).

(vi) From the methoxy, another alkoxy can be produced. For example, the starting compound is dissolved in an appropriate solvent (e.g., dichloromethane), and then, 1 eq. to excess of Lewis acid (e.g., aluminum chloride) and a thiol compound or a sulfide compound (e.g., dimethyl sulfide) are added and a reaction is carried out at about 0 to 20° C. for 1 to 10 hours. The hydroxy obtained is then dissolved in an appropriate solvent (e.g., dimethylformamide), and then, a base (e.g., sodium hydroxide, potassium carbonate) and an alkyl halide are added and a reaction is carried out at about 15 to 25° C. for 1 to 12 hours.

(vii) From the methoxy, the acyloxy can be produced. For example, the starting compound is dissolved in an appropriate solvent (e.g., dichloromethane), and then, 1 eq. to excess of Lewis acid (e.g., aluminum chloride) and a thiol compound or a sulfide compound (e.g., dimethyl sulfide) are added and a reaction is carried out at about 0 to 20° C. for 1 to 10 hours. The hydroxy obtained is then dissolved in an appropriate solvent (e.g., dimethylformamide), and then a base (e.g., sodium hydroxide, potassium carbonate) and an acyl halide are added and a reaction is carried out at about 15 to 25° C. for 1 to 12 hours.

(viii) The methoxy can be converted to an alkyne derivative. For example, the starting compound is dissolved in an appropriate solvent (e.g., dichloromethane), and then, 1 eq. to excess of Lewis acid (e.g., aluminum chloride) and a thiol compound or a sulfide compound (e.g., dimethyl sulfide) are added and a reaction is carried out at about 0 to 20° C. for 1 to 10 hours. The hydroxy obtained is then dissolved in an appropriate solvent (e.g., dimethylformamide), and then, a base (e.g., pyridine, triethylamine) and trifluoromethanesulfonic anhydride are added and a reaction is carried out at about 15 to 25° C. for 1 to 12 hours, to yield a triflate derivative. The triflate derivative obtained is then dissolved in an appropriate solvent (e.g., piperidine, pyrrolidine), and then, an alkyne derivative (e.g., propargyl alcohol, 3-butyn-1-ol) and a palladium compound as a catalyst [e.g., tetrakis (triphenylphosphine)palladium (0-valency) are added and a reaction is carried out during refluxing for 1 to 6 hours.

(ix) An alkylthio compound can be converted to an alkylsulfinyl compound or an alkylsulfonyl compound. For example, the starting compound is reacted with an oxidant (e.g., metachloroperbenzoic acid) in an appropriate solvent (e.g., dichloromethane). Provided that superheating or the antioxidant is used in excess, an alkylsulfonyl compound is obtained.

(x) The hydroxy group in the molecule can be substituted by various groups. The reaction is carried out in an appropriate solvent [e.g., dimethylformamide (DMF), acetonitrile, acetone], in the presence of a halide [e.g., alkyl halides (e.g., propyl iodide, isobutyl iodide, ethyl bromoacetate), aralkyl halides (e.g., benzyl chloride)], by stirring the mixture at 0 to 40° C. for 2 to 18 hours. For example, when ethyl bromoacetate is used, the acetic acid ester obtained is reacted at about 15 to 25° C. for 2 to 12 hours, using an appropriate solvent and a base (e.g., 1 N NaOH in ethyl alcohol). The acetic acid compound is dissolved in an appropriate solvent [e.g., tetrahydrofuran (THF)], and then, isobutyl chloroformate is added in the presence of an appropriate base (e.g., triethylamine) and a reaction is carried out at 0° C. for 1 to 4 hours. To the reaction solution, an appropriate amine compound (e.g., methylamine, propylamine, piperidine) is added, and a reaction is carried out at about 0 to 25° C. for 1 to 12 hours.

The above-described starting compound having the hydroxy group in the molecule can be produced by, for example, subjecting a compound having the alkoxy group in the molecule to acid hydrolysis. This acid hydrolysis is achieved by a commonly used method; for example, the starting compound is reacted in an appropriate solvent such as alcohols (e.g., methanol, ethanol) in the presence of 1 N hydrochloric acid at about 0 to 25° C. for 1 to 10 hours.

(xi) A compound having an alkanoyl-phenyl group can be produced by introducing an alkanoyl-phenyl group to a compound having a halogenated group. For introduction of an alkanoyl-phenyl group, a halogenated compound is first reacted in an appropriate solvent (e.g., carbon tetrachloride, chloroform) in the presence of N-bromosuccinimide and a catalytic amount (not more than 10 mol %) of 2,2'-azobis(isobutyronitrile) at 100 to 120° C. for 1 to 4 hours.

Introduction of an alkanoyl-phenyl group to the halogenated compound is carried out in an appropriate solvent such as dimethoxyethane (DME). To the solution, an alkanoyl-phenyl borate, a palladium compound [e.g., Pd(PPh$_3$)$_4$, Ph represents phenyl] and sodium carbonate (2 M, Na$_2$CO$_3$) are added. The reaction is carried out in an inert gas stream at about 15 to 120° C. for about 1 to 12 hours.

An alkanoyl-phenyl borate is produced by reacting an alkanoyl-phenyl bromide and a boric acid compound [e.g., (i-PrO)$_3$B, Pr represents propyl] in the presence of an appropriate base (e.g., BuLi, Bu represents butyl).

(xii) A compound having an alkyl-phenyl group can be produced by the same method as method (xi) above, except that an alkyl-phenyl borate is used in place of an alkanoyl-phenyl borate in the reaction.

(xiii) In the compound of the present invention, an incorporation of a sulfonamide group can be produced by halogenating the alkyl group in the starting compound, then subjecting the compound to a nucleophilic substitution reaction with a sulfonamide.

The halogenation is achieved by reacting the starting compound in an appropriate solvent (e.g., carbon tetrachloride) in the presence of N-bromosuccinimide or a catalytic amount of 2,2'-azobis(isobutyronitrile) at 100 to 120° C. for 1 to 4 hours. The nucleophilic substitution reaction is carried out, for example, in an appropriate solvent such as N,N-dimethylformamide (DMF) in the presence of n-hexane-washed sodium hydride and a sulfonamide derivative (e.g., methanesulfonamide, ethanesulfonamide, benzenesulfonamide) at 0 to 40° C. for 1 to 24 hours.

Introduction of other groups to the compound of the present invention can be achieved, using per se known methods.

Compound (I) of the present invention thus obtained may form a salt. The salt is preferably a physiologically acceptable acid addition salt. Such salts include, for example, salts with inorganic acids (e.g., hydrochloric acid, hydrobromic acid, nitric acid, sulfuric acid, phosphoric acid) and physiologically acceptable acid addition salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid). When compound (I) of the present invention has an acidic group such as —COOH, it may form a physiologically acceptable salt with an inorganic base (e.g., alkali metals such as sodium, potassium, calcium and magnesium, alkaline earth metals, ammonia) or an organic base (e.g., trimethylamine, triethylamine, pyridine, picoline, ethanolamine, diethanolamine, triethanolamine, dicyclohexylamine, N,N'-dibenzylethylenediamine).

Also, the compound of the present invention or a salt thereof may be a hydrate or a non-hydrate. The hydrate is exemplified by monohydrate, sesquihydrate and dehydrate.

Compound (I) of the present invention or a salt thereof thus obtained may be isolated and purified by ordinary means of separation such as recrystallization, distillation and chromatography, etc. When the compound of the present invention is obtained in free form, it can be converted to a salt by per se known methods or analogous thereto. When the compound of the present invention is obtained in salt form, it can be converted to the free form or another salt by per se known methods or analogous thereto.

Compound (I) of the present invention or a salt thereof may has asymmetric carbon. When it is obtained as a mixture (racemate) of optically active configurations, it can be fractionated into the respective optically active configurations by ordinary means of optical resolution.

Compound (I) or its salt of the present invention (hereinafter also referred to as "compound of the present invention") possesses excellent GnRH-antagonizing activity and low toxicity. In addition, it is excellent in oral absorbability, action sustainability, stability and pharmacokinetics. Furthermore, it can be easily produced. The compound of the present invention can therefore be safely used in a mammal (e.g., human, monkey, bovine, horse, dog, cat, rabbit, rat, mouse) for preventing and/or treating diseases depending on male or female hormones, diseases due to excess of these hormone, etc., by suppressing gonadotropin secretion by its GnRH receptor-antagonizing action to control blood sex hormone concentrations.

For example, the compound of the present invention is useful for preventing and/or treating sex hormone-dependent cancers (e.g., prostatic cancer, uterine cancer, breast cancer, pituitary tumor), prostatic hypertrophy, hysteromyoma, endometriosis, precocious puberty, amenorrhea, premenstrual syndrome, multilocular ovary syndrome, pimples etc. The compound of the present invention is also useful for the regulation of reproduction in males or females (e.g., pregnancy regulators, menstruation cycle regulators). The compound of the present invention also be used as a male or female contraceptive, or as a female ovulation inducer. Based on its rebound effect after withdrawal, the compound of the present invention can be used to treat infertility.

In addition, the compound of the present invention is useful for regulation of animal estrous, improvement of meat quality and promotion of animal growth in the field of animal husbandry. The compound of the present invention is also useful as a fish spawning promoter.

Although the compound of the present invention can be used alone, it is effective to use it in combination with a steroidal or non-steroidal anti-androgen agent or anti-estrogen agent. The compound of the present invention can also be used to suppress the transient rise in blood testosterone concentration (flare phenomenon) observed in administration of a super-agonist such as leuprorelin acetate. The compound of the present invention may be used with a chemotherapeutic agent for cancer. A preferred example of such combination is the compound of the present invention in combination with chemotherapeutic agents such as ifosfamide, UTF, adriamycin, peplomycin and cisplatin for prostatic cancer. For breast cancer, the compound of the present invention can be used with chemotherapeutic agents such as cyclophosphamide, 5-FU, UFT, methotrexate, adriamycin, mitomycin C and mitocantrone.

When the compound of the present invention is used as a prophylactic and/or therapeutic agent for the above-mentioned diseases or used in the filed of animal husbandry or fishery, it can be administered orally or non-orally, as formulated with a pharmaceutically acceptable carrier, normally in the form of solid preparations such as tablets, capsules, granules and powders for oral administration, or in the form of intravenous, subcutaneous, intramuscular or other injections, suppositories or sublingual tablets for non-oral administration. It may also be sublingually, subcutaneously, intramuscularly or otherwise administered in the form of sustained-release preparations of sublingual tablets, microcapsules etc. Depending on symptom severity, subject age, sex and weight, duration and intervals of administration, kind of active ingredient etc., daily dose is not subject to limitation. For use in the treatment of the above-described sex hormone-dependent cancers (e.g., prostatic cancer, uterine cancer, breast cancer, pituitary tumor), prostatic hypertrophy, hysteromyoma, endometriosis, precocious puberty etc., daily dose is normally about 0.1 to 30 mg, preferably about 0.1 to 10 mg, and more preferably 0.1 to 5 mg, per kg weight of mammal, normally in 1 to 4 divided dosages.

The above doses are applicable to the use of the compound of the present invention in the filed of animal husbandry or fishery. Daily dose is about 0.01 to 10 mg, preferably about 0.05 to 5 mg, per kg weight of subject organism, normally in 1 to 3 divided dosages.

Pharmaceutically acceptable carriers are various organic or inorganic carrier substances in common use as pharmaceutical materials, including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary.

Preferable excipients include, for example, lactose, sucrose, D-mannitol, starch, crystalline cellulose and light silicic anhydride. Preferable lubricants include, for example, magnesium stearate, calcium stearate, talc and colloidal silica. Preferable binders include, for example, crystalline cellulose, sucrose, D-mannitol, dextrin, hydroxypropyl cellulose, hydroxypropylmethyl cellulose and polyvinylpyrrolidone. Preferable disintegrants include, for example, starch, carboxymethyl cellulose, carboxymethyl cellulose calcium, crosslinked carmellose sodium and carboxymethyl starch sodium. Preferable solvents include, for example, water for injection, alcohol, propylene glycol, macrogol, sesame oil and corn oil. Preferable dissolution aids include, for example, polyethylene glycol, propylene glycol, D-mannitol, benzyl benzoate, ethanol, trisaminomethane, cholesterol, triethanolamine, sodium carbonate and sodium citrate. Preferable suspending agents include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include, for example, sodium chloride, glycerol and D-mannitol. Preferable buffers include, for example, buffer solutions of phosphates, acetates, carbonates, citrates etc. Preferable soothing agents include, for example, benzyl alcohol. Preferable preservatives include, for example, paraoxybenzoic acid esters, chlorobutanol, benzyl alcohol, phenethyl alcohol, dehydroacetic acid and sorbic acid. Preferable antioxidants include, for example, sulfites and ascorbic acid.

By adding a suspending agent, a dissolution aid, a stabilizer, an isotonizing agent, a preservative etc., the compound of the present invention can be prepared as an intravenous, subcutaneous or intramuscular injection by a commonly known method. In such cases, the compound of the present invention can be freeze-dried as necessary by a commonly known method. In administration to humans, for example, the compound of the present invention can be safely administered orally or non-orally as such or as a pharmaceutical composition prepared by mixing it with a pharmacologically acceptable carrier, excipient and diluent selected as appropriate.

Such pharmaceutical compositions include oral preparations (e.g., powders, granules, capsules, tablets), injections, drip infusions, external preparations (e.g., nasal preparations, transdermal preparations) and suppositories (e.g., rectal suppositories, vaginal suppositories).

These preparations can be produced by commonly known methods in common use for pharmaceutical making processes.

An injection can be produced by, for example, preparing the compound of the present invention as an aqueousinjection along with a dispersing agent (e.g., Tween 80, produced by Atlas Powder Company, USA, HCO 60, produced by Nikko Chemicals Co., Ltd., polyethylene glycol, carboxymethyl cellulose, sodium alginate), a preservative (e.g., methyl paraben, propyl paraben, benzyl alcohol), an isotonizing agent (e.g., sodium chloride, mannitol, sorbitol, glucose) and other additives, or as an oily injection in solution, suspension or emulsion in a vegetable oil such as olive oil, sesame oil, cottonseed oil or corn oil, propylene glycol or the like.

An oral preparation can be produced by shaping the compound of the present invention by a commonly known method after addition of an excipient (e.g., lactose, sucrose, starch), a disintegrant (e.g., starch, calcium carbonate), a binder (e.g., starch, gum arabic, carboxymethyl cellulose, polyvinylpyrrolidone, hydroxypropyl cellulose), a lubricant (e.g., talc, magnesium stearate, polyethylene glycol 6000) and other additives, and, where necessary, coating the shaped product for the purpose of taste masking, enteric dissolution or sustained release by a commonly known method. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (produced by Rohm Company, Germany, methacrylic acid/acrylic acid copolymer) and dyes (e.g., iron oxide, titanium dioxide). For an enteric preparation, an intermediate phase may be provided between the enteric phase and the drug-containing phase for the purpose of separation of the two phases by a commonly known method.

An external preparation can be produced by compounding the compound of the present invention as a solid, semi-solid or liquid composition by a commonly known method. Such a solid composition is produced by, for example, powdering the compound of the present invention as such or in mixture with an excipient (e.g., glycol, mannitol, starch, microcrystalline cellulose), a thickening agent (e.g., natural rubber, cellulose derivative, acrylic acid polymer) and other additives. Such a liquid composition is produced by preparing the compound of the present invention as an oily or aqueous suspension in almost the same manner as with the injection. The semi-solid composition is preferably an aqueous or oily gel, or an ointment. All these compositions may contain pH regulators (e.g., carbonic acid, phosphoric acid, citric acid, hydrochloric acid, sodium hydroxide), preservatives (e.g., paraoxybenzoic acid esters, chlorobutanol, benzalkonium chloride) and other additives.

A suppository is produced by preparing the compound of the present invention as an oily or aqueous solid, semi-solid or liquid composition by a commonly known method. Useful oily bases for such compositions include glycerides of higher fatty acids (e.g., cacao fat, uitepsols, produced by Dynamite Nobel Company, Germany), moderate fatty acids (e.g., MIGLYOL, produced by Dynamite Nobel Company, Germany), and vegetable oils (e.g., sesame oil, soybean oil, cottonseed oil). Aqueous bases include, for example, polyethylene glycols and propylene glycol. Bases for aqueous gels include, for example, natural rubbers, cellulose derivatives, vinyl polymers and acrylic acid polymers.

BEST MODE FOR CARRYING OUT THE INVENTION

The present invention is hereinafter described in more detail by means of, but is not limited to, the following reference examples, examples, experimental example and preparation examples.

$^1$H-NMR spectra are determined with tetramethylsilane as the internal standard, using the LAMBDA 300 (300 MHz) spectrometer (produced by JEOL, Ltd.) or the Bruker AM500 (500 MHz) spectrometer (produced by Bruker); all δ values are shown in ppm.

The symbols used herein have the following definitions:

s: singlet d: doublet t: triplet dt: double triplet m: multiplet q: quartet br: broad Me: methyl Et: ethyl Ph: phenyl Bz: benzyl Boc: t-Butoxycarbonyl THF: tetrahydrofuran DMF: dimethylformamide The term "at room temperature" indicates the range from about 15 to 25° C., but is not to be construed as strictly limitative.

Reference Example 1

Production of 2-amino-4-hydroxypyrimidine-5-carboxylic acid ethyl ester

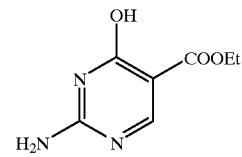

Guanidine carbonate (18.0 g, 200 mmol) is dissolved in ethanol (300 ml), and then sodium alcoholate (13.6 g) and ethoxymethylenemalonic acid diethyl ester (43.2 g, 200 mmol) are added at room temperature. After stirring at room temperature for 4 days, the mixture is concentrated to dryness under reduced pressure. To the residue obtained, water (500 ml) is added and neutralized with hydrochloric acid, and then the crystal precipitated is collected by filtration and recrystallized, to yield a white crystal (30.5 g, 83%).

mp 280° C. (lit. 285° C.: Journal of the Indian Chemical Society, 1925, Vol. 2, pp. 61–70)

$^1$H-NMR (CDCl$_3$) δ:1.25 (3H, t), 4.14 (2H, q), 6.0–7.5 (2H, br s), 8.35 (1H, s), 11.12 (1H, br s).

Reference Example 2

In the same manner as Reference Example 1, with guanidine carbonate as the starting material, and using 2-benzylacetoacetic acid ethyl ester, acetoacetic acid ethyl ester, 2-ethoxymethylenephenylacetic acid ethyl ester, 2-methoxy-2-formylacetic acid ethyl ester, 2-butoxy-2-formylacetic acid ethyl ester, or 2-benzyloxy-2-formylacetic acid ethyl ester, in place of ethoxymethylenemalonic acid diethyl ester, the 5,6-substitutional 2-amino-4-hydroxypyrimidine derivatives shown in Table 1 are synthesized.

TABLE 1

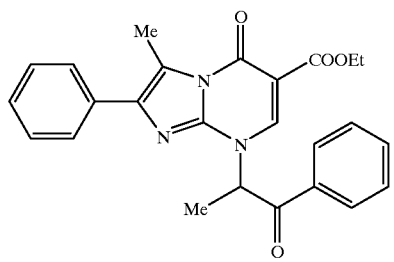

| Compd. No. | $R^5$ | $R^6$ | yield (%) | mp (° C.) |
|---|---|---|---|---|
| 1 | Bz | Me | 72 | >250 (dc.) |
| 2 | H | Me | 84 | >250 (dc.) |
| 3 | Ph | H | 29 | >250 (dc.) |
| 4 | methoxy | H | 65 | 266–267 |
| 5 | butoxy | H | 62 | 236–239 |
| 6 | benzyloxy | H | 65 | 245–246 |

[4,5,6: J.Am.Chem.Soc., vol. 73, p.3753 (1951)]

Reference Example 3

Production of 5,8-dihydro-3-methyl-5-oxo-8-(1-oxo-1-phenyl-2-propyl)-2-phenylimidazo[1,2-a]pyrimidine-6-carboxylic acid ethyl ester

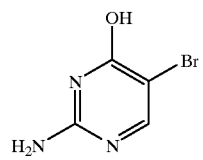

The pyrimidine compound obtained in Reference Example 1 (10.0 g. 54.6 mmol) is dissolved in dimethylformamide (300 ml), and then potassium carbonate (18.9 g, 136.5 mmol), potassium iodide (9.10 g, 54.6 mol) and 2-bromopropiophenone (29.1 g, 136.5 mmol) are added. After stirring at room temperature for 4 days, the mixture is concentrated to dryness under reduced pressure. The residue obtained is dispensed to water (300 ml) and chloroform (300 ml). After extraction with chloroform, the water layer is combined with the organic layer, followed by drying with magnesium sulfate and subsequent concentration under reduced pressure. The residue obtained is purified with silica gel to yield a white crystal (11.3 g), which is then recrystallized from ethyl acetate ester and hexane to yield a white needle crystal (8.6 g, 371).

mp 177–178° C.

$^1$H-NMR (CDCl$_3$) δ: 1.42 (3H, t), 1.82 (3H, d), 2.90 (3H, s), 4.41 (2H, q), 6.82 (1H, q), 7.3–7.4 (3H, m), 7.5–7.7 (5H, m), 8.13 (2H, d), 8.54 (1H, s).

Reference Example 4

Using the compounds obtained in Reference Example 2, and in the same manner as Reference Example 3, with 2-bromo-1-(4-acetylamino)phenylpropan-1-one, 2-bromo-1-(4-methoxy)phenylpropan-1-one and 2-bromo-1-(4-acetoxy)phenylpropan-1-one in place of 2-bromopropiophenone, the derivatives shown in Table 2 are synthesized.

TABLE 2

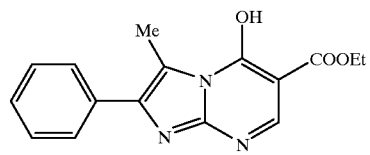

| Compd. No. | $R^1, R^{1a}$ | $R^5$ | yield (%) | mp (° C.) |
|---|---|---|---|---|
| 1 | 4-acetylamino | Ph | 25 | amorphous |
| 2 | 4-methoxy | ethoxy-carbonyl | 30 | 166–167 (free) |
| 3 | 4-acetoxy | bromo | 30 | amorphous |

Reference Example 5

Production of 2-amino-5-4-hydroxypyrimidine

To a solution of isocytosine(1.04 g, 9.36 mmol) in acetic acid(25 ml) are added dropwise bromine(0.51 ml, 9.83 mmol) at room temperature. After the addition is completed, the reaction mixture is stirred for 1 hour at this temperature, successively concentrated under reduced pressure to give the residue, which is washed with ethyl ether, dried to afford white powders(2.49 g, 98%).

EXAMPLE 1

Production of 5-hydroxy-3-methyl-2-phenylimidazo[1,2-a]pyrimidine -6-carboxylic acid ethyl ester To an acetic acid solution (30 ml) of the compound obtained in Reference Example 3 (0.43 g, 1.0 mmol), zinc powder (1.05 g, 16 mmol) is added, followed by stirring under heating at 80° C. for 2 hours. The reaction mixture is filtered through Celite to remove the zinc, and then the resulting filtrate is concentrated under reduced pressure. The brown substance obtained is crystallized by the addition of water (100 ml). After filtration, the crystal is purified by recrystallization (chloroform-hexane-ether) to yield a brownish white needle crystal (0.26 g, 87%).

mp 220–225° C.

$^1$H-NMR (CDCl$_3$) δ: 1.41 (3H, t), 2.93 (3H, s), 4.36 (2H, q), 7.56 (5H, s), 8.53 (1H. s).

IR (KBr): 4426, 3448, 2984, 2368, 1721, 1543, 1456, 1373, 1344, 1292, 1209, 1131, 1091, 1023, 922, 853, 795, 768, 700, 669 cm$^{-1}$.

FAB-MS Calcd for C$_{16}$H$_{16}$N$_3$O$_3$ 298.11928, found 298.0681 Anal. Calcd for C$_{16}$H$_{15}$N$_3$O$_3$·0.8H$_2$O: C, 61.65; H, 5.37; N, 13.48. Found: C, 61.83; H, 4.99; N, 13.45.

EXAMPLE 2

In the same manner as Reference Example 3 (the method described in Example 2 also conducted as necessary), using the pyrimidine compounds shown in Reference Example 2 and 2-bromopropiophenone or various halogenoketone compounds, the imidazo[1,2-a]pyrimidine derivatives shown in Table 3 are synthesized.

TABLE 3

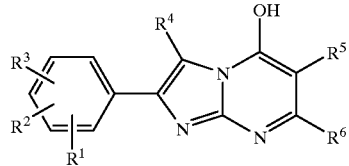

| Compd. No. | R$^1$, R$^2$, R$^3$ | R$^4$ | R$^5$ | R$^6$ | yd. (%) | mp (° C.) |
|---|---|---|---|---|---|---|
| 1 | H | Me | Bz | Me | | |
| 2 | 4-cyclopropylmethoxy | Me | Bz | Me | 30 | amorphous |
| 3 | 4-methoxy | Me | Bz | Me | | |
| 4 | 4-acetoxy | Me | Bz | Me | | |
| 5 | H | H | Bz | Me | | |
| 6 | H | H | ethoxycarbonyl | H | | |
| 7 | 4-cyclopropylmethoxy | H | Bz | Me | | |
| 8 | 4-cyclopropylmethoxy | H | H | Me | | |
| 9 | 4-cyclopropylmethoxy | Me | Ph | H | | |
| 10 | H | Me | Ph | H | | |
| 11 | 4-acetoxy | Me | Ph | H | | |
| 12 | H | Me | methoxy | H | | |
| 13 | 4-acetoxy | Me | methoxy | H | | |
| 14 | H | Me | butoxy | H | | |
| 15 | 4-acetoxy | Me | butoxy | H | | |
| 16 | H | Me | benzyloxy | H | | |
| 17 | 4-acetoxy | Me | benzyloxy | H | | |
| 18 | 4-cyclopropylmethoxy | Me | ethoxycarbonyl | H | | |
| 19 | 4-isobutyrylamino | Me | Bz | Me | 30 | amorphous |
| 20 | 4-acetoxy | Me | ethoxycarbonyl | H | 26 | 258–260 |
| 21 | 4-acetylamino | Me | Ph | H | 80 | amorphous |
| 22 | 4-acetylamino | Me | Bz | Me | 20 | amorphous |

TABLE 3-continued

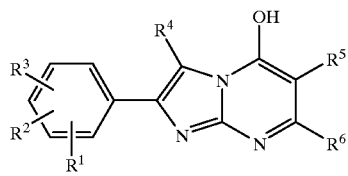

| Compd. No. | R$^1$, R$^2$, R$^3$ | R$^4$ | R$^5$ | R$^6$ | yd. (%) | mp (° C.) |
|---|---|---|---|---|---|---|
| 23 | 4-acetoxy | Me | bromo | H | 63 | >260 (dc.) |
| 24 | 4-methoxy | Me | ethoxycarbonyl | H | 43 | 245–247 |

EXAMPLE 3

Production of 8-(2,6-difluorobenzyl)-5,8-dihydro-3-methyl-5-oxo-2-phenylimidazo[1,2-a]pyrimidine-6-carboxylic acid ethyl ester

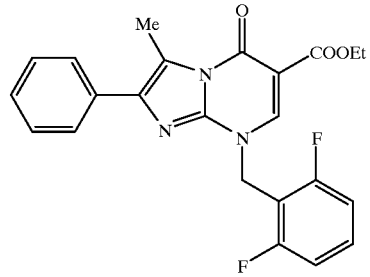

To a solution of the compound obtained in Example 1 (157 mg, 0.53 mmol) in DMF (15 ml), potassium carbonate (80 mg, 0.58 mmol), 2,6-difluorobenzyl chloride (103 mg, 0.64 mmol) and potassium iodide (44 mg, 0.26 mmol) are added, followed by stirring at about 15 to 25° C. for 1 hour and stirring under heating at 80° C. for 1 hour. The brownish white crystalline substance obtained by concentration under reduced pressure of the reaction mixture is dispensed to ethyl acetate (30 ml) and water (30 ml). The water layer is extracted with ethyl acetate (10 ml), and the organic layers are combined and dried over sodium sulfate, after which the solvent is distilled off under reduced pressure to yield a crude brownish white crystalline product (204 mg), which is then purified by flush column chromatography to yield a white crystal (146 mg, 65%).

$^1$H-NMR (CDCl$_3$) δ: 1.39 (3H, t), 2.91 (3H, s), 4.37 (2H, q), 5.51 (2H, s), 7.00 (2H, t), 7.3–7.5 (4H, m), 7.69 (2H, d), 8.37 (1H, s).

EXAMPLE 4

Using the compounds obtained in Example 2, and in the same manner as Example 3, the compounds shown in Table 4 below are produced.

TABLE 4

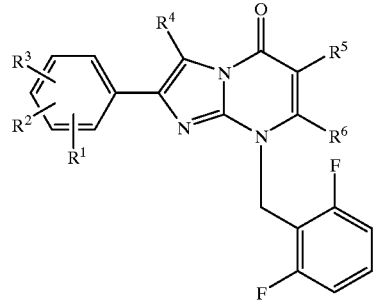

| Compd. No. | $R^1, R^2, R^3$ | $R^4$ | $R^5$ | $R^6$ | yd. (%) | mp (° C.) |
|---|---|---|---|---|---|---|
| 1 | H | Me | Bz | Me | | |
| 2 | 4-cyclo-propylmethoxy | Me | Bz | Me | 20 | 178–180 |
| 3 | 4-methoxy | Me | Bz | Me | | |
| 4 | 4-acetoxy | Me | Bz | Me | | |
| 5 | H | H | Bz | Me | | |
| 6 | H | H | ethoxy-carbonyl | H | | |
| 7 | 4-cyclo-propylmethoxy | H | Bz | Me | | |
| 8 | 4-cyclo-propylmethoxy | H | H | Me | | |
| 9 | 4-cyclo-propylmethoxy | Me | Ph | H | | |
| 10 | H | Me | Ph | H | | |
| 11 | 4-acetoxy | Me | Ph | H | | |
| 12 | H | Me | methoxy | H | | |
| 13 | 4-acetoxy | Me | methoxy | H | | |
| 14 | H | Me | butoxy | H | | |
| 15 | 4-acetoxy | Me | butoxy | H | | |
| 16 | H | Me | benzyloxy | H | | |
| 17 | 4-acetoxy | Me | benzyloxy | H | | |
| 18 | 4-cyclo-propylmethoxy | Me | ethoxy-carbonyl | H | | |
| 19 | 4-isobutyryl-amino | Me | Bz | Me | 10 | 179–180 |
| 20 | 4-acetoxy | Me | ethoxy-carbonyl | H | 67 | 181–182 |
| 21 | 4-acetylamino | Me | Ph | H | 73 | amorphous |
| 22 | 4-acetylamino | Me | Bz | Me | 20 | amorphous |
| 23 | 4-acetoxy | Me | bromo | H | 53 | 203-207 |
| 24 | 4-methoxy | Me | ethoxy-carbonyl | H | 74 | 195–197 |

EXAMPLE 5

Production of 8-(2,6-difluorobenzyl)-5,8-dihydro-3-methyl-2-(4-nitrophenyl)-5-oxoimidazo[1,2-a]pyrimidine-6-carboxylic acid ethyl ester

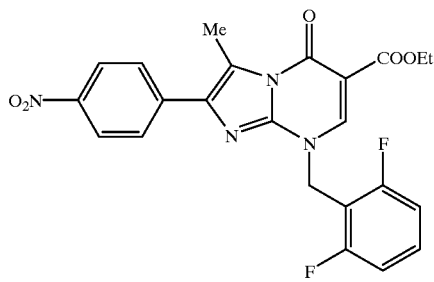

To a solution of the compound obtained in Example 3 (3.0 g, 7.0 mmol) in concentrated sulfuric acid. (30 ml), a solution of sodium nitrate (0.6 g, 7.0 mmol) in concentrated sulfuric acid (6 ml) is added drop by drop under ice cooling conditions over a 30-minute period, followed by stirring under ice cooling conditions for 4 hours. The reaction mixture is dispensed to water (500 ml) and chloroform (400 ml), and then the water layer is extracted with chloroform (200 ml), and the organic layers are combined and dried over sodium sulfate, after which the solvent is distilled off under reduced pressure to yield a crude yellow crystalline product, which is then purified by recrystallization (chloroform-ether) to yield a brown-yellow crystal (6, 2.6 g, 80%).

mp 219–221° C.

$^1$H-NMR (CDCl$_3$) δ: 1.40 (3H, t), 2.97 (3H, s), 4.38 (2H, q), 5.51 (2H, s), 7.02 (2H, t), 7.36–7.46 (1H, m), 7.87–8.31 (4H, q), 8.46 (1H, s).

IR (KBr): 3448, 3086, 2986, 2364, 1746, 1713, 1628, 1599, 1518, 1473, 1342, 1290, 1218, 1160, 1108, 1035, 907, 857, 789, 760, 710, 611, 580, 499 cm$^{-1}$.

FAB-MS m/e 469.1 (MH$^+$)

Anal. Calcd for $C_{23}H_{18}N_4O_5F_2$: C, 58.98; H, 3.87; N, 11.96. Found: C, 58.49; H, 3.79; N, 12.01.

EXAMPLE 6

Using the compounds obtained in Example 4, and in the same manner as Example 5, the compounds shown in Table 5 below are produced.

TABLE 5

| Compd. No. | $R^4$ | $R^5$ | $R^6$ |
|---|---|---|---|
| 1 | Me | Bz | Me |
| 2 | H | Bz | Me |
| 3 | H | ethoxycarbonyl | H |
| 4 | Me | Ph | H |
| 5 | Me | methoxy | H |
| 6 | Me | butoxy | H |
| 7 | Me | benzyloxy | H |

EXAMPLE 7

Production of 3-bromomethyl-8-(2,6-difluorobenzyl)-5,8-dihydro-2-(4-nitrophenyl)-5-oxoimidazo[1,2-a]pyrimidine-6-carboxylic acid ethyl ester

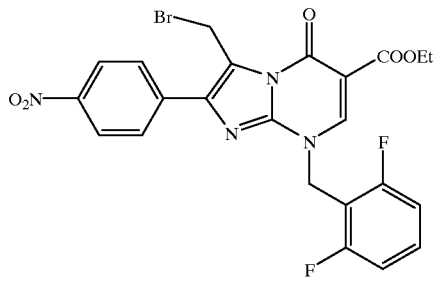

A suspension of the compound obtained in Example 5 (0.79 g, 1.7 mmol), N-bromosuccinimide (0.33 g, 1.86 mmol) and 2,2'-azobis(isobutyronitrile) (55 mg, 0.34 mmol) in carbon tetrachloride (150 ml) is refluxed under heating for 4 hours to yield a transparent brown solution. The reaction mixture is concentrated under reduced pressure to distill off half the solvent, after which it is dispensed to chloroform (100 ml) and a saturated aqueous solution of sodium hydrogen carbonate (200 ml). The water layer is extracted with chloroform (100 ml), and then the organic layers are combined and dried over sodium sulfate, after which the solvent is distilled off under reduced pressure to yield a crude brown crystalline product (1.07 g), which is then purified by recrystallization (methylene chloride-ether) to yield a brown crystal (0.74 g, 80%).

mp 205–210° C.

$^1$H-NMR (CDCl$_3$) δ: 1.40 (3H, t), 4.49 (2H, q), 5.31 (2H, s), 5.54 (2H, s), 7.02 (2H, t), 7.37–7.47 (1H, m), 8.04–8.38 (4H, q), 8.53 (1H, s).

IR (KBr): 4386, 3436, 3080, 2986, 1748, 1717, 1630, 1580, 1520, 1473, 1344, 1296, 1224, 1160, 1091, 1035, 855, 791, 719, 698, 613, 586, 499, 429 cm$^{-1}$.

Anal. Calcd for C$_{23}$H$_{17}$N$_4$O$_5$F$_2$Br: C, 50.47; H, 3.13; N, 10.24. Found: C, 50.58; H, 3.25; N, 10.23.

EXAMPLE 8

Using the compounds obtained in Examples 4 and 6, and in the same manner as Example 7, the compounds shown in Table 6 below are produced.

TABLE 6

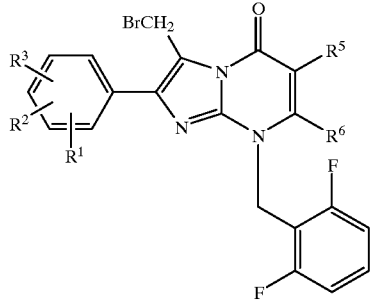

| Compd. No. | R$^1$, R$^2$, R$^3$ | R$^5$ | R$^6$ | yd. (%) | mp (° C.) |
|---|---|---|---|---|---|
| 1 | 4-nitro | Bz | Me | | |
| 2 | 4-nitro | Ph | H | | |
| 3 | 4-nitro | methoxy | H | | |
| 4 | 4-nitro | butoxy | H | | |
| 5 | 4-nitro | benzyloxy | H | | |
| 6 | 4-cyclopropylmethoxy | Bz | Me | 80 | amorphous |
| 7 | 4-methoxy | Bz | Me | | |
| 8 | 4-acetoxy | Bz | Me | | |
| 9 | 4-cyclopropylmethoxy | Ph | H | | |
| 10 | 4-acetoxy | Ph | H | | |
| 11 | 4-acetoxy | methoxy | H | | |
| 12 | 4-acetoxy | butoxy | H | | |
| 13 | 4-acetoxy | benzyloxy | | | |
| 14 | 4-(N-Boc-N-acetylamino) | Ph | H | 60 | amorphous |
| 15 | 4-(N-Boc-N-acetylamino) | Bz | Me | 80 | amorphous |
| 16 | 4-cyclopropylmethoxy | Ph | H | 80 | amorphous |
| 17 | 4-cyclopropylmethoxy | 4-chlorophenyl | H | 90 | amorphous |
| 18 | 4-cyclopropylmethoxy | 4-methoxyphenyl | H | 75 | amorphous |
| 19 | 4-nitro | 4-(3-methylbutyryl) | H | 72 | amorphous |
| 20 | 4-methoxy | ethoxycarbonyl | H | 80 | amorphous |
| 21 | 4-acetoxy | ethoxycarbonyl | H | 90 | amorphous |

EXAMPLE 9

Production of 8-(2,6-difluorobenzyl)-5,8-dihydro-3-(N-methyl-N-benzylaminomethyl)-2-(4-nitrophenyl)-5-oxoimidazo[1,2-a]pyrimidine-6-carboxylic acid ethyl ester

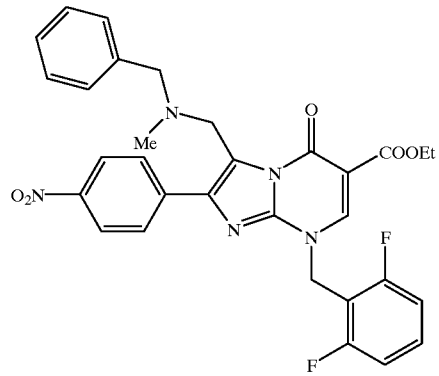

To a solution of the compound obtained in Example 7 (1.3 g, 10 mmol) in DMF (50 ml), N-ethyldiisopropylamine (1.3 g, 10 mmol) and N-methylbenzylamine (0.7 g, 6 mmol) are added, followed by overnight stirring at about 15 to 25° C. The brown substance obtained by concentration under reduced pressure of the reaction mixture is dispensed to a saturated aqueous solution of sodium hydrogen carbonate (300 ml) and ethyl acetate (200 ml). The water layer is extracted with ethyl acetate (50 ml), and then the organic layers are combined, washed with saturated saline (300 ml), and dried over sodium sulfate, after which the solvent is distilled off under reduced pressure to yield a crude brown crystalline product (2.2 g), which is then purified by flush column chromatography and recrystallized from dichloromethane-n-hexane to yield a yellow crystal (1.42 g, 56%).

mp 187–189° C.

$^1$H-NMR (CDCl$_3$) δ: 1.40 (3H, t), 2.27 (3H, s), 3.69 (2H, s), 4.37 (2H, s), 4.40 (2H, q), 5.51 (2H, s), 6.99 (2H, t), 7.16–7.46 (6H, m), 8.26–8.33 (4H, q), 8.48 (1H, s).

IR (KBr): 4470, 3452, 2982, 2364, 1746, 1715, 1630, 1603, 1516, 1475, 1344, 1301, 1214, 1174, 1100, 1036, 855, 789, 748, 700, 499 cm$^{-1}$.

FAB-MS m/e 588.4 (MH+)

Anal. Calcd for C$_{31}$H$_{27}$N$_5$O$_5$F$_2$.0.7H$_2$O: C, 62.04; H, 4.77; N, 11.67. Found: C, 62.03; H, 4.47; N, 11.35.

EXAMPLE 10

Using the compounds obtained in Example 8, and in the same manner as Example 9, the compounds shown in Table 7 below are produced.

TABLE 7

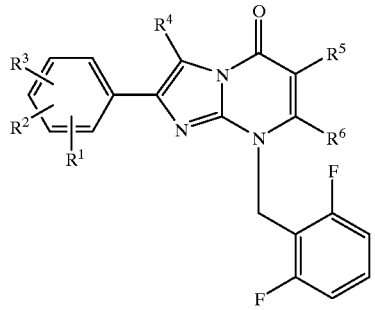

| Cpd. No. | R$^1$, R$^2$, R$^3$ | R$^4$ | R$^5$ | R$^6$ | yd. (%) | mp (° C.) |
|---|---|---|---|---|---|---|
| 1 | 4-nitro | *) | Bz | Me | | |
| 2 | 4-nitro | *) | Ph | H | | |
| 3 | 4-nitro | *) | methoxy | H | | |
| 4 | 4-nitro | *) | butoxy | H | | |
| 5 | 4-nitro | *) | benzyloxy | H | | |
| 6 | 4-cyclopropylmethoxy | *) | Bz | Me | 71 | hydrochloride 172–176 |
| 7 | 4-methoxy | *) | benzyl | Me | | |
| 8 | 4-acetoxy | *) | Bz | Me | | |
| 9 | 4-cyclopropylmethoxy | *) | Ph | H | | |
| 10 | 4-acetoxy | *) | Ph | H | | |
| 11 | 4-acetoxy | *) | methoxy | H | | |
| 12 | 4-acetoxy | *) | butoxy | H | | |
| 13 | 4-acetoxy | *) | benzyloxy | H | | |
| 14 | 4-isobutyrylamino | *) | Bz | Me | 4 | hydrochloride 165–168 |
| 15 | 4-nitro | **) | ethoxycarbonyl | H | 59 | amorphous |
| 16 | 4-(N-Boc-N-acetylamino) | *) | phenyl | H | 80 | amorphous |
| 17 | 4-(N-Boc-N-acetylamino) | *) | Bz | Me | 80 | amorphous |
| 18 | 4-cyclopropylmethoxy | *) | Ph | H | 75 | amorphous |
| 19 | 4-cyclopropylmethoxy | *) | 4-chlorophenyl | H | 70 | amorphous 155–161 (hydrochloride) |
| 20 | 4-cyclopropylmethoxy | *) | 4-methoxyphenyl | H | 73 | amorphous 184–187 (hydrochloride) |
| 21 | 4-nitro | *) | 4-(3-methylbutyryl) | H | 83 | amorphous |
| 22 | 4-methoxy | *) | ethoxycarbonyl | H | 43 | 190–192 hydrochloride |
| 23 | 4-acetoxy | *) | ethoxycarbonyl | H | 85 | amorphous |

*) N-methyl-N-benzylaminomethyl
**) N',N'-diethyl-N-methylethylenediaminomethyl

EXAMPLE 11

Production of 8-(2,6-difluorobenzyl)-5,8-dihydro-3-(hydroxymethyl)-2-(4-nitrophenyl)-5-oxoimidazo[1,2-a]pyrimidine-6-carboxylic acid ethyl ester

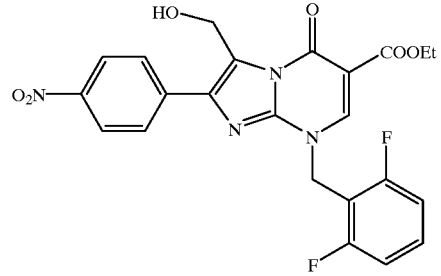

The by-product in Example 7 (obtained before recrystallizing procedure with methylene chloride-n-hexane) is purified by recrystallization (methylene chloride-n-hexane) to yield a brown-yellow crystal (0.14 g).

mp 230–232° C.

$^1$H-NMR (CDCl$_3$) δ: 1.40 (3H, t), 3.68 (1H, t), 4.41 (2H, q), 5.01 (2H, d), 5.56 (2H, s), 7.03 (2H, t), 7.38–7.48 (1H, m), 7.88–8.33 (4H, q), 8.55 (1H, s).

IR (KBr): 3460, 1736, 1601, 1518, 1475, 1344, 1299, 1216, 1106, 1038, 855, 793, 719, 499 cm$^{-1}$.

FAB-MS m/e 485.0 (MH$^+$)

Anal. Calcd for C$_{23}$H$_{18}$N$_4$O$_6$F$_2$.0.3H$_2$O: C, 56.04; H, 3.83; N, 11.44. Found: C, 56.46; H, 3.64; N; 11.37.

EXAMPLE 12

Production of 2-(4-aminophenyl)-8-(2,6-difluorobenzyl)-5,8-dihydro-3-(N-methyl-N-benzylaminomethyl)-5-oxoimidazo[1,2-a]pyrimidine-6-carboxylic acid ethyl ester

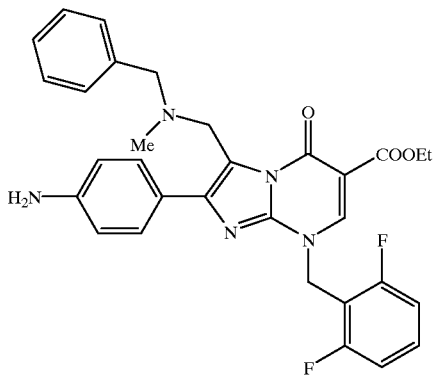

To a solution of the compound obtained in Example 9 (1.0 g, 1.7 mmol) and iron powder (0.5 g, 8.5 mmol) in ethanol (20 ml), concentrated hydrochloric acid (10 ml) is added drop by drop under ice cooling conditions over a 1-hour period, followed by stirring under ice cooling conditions for 4 hours, to yield a blackish green suspension. To the reaction mixture, a saturated aqueous solution of sodium hydrogen carbonate (100 ml), chloroform (200 ml) and Celite are carefully added under ice cooling conditions, followed by stirring, to yield a gray suspension, which is then filtered, after which the organic layer is dispensed. The water layer is extracted with chloroform (100 ml), and then the organic layers are combined, washed with a saturated solution of sodium hydrogen carbonate (200 ml), and dried over sodium sulfate, after which the solvent is distilled off under reduced pressure to yield a crude dark brown product (1.1 g), which is then purified by flush column chromatography to yield a red-brown substance (1.04 g), which is then recrystallized (methylene chloride-n-hexane) to yield a red-brown crystal (0.86 g, 91%).

mp 161–166° C.

$^1$H-NMR (CDCl$_3$) δ: 1.38 (3H, t), 2.17 (3H, s), 3.65 (2H, s), 3.78 (2H, bs, NH$_2$), 4.31 (2H, s), 4.38 (2H, q), 5.50 (2H, s), 6.74–7.88 (4H, q), 6.96–7.43 (8H, m), 8.37 (1H, s).

IR (KBr): 4566, 3366, 2980, 2362, 1740, 1705, 1591, 1510, 1473, 1392; 1371, 1301, 1214, 1183, 1102, 1036, 903, 839, 791, 737, 702, 607, 499 cm$^{-1}$.

FAB-MS m/e 558.2 (MH$^+$)

Anal. Calcd for C$_{31}$H$_{29}$N$_5$O$_3$F$_2$.0.3H$_2$O: C, 66.14; H, 5.30; N, 12.44. Found: C, 66.15; H, 5.35; N, 12.44.

EXAMPLE 13

Using the compounds obtained in Example 10, and in the same manner as Example 12, the compounds shown in Table 8 below are produced.

TABLE 8

| Cpd. No. | R$^4$ | R$^5$ | R$^6$ | yd. (%) | mp (° C.) |
|---|---|---|---|---|---|
| 1 | N-methyl-N-benzylamino-methyl | Bz | Me | | |
| 2 | N-methyl-N-benzylamino-methyl | Ph | H | | |
| 3 | N-methyl-N-benzylamino-methyl | methoxy | H | | |
| 4 | N-methyl-N-benzylamino-methyl | butoxy | H | | |
| 5 | N-methyl-N-benzylamino-methyl | benzyloxy | H | | |
| 6 | N',N'-diethyl-N-methyl-ethylenediaminomethyl | ethoxy carbonyl | H | 97 | amorphous |
| 7 | N-methyl-N-benzylamino-methyl | 4-(3-methyl-butyryl) | H | 30 | amorphous |

EXAMPLE 14

Production of 8-(2,6-difluorobenzyl)-5,8-dihydro-2-(4-isobutyrylaminophenyl)-3-(N-methyl-N-benzylaminomethyl)-5-oxoimidazo[1,2-a]pyrimidine-6-carboxylic acid ethyl ester

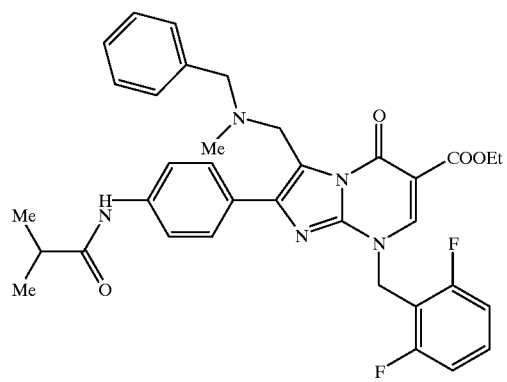

To a solution of the compound obtained in Example 12 (0.28 g, 0.5 mmol) and triethylamine (0.2 g, 2.0 mmol) in dichloromethane (25 ml), isobutyryl chloride (0.11 g, 1.0 mmol) is added drop by drop under ice cooling conditions over a 1-minute period, followed by stirring under ice cooling conditions for 1 hour. The reaction mixture is dispensed to dichloromethane (30 ml) and a saturated aqueous solution of sodium hydrogen carbonate (30 ml). The water layer is extracted with dichloromethane (20 ml), and then the organic layers are combined and dried over sodium sulfate, after which the solvent is distilled off under reduced pressure to yield a crude red-brown product (0.3 g), which is then purified by flush column chromatography to yield a red-brown crystalline substance (0.24 g), which is then recrystallized (methylene chloride-n-hexane) to yield a red-brown crystal (0.22 g, 70%).

mp 98–103° C.

$^1$H-NMR (CDCl$_3$) δ: 1.28 (6H, d), 1.39 (3H, t), 2.18 (3H, s), 2.50–2.59 (1H, m), 3.66 (2H, s), 4.34 (2H, s), 4.39 (2H, q), 5.50 (2H, s), 6.99 (2H, t), 7.14–7.44 (6H, m), 7.62–8.04 (4H, q), 8.40 (1H, s).

IR (KBr): 4386, 3338, 2976, 2364, 1742, 1702, 1601, 1510, 1473, 1371, 1303, 1214, 1185, 1100, 1036, 847, 791, 737, 700, 501 cm$^{-1}$.

FAB-MS m/e 628.3 (MH$^+$)

Anal. Calcd for C$_{35}$H$_{35}$N$_5$O$_4$F$_2$.0.5H$_2$O: C, 66.03; H, 5.70; N, 11.00. Found: C, 66.08; H, 5.44; N, 11.04.

EXAMPLE 15

Production of 8-(2,6-difluorobenzyl)-5,8-dihydro-2-(4-ethylaminocarbonylaminophenyl)-3-(N-methyl-N-benzylaminomethyl)-5-oxoimidazo[1,2-a]pyrimidine-6-carboxylic acid ethyl ester

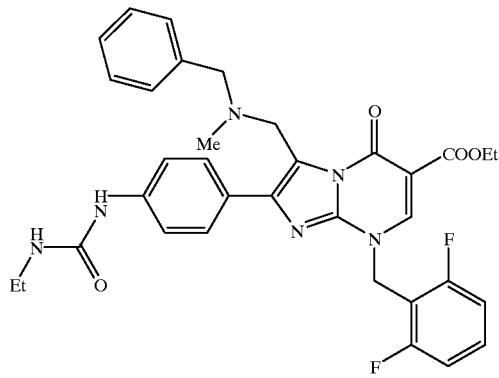

To a solution of the compound obtained in Example 12 (0.30 g, 0.54 mmol) in pyridine (10 ml), ethyl isocyanate (0.20 g, 2.8 mmol) is, followed by overnight stirring at about 15 to 25° C. The brown substance obtained by concentration under reduced pressure of the reaction mixture is dispensed to methylene chloride (40 ml) and a saturated aqueous solution of sodium hydrogen carbonate (40 ml). The water layer is extracted with methylene chloride (20 ml), and then the organic layers are combined and dried over sodium sulfate, after which the solvent is distilled off under reduced pressure to yield a crude brown product (0.32 g), which is then purified by flush column chromatography to yield a reddish white crystalline substance (0.27 g), which is then recrystallized (methylene chloride-n-hexane) to yield a brown crystal (0.22 g, 65%).

mp 191–196° C.

$^1$H-NMR (CDCl$_3$) δ: 1.17 (3H, t), 1.38 (3H, t), 2.17 (3H, s), 3.28–3.37 (1H, m), 3.64 (2H, s), 4.31 (2H, s), 4.38 (2H, q), 5.01 (1H, bs), 5.50 (2H, s), 6.69 (1H, s), 6.99 (2H, t), 7.11–8.01 (10H, m), 8.40 (1H, s).

IR (KBr): 4558, 4474, 3372, 2980, 2366, 1734, 1686, 1601, 1543, 1510, 1473, 1375, 1305, 1238, 1185, 1102, 1036, 845, 791, 737, 702, 503 cm$^{-1}$.

FAB-MS m/e 629.3 (MR$^+$)

Anal. Calcd for C$_{34}$H$_{34}$N$_6$O$_4$F$_2$.1.15H$_2$O: C, 62.87; H, 5.63; N, 12.94. Found: C, 62.87; H, 5.23; N, 13.28.

EXAMPLE 16

Using the compounds obtained in Example 13 and isobutyryl, ethyl isocyanate, various acid chlorides and isocyanate derivatives, and in the same manner as Examples 14 and 15, the compounds shown in Table 9 below are produced.

TABLE 9

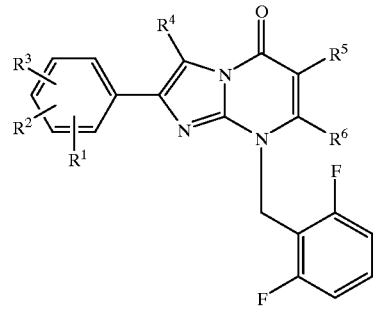

| Cpd. No. | R$^1$, R$^2$, R$^3$ | R$^4$ | R$^5$ | R$^6$ | yd. (%) | mp (° C.) |
|---|---|---|---|---|---|---|
| 1 | 4-ethylamino-carbonylamino | *) | Bz | Me | | |
| 2 | 4-isobutyrylamino | *) | Bz | Me | | |
| 3 | 4-ethylamino-carbonylamino | *) | Ph | H | | |
| 4 | 4-isobutyrylamino | *) | Ph | H | | |
| 5 | 4-ethylamino-carbonylamino | *) | methoxy | H | | |
| 6 | 4-isobutyrylamino | *) | methoxy | H | | |
| 7 | 4-ethylamino-carbonylamino | *) | butoxy | H | | |
| 8 | 4-isobutyrylamino | *) | butoxy | H | | |
| 9 | 4-ethylamino-carbonylamino | *) | benzyloxy | H | | |
| 10 | 4-isobutyrylamino | *) | benzyloxy | H | | |
| 11 | 4-isobutyrylamino | **) | ethoxy-carbonyl | H | 21 | hydro-chloride 149–153 |
| 12 | 4-ethylamino-carbonylamino | **) | ethoxy-carbonyl | H | 54 | hydro-chloride 142–146 |
| 13 | 4-(4-pyridyl-aminocarbonyl-amino) | *) | ethoxy-carbonyl | H | | |
| 14 | 4-(3-furyl-carbonylamino) | *) | Ph | H | 100 | hydro-chloride 185–190 |
| 15 | 4-(3-furyl-carbonylamino) | *) | Bz | Me | 82 | hydro-chloride 193–199 |
| 16 | 4-(methoxyamino carbonylamino) | *) | Bz | Me | 27 | 97–99 (free) |
| 17 | 4-(3-furyl-carbonylamino) | *) | ***) | H | 51 | 195–196 (free) |
| 18 | cyclopropane-carbonylamino | *) | ***) | H | 9 | amorphous |
| 19 | 4-(3-furyl-carbonylamino) | *) | 4-(3-methyl-butyryl) | H | 50 | hydro-chloride 149–153 |

*) N-methyl-N-benzylaminomethyl
**) N',N'-diethyl-N-methylethylenediaminomethyl
***) (N-methyl-N-methoxyamino) carbonyl

EXAMPLE 17

Preparation of 8-(2,6-difluorobenzyl)-5,8-dihydro-2-(4-(N-Boc-N-acetylamino)phenyl)-3-methyl-6-benzyl-7-methyl-5-oxoimidazo[1,2-a]pyrimidine

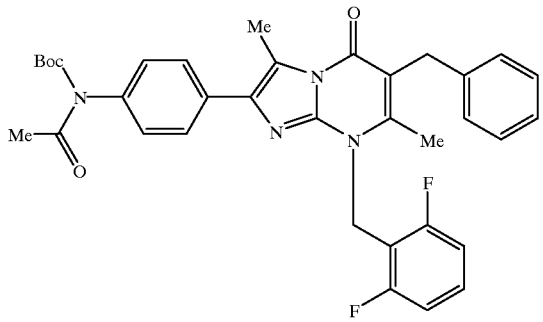

To a solution of the compound No. 22 obtained in Example 4 (51.4 g) and dimethylaminopyridine (24.5 g, 0.20 mmol) In dichioromethane (300 ml) is added (Boc)$_2$O (52.4 g, 0.24 mmol) with ice-cooling, successively the mixture is stirred at room temperature for 30 minuets. It is washed with dil. hydrochloric acid solution, and saturated saline, dried over Na$_2$SO$_4$, and the solvent is removed under reduced pressure to give the residue, which is chromatographed on silica gel to afford a yellow amorphous (44.4 g, 72%). A part of the amorphous (3.1 g) is recrystallized from ethyl acetate-n-hexane to give white crystalline powders (2.84 g, 66%).

mp 176–177° C.

FAB-MS m/e 613.2 (MH$^+$)

$^1$H-NMR (CDCl$_3$) δ: 1.40(9H, s), 2.19(3H, s), 2.56(3H, s), 2.92(3H, s), 3.97(2H, s), 5.67(2H, s), 6.88(2H, s), 7.11–7.36(8H, m), 8.03(2H, d).

EXAMPLE 18

Preparetion of 8-(2,6-difluorobenzyl)-5,8-dihydro-2-(4-(N-Boc-N-acetyl amino)phenyl)-3-methyl-6-phenyl-5-oxoimidazo[1,2-a]pyrimidine

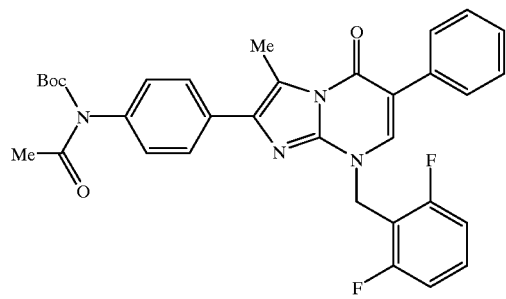

Using the compound No. 21 obtained in Example 4, and in the same manner as Example 17, 8-(2,6-difluorobenzyl)-5,8-dihydro-2-(4-(N-Boc-N-acetylamino)phenyl)-3-methyl-6-phenyl-5-oxoimidazo[1,2-a]pyrimidine is produced as white crystalline powders (yield, 70%).

mp 220–222° C.

EXAMPLE 19

Preparation of 2-[4-(N-Boc-amino)phenyl]-8-(2,6-difluorobenzyl)-5,8-dihydro-3-(N-methyl-N-benzylaminomethyl)-6-benzyl-7-methyl-5-oxoimidazo[1,2-a]pyrimidine

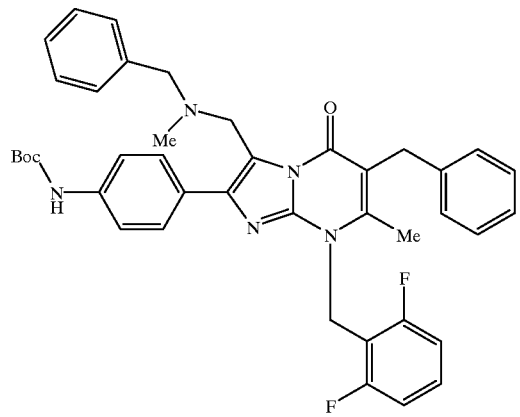

To a solution of the compound No. 17 obtained in Example 10 (0.65 g, 0.89 mmol) in THF (30 ml) is added a solution of sodium methoxide in methanol (28 %,3.0 ml) with ice-cooling. An additional solution of sodium methoxide in methanol (28%. 9.0 ml) is added at this temperature and is stirred for 1 hour at room temperature. The reaction mixture is partitioned between ethyl acetate (50 ml) and saturated saline. The aqueous layer is extracted with ethyl acetate (50 ml). The combined organic solution is washed with saturated saline (20 ml), dried over Na$_2$SO$_4$, successively evaporated under reduced pressure to afford a colorless amorphous (0.61 g, 100%). A part of this amorphous (0.08 g) is dissolved in ethyl acetate (3 ml) To this solution is added 1M HCl ether solution (0.174 ml) with ice-cooling. The residual solid Is recrystallized from ethanol-dichloromethane-ethyl ether to afford white crystalline powders (0.057 g, 68%).

mp 179–184° C.

FAB-MS m/e 690.2 (MH$^+$).

EXAMPLE 20

Preparation of 8-(2,6-difluorobenzyl)-5,8-dihydro-2-(4-(N-Boc-amino)phenyl)-3-(N-methyl-N-benzylaminomethyl)-6-phenyl-5-oxoimidazo[1,2-a]pyrimidine

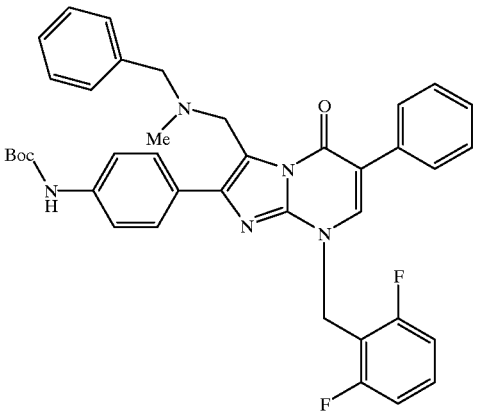

Using the compound No. 16 obtained in Example 10, and in the same manner as Example 19, 8-(2,6-difluorobenzyl)-5,8-dihydro-2-(4-(N-Boc-amino)phenyl)-3-(N-methyl-N-benzylaminomethyl)-6-phenyl-5-oxoimidazo[1,2-a]pyrimidine is produced as a white amorphous (yield, 96%).

EXAMPLE 21

Preparation of 8-(2,6-difluorobenzyl)-5,8-dihydro-2-(4-aminophenyl)-3-(N-methyl-N-benzylaminomethyl)-6-benzyl-7-methy-5-oxoimidazo[1,2-a]pyrimidine

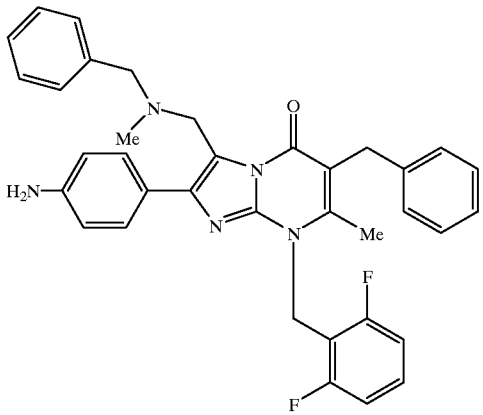

To a solution of the compound obtained in Example 19 (0.53 g, 0.77 mol) in dichloromethane (20 ml) is added trifluoroacetic acid (0.24 ml, 3.07 mmol) with ice-cooling. An additional amount of trifluoroacetic acid (1.5 ml) is added at room temperature and is stirred for 5 hours at room temperature. The reaction mixture is partitioned between chloroform (100 ml) and aqueous saturated NaHCO$_3$ solution (30 ml). The aqueous layer is extracted with chloroform (30 ml). The combined organic solution is washed with saturated saline (20 ml), dried over Na$_2$SO$_4$, successively evaporated under reduced pressure to give the residue, which is chromatographed on silica gel to afford a pale brown colorless amorphous (0.41 g, 90%).

FAB-MS m/e 590.1(MH$^+$)

EXAMPLE 22

Preparation of 8-(2,6-difluorobenzyl)-5,8-dihydro-2-(4-aminophenyl)-3-(N-methyl-N-benzylaminomethyl)-6-phenyl-5-oxoimidazo[1,2-a]pyrimidine

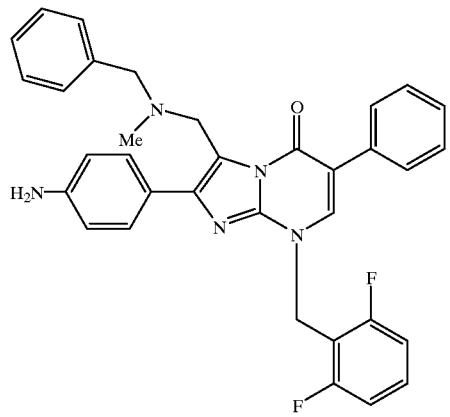

Using the compounds obtained in Example 20, and in the same manner as Example 21, 8-(2,6-difluorobenzyl)-5,8-dihydro-2-(4-aminophenyl)-3-(N-methyl-N-benzylaminomethyl)-6-phenyl-5-oxoimidazo[1,2-a]pyrimidine is produced as a white amorphous (yield, 83%).

EXAMPLE 23

Preparation of 8(2,6-difluorobenzyl)-5,8-dihydro-2-(4-hydroxyphenyl)-3-methyl-6-bromo-5-oxoimidazo[1,2-a]pyrimidine

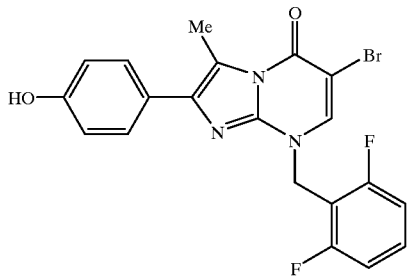

To a solution of the compound No. 23 obtained in Example 4 (0.27 g, 0.55 mmol) in THF (30 ml) is added a solution of K$_2$CO$_3$ (0.152 g, 1.11 mmol) in water (2 ml). The reaction mixture is stirred at 60° C. for 30 minutes. To the mixture is added 1N aqueous NaOH solution (5 ml). Then the reaction mixture is stirred at 60° C. for 1 hours, successively is partitioned between ethyl acetate (100 ml) and dil. hydrochloric acid solution(30 ml). The aqueous layer is extracted with ethyl acetate (30 ml). The combined organic solution is washed with saturated saline (20 ml), dried over Na$_2$SO$_4$, successively evaporated under reduced pressure to give a pale yellow amorphous (0.25 g, 100%).

$^1$H-NMR(CDCl$_3$) δ: 2.85(3H, s), 5.46(2H, s), 6.68(2H, t), 6.87–7.14(3H, m), 7.39(2H, d), 7.56(1H, s), 8.17(1H, s).

EXAMPLE 24

Preparation of 8-(2,6-difluorobenzyl)-5,8-dihydro-2-(4-cyclopropylmethoxyphenyl)-3-methyl-6-bromo-5-oxoimidazo[1,2-a]pyrimidine

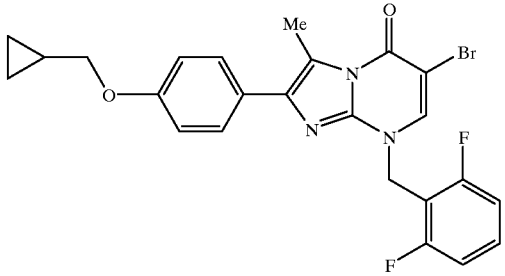

To a solution of the compound obtained in Example 23 (0.25 g, 0.56 mmol) in DMF (30 ml) is added (bromomethyl)cyclopropane (0.114 g, 0.84 mmol), K$_2$CO$_3$ (0.116 g, 0.84 mmol) and KI (0.047 g, 0.28 mmol). The residual reaction mixture is stirred at 60° C. for 4 hours. To this mixture is added (bromomethyl)cyclopropane (0.14 g, 1.0 mmol). It is stirred at this temperature for 21 hours and is evaporated under reduced pressure to afford the residue, which is partitioned between chloroform (100 ml) and aqueous saturated NaHCO$_3$ solution (30 ml). The aqueous layer is extracted with chloroform (30 ml). The combined organic extract is dried over Na$_2$SO$_4$ and concentrated under reduced pressure to give the residue, which is chromatographed on silica gel to afford white crystals (0.23 g, 82%).

mp 230–231° C.

$^1$H-NMR(CDCl$_3$) δ: 0.38–0.40(2H, m), 0.62–0.68(2H, m), 1.22–1.29(1H, m), 2.85(3H, s), 3.84(2H, d), 5.44(2H, s), 6.98–7.02(4H, m), 7.34–7.44(1H, m), 7.60–7.65(3H, m).

EXAMPLE 25

Preparation of 8-(2,6-difluorobenzyl)-5,8-dihydro-2-(4-cyclopropylmethoxyphenyl)-3-methyl-6-phenyl-5-oxoimidazo[1,2-a]pyrimidine

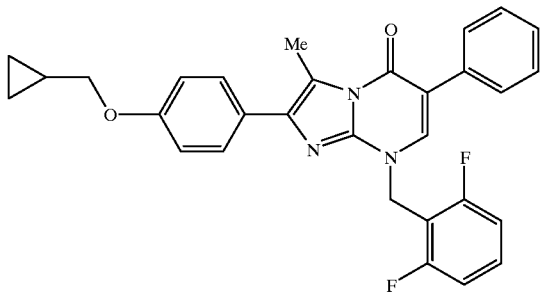

The compound obtained in Example 24 (0.02 g, 0.04 mmol) is added to DME (30 ml), which is oxygen free. To this mixture is added phenylboronic acid (0.0054 g, 0.044 mmol), 2N aqueous K$_2$CO$_3$ solution (0.1 ml), tetrakis(triphenylphosphine)palladium(0) (0.0046 g, 0.004 mmol). Then the mixture is refluxed for 3 hours under argon atmosphere. The residual reaction mixture is partitioned between ethyl acetate (100 ml) and water (30 ml). The aqueous layer is extracted with ethyl acetate (30 ml). The combined organic extract is dried over Na$_2$SO$_4$ and concentrated under reduced pressure to give the residue, which is chromatographed on silica gel to afford white crystals (0.016 g, 78%).

mp 210–214° C.

$^1$H-NMR(CDCl$_3$) δ: 0.35–0.40(2H, m), 0.63–0.68(2H, m), 1.23–1.31(1H, m), 2.90(3H, s), 3.85(2H, d), 5.50(2H, s), 6.95–7.01(4H, m), 7.29–7.50(4H, m), 7.51–7.55(3H, m), 7.67(2H, d).

EXAMPLE 26-1

Preparation of 8-(2,6-difluorobenzyl)-5,8-dihydro-2-(4-cyclopropylmethoxyphenyl)-3-methyl-6-(4-chlorophenyl)-5-oxoimidazo[1,2-a]pyrimidine

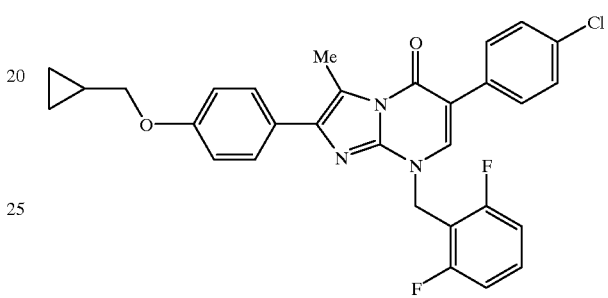

Using the compounds obtained in Example 24, and in the same manner as Example 25, with (4-chlorophenyl)boronic acid in place of phenylboronic acid, 8-(2,6-difluorobenzyl)-5,8-dihydro-2-(4-cyclopropyl methoxyphenyl)-3-methyl-6-(4-chlorophenyl)-5-oxoimidazo[1,2-a]pyrimidine is produced as white crystals (yield, 66%).

mp 203–205° C.

EXAMPLE 26-2

Preparation of 8-(2,6-difluorobenzyl)-5,8-dihydro-2-(4-cyclopropylmethoxyphenyl)-3-methyl-6-(4-methoxyphenyl)-5-oxoimidazo[1,2-a]pyrimidine

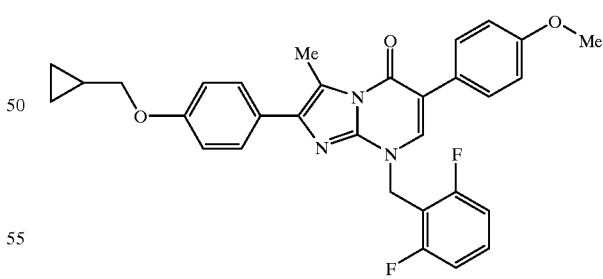

Using the compounds obtained in Example 24, and in the same manner as Example 25, with (4-methoxyphenyl)boronic acid in place of phenylboronic acid, 8-(2,6-difluorobenzyl)-5,8-dihydro-2-(4-cyclopropylmethoxyphenyl)-3-methyl-6-(4-methoxyphenyl)-5-oxoimidazo[1,2-a]pyrimidine is produced as white crystals (yield, 66%).

mp 192–193° C.

EXAMPLE 27

Preparation of 8-(2,6-difluorobenzyl)-5,8-dihydro-2-phenyl-3-methyl-5-oxoimidazo[1,2-a]pyrimidine-6-(N-methy-N-methoxy)carboxyamide

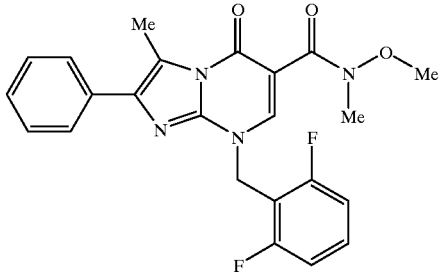

To a well stirring suspension of N,O-dimethylhydroxyamine hydrochloride (10.5 g) in dichloromethane (210 ml) is added dropwise a solution of dimethylaluminum chloride (1.05 M hexane solution, 100 ml) with ice-cooling. After generating a gas has ceased, to this mixture is added a solution of the compound obtained in Example 3 (3.81 g, 9 mmol) in dichloromethane (60 ml). The reaction mixture is stirred overnight. To the mixture is added water (30 ml), successively is extracted with chloroform(100 ml×2). The organic extract is dried over $Na_2SO_4$, evaporated under reduced pressure to give the residue, which is chromatographed on silica gel to afford white crystalline powders (1.99 g, 50%).

$^1$H-NMR (CDCl$_3$) δ: 2.90(3H, t), 3.32(3H, s), 3.71(3H, s), 5.48(2H, s), 6.99(2H, t), 7.30–7.50(4H, m), 7.65–7.80(2H, m), 7.74(1H, s).

EXAMPLE 28

Preparation of 8-(2,6-difluorobenzyl)-5,8-dihydro-2-phenyl-3-methyl-6-(3-methylbutyryl)-5-oxoimidazo[1,2-a]pyrimidine

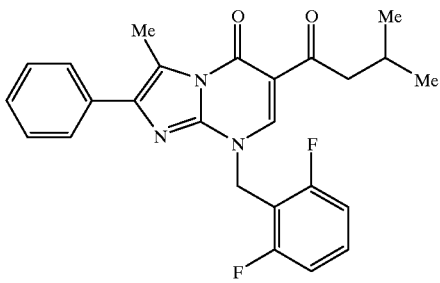

To a solution of the compound obtained in Example 27 (0.35 g, 0.8 mmol) in THF (35 ml) is added isobutylmagnesium bromide (2 M ethyl ether solution, 4 ml) with ice-cooling. After the addition is completed, the mixture is stirred overnight. To this mixture is added 1N hydrochloric acid solution (30 ml). The residual reaction mixture is extracted with chloroform (100 ml×2). The organic extract is dried over $Na_2SO_4$ and concentrated under reduced pressure to give the residue, which is chromatographed on silica gel to afford white crystals (0.18 g, 52%).

$^1$H-NMR (CDCl$_3$) δ: 0.98(6H,d), 2.25(1H,m), 2.92(3H,s), 2.99(2h,d), 5.53(2H,s), 7.00(2H,t), 7.30–7.50(4H,m), 7.65–7.75(2H,m), 8.37(1H, s).

EXAMPLE 29

Preparation of 8-(2,6-difluorobenzyl)-5,8-dihydro-2-(4-nitrophenyl)-3-methyl-6-(3-methylbutyryl)-5-oxoimidazo[1,2-a]pyrimidine

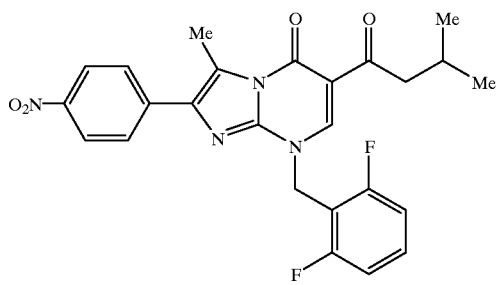

To a solution of the compound obtained in Example 28 (0.10 g, 0.23 mmol) in conc. sulfuric acid (2 ml) is added dropwise a solution of sodium nitrite in sulfuric acid (1 M, 0.23 ml) with ice-cooling. In the same manner as Example 3, the compound, 8-(2,6-difluorobenzyl)-5,8-dihydro-2-(4-nitrophenyl)-3-methyl-6-(3-methylbutyryl)-5-oxoimidazo[1,2-a]pyrimidine is given as yellow crystals.

EXAMPLE 30

Preparation of 8-(2,6-difluorobenzyl)-5,8-dihydro-2-(4-aminophenyl)-3-(N-methyl-N-benzylaminomethyl)-5-oxoimidazo[1,2-a]pyrimidine-6-(N-methyl-N-methoxy)carboxamide

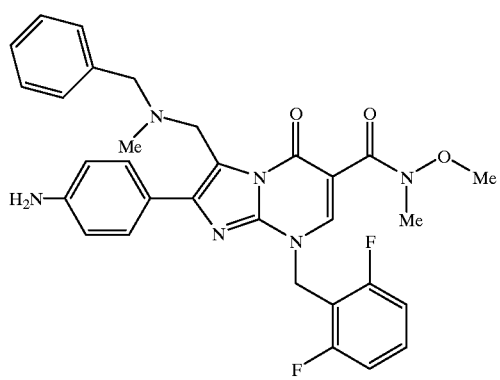

To a well stirring suspension of N,O-dimethyihydroxyamine hydrochloride (8.88 g) in dichloromethane (180 ml) is added dropwise a solution of dimethylaluminum chloride (1.05 M hexane solution, 88.8 ml) with ice-cooling. After generating a gas ceases, to this mixture is added a solution of the compound obtained in Example 12 (4.44 g, 8 mmol) in dichloromethane (80 ml). The reaction mixture is stirred for 1 hour at room temperature. To the mixture is added water (30 ml), successively is extracted with ethyl acetate (100 ml×2). The organic extract is died over $Na_2SO_4$, evaporated under reduced pressure to give the residue, which is chromatographed on silica gel to afford white crystalline powders (1.86 g, 41%).

$^1$H-NMR (CDCl$_3$) δ: 2.17(3H, s), 3.33(3H, s), 3.59(2H,s), 3.71(3H, s), 4.31(2H, s), 5.48(2H, s), 6.76(2H, d), 6.99(2H, t), 7.15–7.50(6H, m), 7.75(1H, s), 7.87(2H, d).

EXAMPLE 31

Preparation of 8-(2,6-difluorobenzyl)-5,8-dihydro-2-(3-furylcarbonylaminophenyl)-3-(N-methyl-N-benzylaminomethyl)-6-benzoyl-5-oxoimidazo[1,2-a]pyrimidine

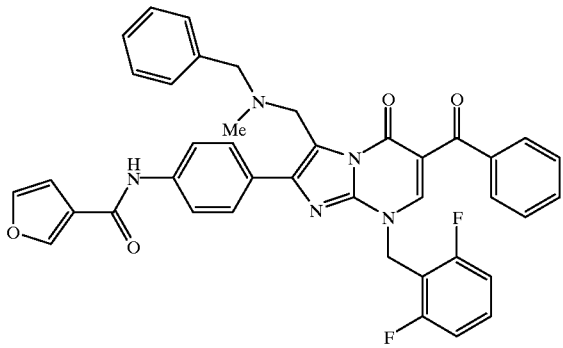

To a solution of the compound No. 17 obtained in Example 16 (0.10 g, 0.15 mmol) in THF (6 ml) is added phenylmagnesium bromide (2 M ethyl ether solution, 0.08 ml) with ice-cooling. After the addition is completed, the mixture is stirred overnight. To this mixture is added carefully aqueous saturated NaHCO₃ solution (30 ml). The residual reaction mixture is extracted with ethyl acetate (30 ml×2). The organic extract is dried over Na₂SO₄ and concentrated under reduced pressure to give the residue, which is chromatographed on silica gel to afford white crystals (0.022 g, 16%).

mp 194–202° C.

$^1$H-NMR (CDCl$_3$) δ: 2.15(3H, s), 3.60(2, s), 4.31(2H, s), 5.54(2H, s), 6.76(1H, d), 7.01(2H, t), 7.10–7.60(11H, m), 7.70(2H, d), 7.81(2H, d), 8.04(1H, s), 8.07(2H, s).

EXAMPLE 32

Preparation of 8-(2,6-difluorobenzyl)-5,8-dihydro-2-(4-aminophenyl)-3-(N-methyl-N-benzylaminomethyl)-5-oxoimidazo[1,2-a]pyrimidine-6-carboxylic acid isopropyl ester

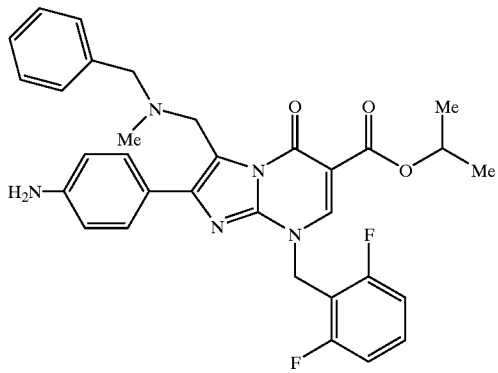

To a solution of the compound obtained in Example 12 (0.10 g, 0.18 mmol) in chloroform (5 ml) is added a solution of titanium(IV) isopropoxide (0.3 ml, 1.0 mmol) in 2-propanol (10 ml). Then the mixture is refluxed at 80° C. for 8 hours, successively is stirred at room temperature for 150 minutes. To this mixture is added a mixture of chloroform (50 ml) and water (50 ml). The aqueous layer is extracted with chloroform (20 ml). The combined organic extract is dried over Na₂SO₄ and concentrated under reduced pressure to give the residue, which is chromatographed on silica gel to afford white-brown crystalline solid, which is recrystallized from chloroform-n-hexane to afford pale brown crystals (0.58 g, 94%).

mp 168–170° C.

$^1$H-NMR (CDCl$_3$) δ: 1.36 (6H, d), 2.15(3H, s), 3.65(3H, s), 3.76(2H, brs), 4.32(2H, s), 5.18–5.26(1H, m), 5.49(2H, s), 6.75(2H, d), 6.99(2H, t), 7.11–7.43(6H, m), 7.85(2H, d), 8.32(1H, s).

EXAMPLE 33

Preparation of 8-(2,6-difluorobenzyl)-5,8-dihydro-2-[4-(methoxyaminocarbonylamino)phenyl]-3-(N-methyl-N-benzylaminomethyl)-5-oxoimidazo[1,2-a]pyrimidine-6-carboxylic acid isopropyl ester

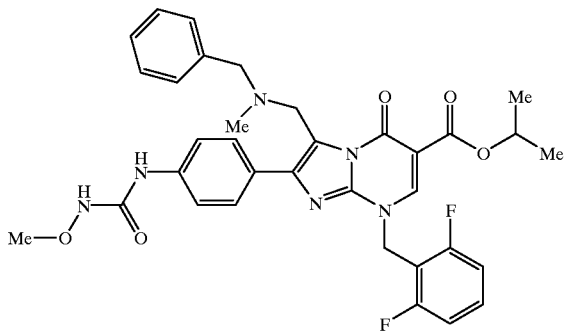

To a solution of the compound obtained in Example 32 (1.39 g, 2.43 mmol) in dichloromethane (30 ml) are added 1,1'-carbonyldi-imidazole (0.79 g, 4.86 mmol) and triethylamine (0.68 ml, 4.86 mmol) with ice-cooling. Then the mixture is stirred at room temperature for 2 days. To this reaction mixture is added O-methylhydroxyamine hydrochloride(1.02 g, 12.2 mmol) and triethylamine (1.71 ml, 12.2 mmol) with ice-cooling. The reaction mixture is stirred at this temperature for 4 hours. To the residual mixture is added a mixture of chloroform (50 ml) and water (50 ml). The aqueous layer is extracted with chloroform (50 ml). The combined organic extract is dried over Na₂SO₄ and concentrated under reduced pressure to give the yellow residue, which is chromatographed on silica gel to afford white-brown crystalline solid. The solid is recrystallized from 2-propanol-ethyl acetate-isopropyl ether to afford pale yellow crystals (1.15 g, 73%).

mp 156–158° C.

$^1$H-NMR (CDCl$_3$) δ: 1.36 (6H, d), 2.17 (3H, s), 3.66 (2H, s), 3.83(3H, s), 4.33 (2H, s), 5.19–5.27(1H, m), 5.50 (2H, s), 6.99 (2H, t), 7.02–7.26(5H, m), 7.34–7.43(1H, m), 7.58(2H, d), 8.03(2H, d), 8.37(1H, s).

Anal. Calcd for C$_{34}$H$_{34}$N$_6$O$_5$F$_2$: C, 63.34; H, 5.32; N, 13.04. Found: C, 63.64; H, 5.26; N, 12.86.

EXAMPLE 34

Preparation of 8-(2,6-difluorobenzyl)-5,8-dihydro-2-[4-(ethylaminocarbonylamino)phenyl]-3-(N-methyl-N-benzylaminomethyl)-5-oxoimidazo[1,2-a]pyrimidine-6-carboxylic acid isopropyl ester

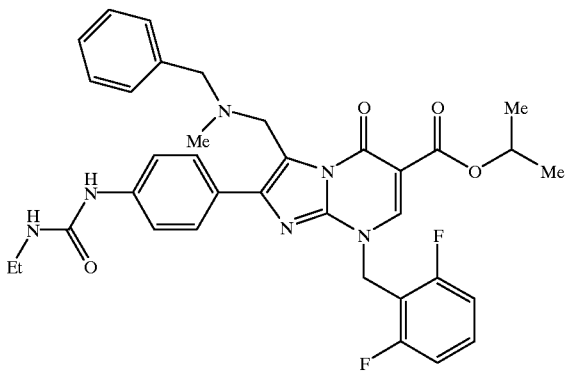

To a solution of the compound obtained in Example 32 (1.37 g, 2.40 mmol) in THF (3 ml) is added pyridine (0.5 ml) and ethyl isocyanate (0.38 ml, 4.8 mmol). Then the mixture is stirred at room temperature overnight. The reaction mixture is concentrated under reduced pressure to give the residue, which triturated with isopropyl ether to afford a crystalline solid, which is recrystallized from chloroform-isopropyl ether to afford pale yellow crystals (1.20 g, 78%).

mp 198–200° C.

$^1$H-NMR (CDCl$_3$) δ: 1.18(3H, t), 1.36(6H, d), 2.16 (3H, s), 3.28–3.37(1H, m), 3.64(2H, s), 4.32(2H, s), 4.94(1H, t), 5.19–5.27(1Hr m), 5.49(2H, s), 6.58(1H, s), 6.99(2H, t), 7.12–7.26(6H, m), 7.39(2H, d), 7.99(2H, d), 8.36(1H, s).

Anal. Calcd for C$_{35}$H$_{36}$N$_6$O$_4$F$_2$: C, 65.41; H, 5.65; N, 13.08. Found: C, 65.20; H, 5.60; N, 12.87.

EXAMPLE 35

Using the compounds obtained in Example 12 and various alkyl isocyanate derivatives, various acid halides and various alkyl sulfonylhalides, and in the same manner as Examples 14, 15, 33, and 34, the compounds shown in Table 10 below are produced.

TABLE 10

| Cpd. No. | R$^1$ | yield (%) | mp (° C.) |
|---|---|---|---|
| 1 | HOCH$_2$CH$_2$CONH | 38 | 207–209 (hydrochloride) |
| 2 | MeONHCONH | 50 | 154–158 (hydrochloride) |
| 3 | (3-Me, 5-Me isoxazol-4-yl)CONH | 68 | 153–156 (hydrochloride) |
| 4 | (isoxazol-5-yl)CONH | 38 | 155 (dc.) (hydrochloride) |
| 5 | (2-O$_2$N-thiophen-4-yl)CONH | 44 | 162–164 (hydrochloride) |
| 6 | (4-Me, 2-Me-thiazol-5-yl)CONH | 100 | 92–107 (hydrochloride) |
| 7 | (4-MeO-thiophen-3-yl)CONH | 90 | 155–163 (hydrochloride) |
| 8 | (5-Me, 1-Me-pyrazol-3-yl)CONH | 75 | 152–154 (hydrochloride) |

TABLE 10-continued

[Structure: Imidazo-pyrimidinone core with N-benzyl-N-methylaminomethyl group, COOEt, R¹-phenyl, and 2,6-difluorobenzyl substituents]

| Cpd. No. | R¹ | yield (%) | mp (° C.) |
|---|---|---|---|
| 9 | 3-furyl-CONH | 14 | 169–173 (hydrochloride) |
| 10 | 2-Me-C₆H₄-CONH | 47 | 201–204 (hydrochloride) |
| 11 | 2-MeO-C₆H₄-CONH | 36 | 144–149 (hydrochloride) |
| 12 | 3-thienyl-CH₂-CONH | 43 | 209–211 (hydrochloride) |
| 13 | EtOOCNH | 44 | 197–200 (hydrochloride) |
| 14 | 3-thienyl-CONH | 49 | 172–175 (hydrochloride) |
| 15 | 2-naphthyl-CONH | 37 | 202–204 (hydrochloride) |
| 16 | 3-pyridyl-CONH | 64 | 166–170 (dihydrochloride) |
| 17 | 1-adamantyl-CONH | 67 | 164–167 (hydrochloride) |
| 18 | 2-thienyl-SO₂NH | 26 | 157–162 (hydrochloride) |
| 19 | 1-methylpyrrol-2-yl | 9 | 144–148 (hydrochloride) |
| 20 | 4-F-C₆H₄-CONH | 70 | 152–155 (hydrochloride) |
| 21 | cyclopropyl-CONH | 53 | 199–204 (hydrochloride) |
| 22 | 4-Me-C₆H₄-SO₂NH | 64 | 177–179 (hydrochloride) |
| 23 | CH₂=CHCONH | 49 | 158–161 (hydrochloride) |
| 24 | 2-furyl-CONH | 55 | 190–193 (hydrochloride) |
| 25 | C₆H₅-NHCONH | 50 | 165–168 (hydrochloride) |
| 26 | (Me)₂CH-NHCONH | 40 | 159–160 (hydrochloride) |
| 27 | C₆H₅-CONH | 58 | 157–158 (hydrochloride) |

TABLE 10-continued

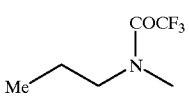

| Cpd. No. | R¹ | yield (%) | mp (° C.) |
|---|---|---|---|
| 28 | EtCONH | 61 | 158–166 (hydrochloride) |
| 29 | EtSO₂NH | 27 | 155–160 (hydrochloride) |
| 30 | Me(HO)CHCH₂NH | 24 | 89–91 (free base) |
| 31 | CF₃CONH | 83 | 172–174 (free base) |
| 32 | Me⌒N(COCF₃)⌒ | 74 | 147–149 (free base) |
| 33 | MeCH₂CH₂NH | 18 | 66–68 (free base) |

EXAMPLE 36

Preparation of 8-(2,6-difluorobenzyl)-5,8-dihydro-2-(4-hydroxyphenyl)-3-(N-methyl-N-benzylaminomethyl)-5-oxoimidazo[1,2-a]pyrimidine-6-carboxylic acid ethyl ester

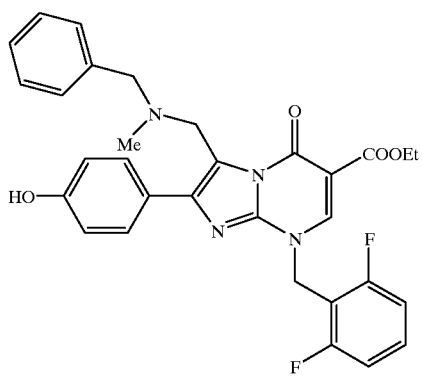

To a solution of the compound No. 23 obtained in Example 10 (3.1 g, 5.16 mmol) in dichloromethane (30 ml) is added a solution of sodium ethoxide (0.35 g, 5.16 mmol) in ethanol (20 ml) with ice-cooling. The mixture is stirred at this temperature for 1 hour and neutralized with 1N hydrochloric acid, successively concentrated under reduced pressure to give the residue, which is partitioned between chloroform (50 ml) and water (50 ml). The aqueous layer is extracted with chloroform (20 ml). The combined organic layer is dried over $Na_2SO_4$ and concentrated under reduced pressure to give a yellow solid, which is chromatographed on silica gel to afford a white amorphous (1.41 g, 49%).

$^1$H-NMR (CDCl$_3$) δ: 1.36(3H, t), 2.20(3H, s), 3.68(2H, s), 4.35–4.42(4H,m), 5.50(2H, s), 6.90(2H, d), 6.99(2H, t), 7.14–7.55(5H, m), 7.89(2H, d), 8.39(1H, s).

FAB-MS m/e 559.3 (MH⁺).

Anal. Calcd for $C_{31}H_{28}N_4O_4F_2 \cdot 0.5H_2O$: C, 65.60; H, 5.15; N, 9.87. Found: C, 65.49; H, 5.22; N, 9.77.

Experimental Example 1

(1) Preparation of $^{125}$I-leuprorelin

To a tube containing 10 μl of a 3×10⁻⁴ M aqueous solution of leuprorelin and 10 μl of 0.01 mg/ml lactoperoxidase, 10 μl (37 MBq) of a solution of Na$^{125}$I was added. After stirring, 10 μl of 0.001% $H_2O_2$ was added, and a reaction was carried out at about 15 to 25° C. for 20 minutes. By adding 700 μl of a 0.05% TFA (trifluoroacetic acid) solution, the reaction was stopped, followed by purification by reversed-phase HPLC. The HPLC conditions used are shown below. $^{125}$I-leuprorelin was eluted at a retention time of 26 to 27 minutes.

Column: TSKgel ODS-80™ (™ indicates a registered trademarks the same applies below) CTR (4.6 mm×10 cm;

Eluents:

Solvent A (0.05% TFA)

Solvent B (40% CH3CN—0.05% TFA)

0 minute (100% Solvent A)—3 minutes (100% Solvent A)—7 minutes (50% Solvent A+50% Solvent B)—40 minutes (100% Solvent B)

Eluting temperature: About 15 to 25° C.

Elution rate: 1 ml/min (2) Preparation of CHO (Chinese Hamster Ovarian) Cell membrane fraction containing human GnRH receptor Human GnRH receptor-expressing CHO cells (10⁹ cells) as prepared by the method described in European Patent Publication No. EP-0678577A were suspended in phosphate-buffered saline supplemented with 5 mM EDTA (ethylenediaminetetraacetic acid) (PBS-EDTA) and centrifuged at 100×g for 5 minutes. To the cell pellet, 10 ml of a cell homogenate buffer (10 mM NaHCO$_3$, 5 mM EDTA, pH 7.5) was added, followed by homogenization using the Polytron homogenizer. After centrifugation at 400×g for 15 minutes, the supernatant was transferred to an ultracentrifugation tube and centrifuged at 100,000×g for 1 hour to yield a membrane fraction precipitate. This precipitate was suspended in 2 ml of an assay buffer (25 mM Tris-HCl, 1 mM EDTA, 0.1% BSA (bovine serum albumin), 0.25 mM PMSF (phenylmethanesulfonyl fluoride), 1 μg/ml pepstatin, 20 μg/ml leupeptine, 100 μg/ml phosphoramidone, 0.03% sodium azide, pH 7.5) and centrifuged at 100,000×g for 1 hour. The membrane fraction recovered as a precipitate was again suspended in 20 ml of the assay buffer, dispensed, and stored at −80° C. before use upon thawing.

(3) Determination of $^{125}$I-leuprorelin Binding Inhibition Rate

The human membrane fraction prepared in paragraph (2) above was diluted with the assay buffer to yield a 200 μg/ml dilution, which was then dispensed at 188 μl per tube. To each tube, 2 μl of a solution of 2 mM compound in 60% DMSO (dimethyl sulfoxide) and 10 μl of 38 nM $^{125}$I-leuprorelin were added simultaneously. To determine maximum binding quantity, a reaction mixture of 2 μl of 60% DMSO and 10 μl of 38 nM $^{125}$I-leuprorelin was prepared. To determine non-specific binding amount, a reaction mixture of 2 μl of 100 μM leuprorelin in solution in 60% DMSO and 10 μl of 38 nM $^{125}$I-leuprorelin was prepared.

After a reaction was carried out at 25° C. for 60 minutes, the reaction mixture was aspirated and filtered through a polyethyleneimine-treated Whatman glass filter (GF-F). After this filtration, the radioactivity of $^{125}$I-leuprorelin remaining on the filter paper was measured, using a γ-counter.

The binding inhibition rate (%) for the subject compound (PMB) was calculated, using the equation:

$$PMB = (TB-SB)/(TB-NSB) \times 100$$

TB=maximum bound radioactivity
SB=radioactivity in presence of subject compound
NSB=non-specific bound radioactivity Inhibitory rates were then obtained for varied concentrations of the subject compound, and the subject compound concentration for 50% inhibition of binding (concentration for 50% PMB, $IC_{50}$ value) was calculated from a Hill plot. The $IC_{50}$ values of the compounds obtained in Examples above, as obtained by the determination method described above, are shown in Table below.

TABLE 11

| Example No. | $IC_{50}$ (nM) |
|---|---|
| 15 | 0.5 |

Preparation Example 1

Using the compound produced in Example 10 (Compound 6) (100 mg), 165 mg of lactose, 25 mg of corn starch, 4 mg of polyvinyl alcohol and 1 mg of magnesium stearate, tablets are produced by a conventional method.

Preparation Example 2

The compound produced in Example 10 (Compound 6) (5 g) is dissolved in distilled water for injection to make a total volume of 100 ml. This solution is aseptically filtered through a 0.22 μm membrane filter (produced by Sumitomo Electric Industries, Ltd. or Sartorius) and dispensed at 2 ml per washed sterile vial, followed by freeze-drying by a conventional method, to yield a 100 mg/vial freeze-dried injectable preparation.

Preparation Example 3

Using the compound produced in Example 14 (100 mg), 165 mg of lactose, 25 mg of corn starch, 4 mg of polyvinyl alcohol and 1 mg of magnesium stearate, tablets are produced by a conventional method.

Preparation Example 4

The compound produced in Example 14 (5 g) is dissolved in distilled water for injection to make a total volume of 100 ml. This solution is aseptically filtered through a 0.22 μm membrane filter (produced by Sumitomo Electric Industries, Ltd. or Sartorius) and dispensed at 2 ml per washed sterile vial, followed by freeze-drying by a conventional method, to yield a 100 mg/vial freeze-dried injectable preparation.

Preparation Example 5

Using the compound produced in Example 15 (100 mg), 165 mg of lactose, 25 mg of corn starch, 4 mg of polyvinyl alcohol and 1 mg of magnesium stearate, tablets are produced by a conventional method.

Preparation Example 6

| | |
|---|---|
| (1) Compound produced in Example 10 (Compound 6) | 5 g |
| (2) Lactose/crystalline cellulose (particles) | 330 g |
| (3) D-mannitol | 29 g |
| (4) Low-substitutional hydroxypropyl cellulose | 20 g |
| (5) Talc | 25 g |
| (6) Hydroxypropyl cellulose | 50 g |
| (7) Aspartame | 3 g |
| (8) Dipotassium glycyrrhizinate | 3 g |
| (9) Hydroxypropylmethyl cellulose 2910 | 30 g |
| (10) Titanium oxide | 3.5 g |
| (11) Yellow iron sesquioxide | 0.5 g |
| (12) Light silicic anhydride | 1 g |

Components (1), (3), (4), (5), (6), (7) and (8) are suspended or dissolved in purified water and coated on the core particles (2) to yield base fine subtilae, which are then further coated with components (9) through (11) to yield coated fine subtilae, which are then mixed with component (12) to yield 500 g of 1% fine subtilae of the compound obtained in Example 10 (compound 6). These subtilae are divided to 500 mg folded subtilae.

Industrial Applicability

The compound of the present invention possesses excellent gonadotropin-releasing hormone antagonizing activity. It is also good in oral absorbability and excellent in stability and pharmacokinetics. With low toxicity, it is also excellent in safety;

The compound of the present invention can therefore be used as a prophylactic or therapeutic agent for hormone-dependent diseases etc. Specifically, it is effective as a prophylactic or therapeutic agent for sex hormone-dependent cancers (e.g., prostatic cancer, uterine cancer, breast cancer, pituitary tumor), prostatic hypertrophy, hysteromyoma, endometriosis, precocious puberty, amenorrhea syndrome, multilocular ovary syndrome, pimples etc, or as a pregnancy regulator (e.g., contraceptive), infertility remedy or menstruation regulator. It is also effective as an animal estrous regulator, food meat quality improving agent or animal growth regulator in the field of animal husbandry, and as a fish spawning promoter in the field of fishery.

What is claimed is:
1. A compound of the formula (I):

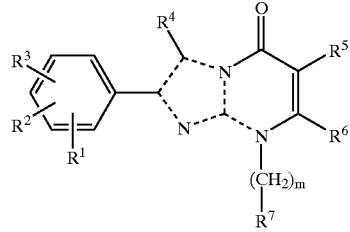

or a salt thereof, wherein in formula I:
m represents an integer from 0 to 3;
each dotted line represents a single bond or a double bond and $R^1$, $R^2$ and $R^3$ each is
(1) hydrogen,
(2) a hydrocarbon group which may be substituted,
(3) an acyl group which may be substituted,
(4) a heterocyclic group having a bond in a carbon atom thereof which may be substituted, (5) a group of the formula: —COOR$^{21}$ wherein R$^{21}$ is hydrogen, a hydrocarbon group which may be substituted or a heterocyclic group which may be substituted, (6) a group of the formula: —CO—NR$^{15}$R$^{16}$ wherein R$^{15}$ is hydrogen, a hydrocarbon group which may be substituted or a C$_{1-10}$ alkoxy group; and R$^{16}$ is hydrogen or a hydrocarbon group which may be substituted; or R$^{15}$ and R$^{16}$ form, taken together with the adjacent nitrogen atom, a cyclic amino group which may be substituted, (7) a cyano group, (8) a nitro group, (9) a group of the formula: —NR$^{8}$R$^{9}$ wherein R$^{8}$ is (i) hydrogen, (ii) a hydrocarbon group which may be substituted, (iii) an acyl group which may be substituted, (iv) a group of the formula: —O—R$^{13}$ wherein R$^{13}$ is hydrogen, a C$_{1-10}$ hydrocarbon group which may be substituted, a C$_{1-20}$ acyl group which may be substituted, a C$_{1-20}$ allkylsulfonyl group which may be substituted, a C$_{6-14}$ arylsulfonyl group which may be substituted or a heterocyclic group which may be substituted, (v) a heterocyclic group which may be substituted or (vi) a group of the formula: —S(O)t-R$^{12}$ wherein t is an integer from 0 to 2, and R$^{12}$ is hydrogen or a C$_{1-10}$ hydrocarbon group which may be substituted;

R$^{9}$ is hydrogen, a hydrocarbon group which may be substituted or an acyl group which may be substituted; or R$^{8}$ and R$^{9}$ form, taken together with the adjacent nitrogen atom, a cyclic amino group which may be substituted,

(10) a group of the formula: —O—R$^{13}$ wherein R$^{13}$ is as defined above, or

(11) a group of the formula: —S(O)t-R$^{14}$ wherein t is an integer from 0 to 2, and R$^{14}$ is hydrogen, a hydrocarbon group which may be substituted or a heterocyclic group which may be substituted;

R$^{4}$ is (1) a hydrocarbon group which may be substituted, (2) an acyl group which may be substituted, (3) a heterocyclic group having a bond in a carbon atom thereof which may be substituted, (4) a group of the formula: —COOR$^{21}$ wherein R$^{21}$ is as defined above, (5) a group of the formula: —CO—NR$^{15}$R$^{16}$ wherein each symbol is as defined above, or (6) a cyano group;

R$^{5}$ is (1) hydrogen, (2) halogen, (3) a hydrocarbon group which may be substituted, (4) an acyl group which may be substituted, (5) a heterocyclic group having a bond in a carbon atom thereof which may be substituted, (6) a group of the formula: —COOR$^{21}$ wherein R$^{21}$ is as defined above, (7) a group of the formula: —CO—NR$^{15}$R$^{16}$ wherein each symbol is as defined above, (8) a cyano group, or (9) a group of the formula: —O—R$^{13}$ wherein R$^{13}$ is as defined above;

R$^{6}$ is (1) hydrogen, (2) a hydrocarbon group which may be substituted, (3) an acyl group which may be substituted, (4) a heterocyclic group having a bond in a carbon atom thereof which may be substituted, (5) a group of the formula: —COOR$^{21}$ wherein R$^{21}$ is as defined above, (6) a group of the formula: —CO—NR$^{15}$R$^{16}$ wherein each symbol is as defined above, or (7) a cyano group;

R$^{7}$ is (i) a C$_{6-10}$ aryl or C$_{3-7}$ cycloalkyl group, each of which may be substituted by 1 to 6 substituents selected from the group consisting of (1) C$_{1-15}$ alkyl which may be substituted by 1 to 3 halogen, (2) C$_{3-10}$ cycloalkyl, (3) C$_{2-10}$ alkenyl, (4) C$_{2-10}$ alkynyl, (5) C$_{3-10}$ cycloalkenyl, (6) C$_{6-10}$ aryl, (7) C$_{7-20}$ aralkyl, (8) nitro, (9) hydroxy, (10) mercapto, (11) oxo, (12) thioxo, (13) cyano, (14) carbamoyl, (15) carboxyl, (16) C$_{1-6}$ alkoxy-carbonyl, (17) sulfo, (18) halogen, (19) C$_{1-6}$ alkoxy, (20) C$_{6-10}$ aryloxy, (21) C$_{1-6}$ alkanoyloxy, (22) C$_{1-6}$ alkylthio, (23) C$_{6-10}$ arylthio, (24) C$_{1-6}$ alkylsulfinyl, (25) C$_{6-10}$ arylsulfinyl, (26) C$_{1-6}$ alkylsulfonyl, (27) C$_{6-10}$ arylsulfonyl, (28) amino, (29) C$_{1-6}$ alkanoylamino, (30) mono- or di-C$_{1-4}$ alkylamino, (31) C$_{3-8}$ cycloalkylamino, (32) C$_{6-10}$ arylamino, (33) C$_{1-6}$ alkanoyl, (34) C$_{6-10}$ aryl-carbonyl and (35) 5- to 6-membered heterocyclic group, or (ii) a heterocyclic group which may be substituted, in which "hydrocarbon group" is a C$_{1-20}$ hydrocarbon group selected from C$_{1-15}$ alkyl, C$_{3-10}$ cycloalkyl, C$_{2-10}$ alkenyl, C$_{2-10}$ alkynyl, C$_{3-10}$ cycloalkenyl, C$_{6-14}$ aryl and C$_{7-20}$ aralkyl;

"C$_{1-10}$ hydrocarbon group" is a C$_{1-10}$ alkyl, C$_{3-10}$ cycloalkyl, C$_{2-10}$ alkenyl, C$_{2-10}$ alkynyl, C$_{3-10}$ cycloalkenyl, C$_{6-10}$ aryl or phenyl-C$_{1-4}$ alkyl group;

"acyl group" and "C$_{1-20}$ acyl group" each is formyl, C$_{1\ 6}$ alkyl-carbonyl, C$_{1-6}$ alkoxy-carbonyl, C$_{6-14}$ aryl-carbonyl, C$_{6-14}$ aryloxy-carbonyl, C$_{6-14}$ aryl-C$_{1-6}$ alkyl-carbonyl, C$_{6-14}$ aryl-C$_{1-6}$ alkoxy-carbonyl, C$_{2-4}$ alkenyl-carbonyl, C$_{3-6}$ cycloalkyl-carbonyl or tricyclic bridged C$_{9-10}$ hydrocarbon-carbonyl;

"heterocyclic group" is (1) a 5- to 8-membered heterocyclic group containing 1 to 4 hetero atoms selected from oxygen atoms, sulfur atoms, nitrogen atoms in addition to carbon atoms, (2) a bi- or tri-cyclic condensed heterocyclic group resulting from condensation of 2 or 3 of the above (1) heterocyclic group, whether identical or not, or (3) a bi- or tri-cyclic condensed heterocyclic group resulting from condensation of the above (1) heterocyclic group and 1 or 2 benzene rings;

"cyclic amino group" is a 5- to 7-membered cyclic amino group optionally containing 1 to 3 hetero atoms selected from oxygen atoms, sulfur atoms, nitrogen atoms in addition to carbon atoms and a nitrogen atom;

"substituent(s)" for the "hydrocarbon group which may be substituted," the "C$_{1-10}$ hydrocarbon group which may be substituted," the "acyl group which may be substituted," the "C$_{1-20}$ acyl group which may be substituted," the "C$_{1-20}$ alkylsulfonyl group which may be substituted" or the "C$_{6-14}$ arylsulfonyl group which may be substituted" is selected from 1 to 6 of (1) halogen, (2) nitro, (3) nitroso, (4)

cyano, (5) (i) $C_{1-6}$ alkyl which may be substituted by 1 to 3 substituents selected from the group consisting of hydroxy, $C_{1-6}$ alkoxy, $C_{1-3}$ alkoxy-$C_{1-3}$ alkoxy, $C_{1-3}$ alkylthio, hydroxy-$C_{1-3}$ alkoxy, $C_{1-6}$ alkyl-carbonyl, carboxy, carbamoyl, $C_{1-6}$ alkyl-carbamoyl, 5- to 8-membered heterocyclic group and halogen, (ii) $C_{1-4}$ alkanoyl or $C_{2-4}$ alkenoyl, (iii) $C_{6-14}$ aryl-$C_{1-6}$ alkyl which may be substituted by 1 to 3 substituents selected from the group consisting of halogen, $C_{1-3}$ alkoxy and $C_{1-4}$ alkyl, (iv) $C_{6-14}$ aryl which may be substituted by 1 to 3 halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkylamino, (ix) $C_{2-6}$ alkenylamino, (x) $C_{1-3}$ alkoxy-carbonyl, (xi) formyl or $C_{1-6}$ alkyl-carbonyl, or (xii) hydroxy which may be substituted by $C_{3-6}$ cycloalkyloxy-carbonyl, (6) a group of the formula: —S(O)t-$R^{17}$ wherein t is an integer from 0 to 2, and $R^{17}$ is (i) hydrogen or (ii) a $C_{1-6}$ alkyl, $C_{6-14}$ aryl or $C_{7-20}$ aralkyl group which may be substituted by 1 to 3 substituents selected from the group consisting of halogen, nitro, cyano, hydroxy, oxo, thioxo, carboxy, cyano-$C_{6-14}$ aryl and halogeno-$C_{6-14}$ aryl, (7) a group of the formula: —$NR^{18}R^{19}$ wherein $R^{18}$ and $R^{19}$ each is hydrogen, $C_{1-6}$ alkyl, $C_{1-6}$ alkylamino-$C_{1-6}$ alkyl, $C_{1-6}$ alkoxy, $C_{2-6}$ alkenyl, $C_{3-7}$ cycloalkyl, phenyl, phenyl-$C_{1-6}$ alkyl, $C_{1-6}$ alkanoyl, $C_{3-6}$ alkenoyl, $C_{4-7}$ cycloalkyl-carbonyl, phenyl-$C_{1-6}$ alkyl-carbonyl, $C_{1-6}$ alkoxy-carbonyl, phenyl-$C_{1-6}$ alkoxy-carbonyl or 5- to 8-membered heterocyclic group, (8) a group of the formula: —CO—$R^{20}$ wherein $R^{20}$ is (i) hydrogen, (ii) hydroxy, (iii) $C_{1-10}$ alkyl or (iv) $C_{1-6}$ alkoxy which may be substituted by $C_{6-14}$ aryl which may be substituted by 1 to 3 substituents selected from the group consisting of halogen and nitro, (v) $C_{3-6}$ cycloalkyl, (vi) $C_{6-14}$ aryl, (vii) C6-14 aryloxy, (viii) $C_{7-20}$ aralkyl, (ix) a group of the formula: —$NR^{10}R^{11}$ wherein $R^{10}$ is hydrogen, a $C_{1-10}$ hydrocarbon group which may be substituted, a $C_{1-20}$ acyl group which may be substituted, a group of the formula: —O—$R^{13}$ wherein $R^{13}$ is as defined above, a heterocyclic group which may be substituted or a group of the formula: —S(O)t-$R^{12}$ wherein each symbol is as defined above; and $R^{11}$ is hydrogen or a $C_{1-10}$ hydrocarbon group; or $R^{10}$ and $R^{11}$ form, taken together with the adjacent nitrogen atom, a cyclic amino group which may be substituted, or (x) 5- to 8-membered heterocyclic group, (9) 5- to 8-membered heterocyclic group which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (10) sulfo, (11) $C_{6-14}$ aryl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (12) $C_{3-7}$ cycloalkyl which may be substituted by 1 to 3 substituents selected from the group consisting of hydroxy, amino, mono- or di-$C_{1-4}$ alkylamino, $C_{1-4}$ alkoxy, halogen, nitro and $C_{1-6}$ alkyl, (13) $C_{1-6}$ alkylenedioxy, (14) oxo, (15) thioxo, (16) $C_{2-4}$ alkynyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (17) $C_{3-10}$ cycloalkyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (18) $C_{2-10}$ alkenyl which may be substituted by 1 to 3 substituents selected form the group consisting of hydroxy, amino, mono- or di-$C_{1-4}$ alkylamino, $C_{1-4}$ alkoxy, halogen, nitro and $C_{1-6}$ alkyl, (19) $C_{7-20}$ aralkyl which may be substituted by 1 to 3 substituents selected from the group consisting of hydroxy, amino, mono- or di-$C_{1-4}$ alkylamino, $C_{1-4}$ alkoxy, halogen, nitro and $C_{1-6}$ alkyl, (20) amidino and (21) azido;

"substituent(s)" for the "heterocyclic group which may be substituted" or the "heterocyclic group having a bond in a carbon atom thereof which may be substituted" is selected from 1 to 6 of (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{6-10}$ aryl-$C_{1-5}$ alkyl, (7) $C_{6-14}$ aryl, (8) $C_{1-6}$ alkoxy, (9) $C_{6-14}$ aryloxy, (10) $C_{1-6}$ alkanoyl, (11) $C_{6-14}$ aryl-carbonyl, (12) $C_{1-6}$ alkanoyloxy, (13) $C_{6-14}$ aryl-carbonyloxy, (14) carboxyl, (15) $C_{1-6}$ alkoxy-carbonyl, (16) carbamoyl, (17) N-mono-$C_{1-4}$ alkylcarbamoyl, (18) N,N-di-$C_{1-4}$ alkylcarbamoyl, (19) 3- to 6-membered cyclic aminocarbonyl, (20) halogen, (21) mono-, di- or tri-halogeno-$C_{1-4}$ alkyl, (22) oxo, (23) amidino, (24) imino, (25) amino, (26) mono- or di-$C_{1-4}$ alkylamino, (27) 3- to 6-membered cyclic amino, (28) $C_{1-6}$ alkanoylamino, (29) benzamido, (30) carbamoylamino, (31) N—$C_{1-4}$ alkylcarbamoylamino, (32) N,N-di-$C_{1-4}$ alkylcarbamoylamino, (33) $C_{1-3}$ alkylenedioxy, (34) —$B(OH)_2$, (35) hydroxy, (36) epoxy, (37) nitro, (38) cyano, (39) mercapto, (40) sulfo, (41) sulfino, (42) phosphono, (43) sulfamoyl, (44) $C_{16}$ alkylsulfamoyl, (45) di-$C_{1-6}$ alkylsulfamoyl, (46) $C_{1-6}$ alkylthio, (47) phenylthio, (48) $C_{1-6}$ alkylsulfinyl, (49) phenylsulfinyl, (50) $C_{1-6}$ alkylsulfonyl and (51) phenylsulfonyl; and "substituent(s)" for the "cyclic amino group which may be substituted" is selected from 1 to 3 of $C_{1-6}$ alkyl, $C_{6-14}$ aryl, phenyl-$C_{1-4}$ alkyl, benzhydryl, $C_{1-6}$ alkyl-carbonyl, $C_{6-14}$ aryl-carbonyl and $C_{1-6}$ alkoxy-carbonyl.

2. The compound of claim 1 or a salt thereof, wherein m is 1.

3. The compound of claim 1 or a salt thereof, wherein $R^1$ is (1) a $C_{1-15}$ alkyl group which may be substituted, (2) a $C_{3-10}$ cycloalkyl group which may be substituted, (3) a $C_{2-10}$ alkenyl group which may be substituted, (4) a $C_{2-10}$ alkynyl group which may be substituted, (5) a $C_{3-10}$ cycloalkenyl group which may be substituted, (6) a $C_{6-14}$ aryl group which may be substituted, (7) a $C_{7-20}$ aralkyl group which may be substituted, (8) a $C_{1-20}$ acyl group which may be substituted, (9) a nitro group, (10)

a group of the formula: —NR$^{10}$R$^{11}$ wherein R$^{10}$ is hydrogen, a C$_{1-10}$ hydrocarbon group which may be substituted, a C$_{1-20}$ acyl group which may be substituted, a hydroxy group which may be substituted, a heterocyclic group which may be substituted or a group of the formula: —S(O)t-R$^{12}$ wherein t is an integer from 0 to 2, and R$^{12}$ is hydrogen or a C$_{1-10}$ hydrocarbon group which may be substituted; R$^{11}$ is hydrogen or a C$_{1-10}$ hydrocarbon group; or wherein R$^{10}$ and R$^{11}$ form, taken together with the adjacent nitrogen atom, a cyclic amino group which may be substituted, or (11) a group of the formula: —O—R$^{13}$ wherein R$^{13}$ is hydrogen, a C$_{1-10}$ hydrocarbon group which may be substituted, a C$_{1-20}$ acyl group which may be substituted, a C$_{1-20}$ alkylsulfonyl group which may be substituted, a C$_{6-14}$ arylsulfonyl group which may be substituted, or a heterocyclic group which may be substituted; and R$^2$ and R$^3$ each is hydrogen.

4. The compound of claim 1 or a salt thereof, wherein R$^2$ and R$^3$ each is hydrogen.

5. The compound of claim 4 or a salt thereof, wherein R$^1$ is in a para-position.

6. The compound of claim 1 or a salt thereof, wherein R$^1$ is (1) an amino group which may be substituted by (i) carbamoyl which may be substituted by C$_{1-6}$ alkyl or C$_{1-6}$ alkoxy, or (ii) C$_{1-6}$ alkyl-carbonyl, or (2) a C$_{1-6}$ alkoxy group which may be substituted by C$_{3-6}$ cycloalkyl.

7. The compound of claim 1 or a salt thereof, wherein R$^4$ is a C$_{1-15}$ alkyl group which may be substituted, a C$_{3-10}$ cycloalkyl group which may be substituted, a C$_{2-10}$ alkenyl group which may be substituted, a C$_{2-10}$ alkynyl group which may be substituted, a C$_{3-10}$ cycloalkenyl group which may be substituted, a C$_{6-14}$ aryl group which may be substituted, or a C$_{7-20}$ aralkyl group which may be substituted.

8. The compound of claim 1 or a salt thereof, wherein R$^4$ is a C$_{1-6}$ alkyl group which may be substituted.

9. The compound of claim 1 or a salt thereof, wherein R$^4$ is a C$_{1-6}$ alkyl group which may be substituted by halogen, hydroxyl which may be substituted or amino which may be substituted.

10. The compound of claim 1 or a salt thereof, wherein R$^4$ is a group of the formula: —(CH$_2$)n—NR$^{10}$R$^{11}$ wherein n is an integer from 1 to 3; R$^{10}$ is hydrogen, a C$_{1-10}$ hydrocarbon group which may be substituted, a C$_{1-20}$ acyl group which may be substituted, a hydroxy group which may be substituted, a heterocyclic group which may be substituted, or a group of the formula: —S(O)t-R$^{12}$ wherein t is an integer from 0 to 2, and R$^{12}$ is hydrogen or a C$_{1-10}$ hydrocarbon group which may be substituted; and R$^{11}$ is hydrogen or a C$_{1-10}$ hydrocarbon group; or R$^{10}$ and R$^{11}$ form, taken together with the adjacent nitrogen atom, a cyclic amino group which may be substituted.

11. The compound of claim 1 or a salt thereof, wherein R$^4$ is a N—C$_{1-6}$ alkyl-N-benzylaminomethyl group.

12. The compound of claim 1 or a salt thereof, wherein R$^5$ is hydrogen, halogen, a C$_{1-15}$ alkyl group which may be substituted, a C$_{3-10}$ cycloalkyl group which may be substituted, a C$_{2-10}$ alkenyl group which may be substituted, a C$_{2-10}$ alkynyl group which may be substituted, a C$_{3-10}$ cycloalkenyl group which may be substituted, a C$_{6-14}$ aryl group which may be substituted, a C$_{7-20}$ aralkyl group which may be substituted, a C$_{1-20}$ acyl group which may be substituted, a carboxy group which may be esterified or amidated, or a group of the formula: —O—R$^{13}$ wherein R$^{13}$ is hydrogen or a C$_{1-15}$ alkyl group which may be substituted, a C$_{3-10}$ cycloalkyl group which may be substituted, a C$_{2-10}$ alkenyl group which may be substituted, a C$_{2-10}$ alkynyl group which may be substituted, a C$_{3-10}$ cycloalkenyl group which may be substituted, a C$_{6-14}$ aryl group which may be substituted, a C$_{7-20}$ aralkyl group which may be substituted, a C$_{1-20}$ acyl group which may be substituted, a C$_{1-20}$ alkylsulfonyl group which may be substituted, a C$_{6-14}$ arylsulfonyl group which may be substituted or a heterocyclic group which may be substituted.

13. The compound of claim 1 or a salt thereof, wherein R$^5$ is (1) a C$_{1-6}$ alkoxy-carbonyl group, (2) a C$_{6-10}$ aryl group which may be substituted by halogen or C$_{1-6}$ alkoxy, or (3) a phenyl-C$_{1-3}$ alkyl group.

14. The compound of claim 1 or a salt thereof, wherein R$^6$ is hydrogen, a C$_{1-15}$ alkyl group which may be substituted, a C$_{3-10}$ cycloalkyl group which may be substituted, a C$_{2-10}$ alkenyl group which may be substituted, a C$_{2-10}$ alkynyl group which may be substituted, a C$_{3-10}$ cycloalkenyl group which may be substituted, a C$_{6-14}$ aryl group which may be substituted or a C$_{7-20}$ aralkyl group which may be substituted.

15. The compound of claim 1 or a salt thereof, wherein R$^6$ is hydrogen or a C$_{1-6}$ alkyl group.

16. The compound of claim 1 or a salt thereof, wherein R$^7$ is a C$_{6-14}$ aryl group which may be substituted.

17. The compound of claim 1 or a salt thereof, wherein R$^7$ is a phenyl group which may be substituted by halogen(s).

18. The compound of claim 1 or a salt thereof, wherein m represents an integer from 0 to 3;

R$^1$, R$^2$ and R$^3$ each represents (i) hydrogen or (ii) a group bound via a carbon atom, a nitrogen atom, an oxygen atom or a sulfur atom;

R$^4$ represents a group bound via a carbon atom;

R$^5$ represents hydrogen or a group bound via a carbon atom or an oxygen atom;

R$^6$ represents hydrogen or a group bound via a carbon atom;

R$^7$ represents a homocyclic group which may be substituted or a heterocyclic group which may be substituted; and each dotted line represents a single bond or a double bond.

19. The compound of claim 1 or a salt thereof, wherein the compound is represented by the formula:

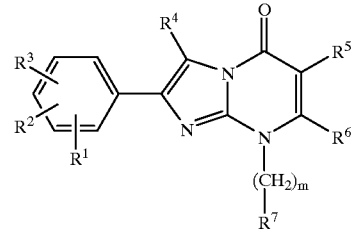

wherein each symbol is as defined in claim 1, or a salt thereof.

20. The compound of claim 19 or a salt thereof, wherein R$^4$ is a group of the formula: —(CH$_2$)n—NR$^{10}$R$^{11}$ wherein n is an integer from 1 to 3; R$^{10}$ is hydrogen, a C$_{1-10}$ hydrocarbon group which may be substituted, a C$_{1-20}$ acyl group which may be substituted, a hydroxy group which may be substituted, a heterocyclic group which may be substituted, or a group of the formula: —S(O)t-R$^{12}$ wherein t is an integer from 0 to 2, and R$^{12}$ is hydrogen or a C$_{1-10}$ hydrocarbon group which may be substituted; and R$^{11}$ is hydrogen, a C$_{1-10}$ hydrocarbon group or a C$_{1-20}$ acyl group which may be substituted; or wherein $R^{10}$ and $R^{11}$ form, taken together with the adjacent nitrogen atom, a cyclic amino group which may be substituted.

21. The compound of claim 1, wherein the compound is represented by the formula:

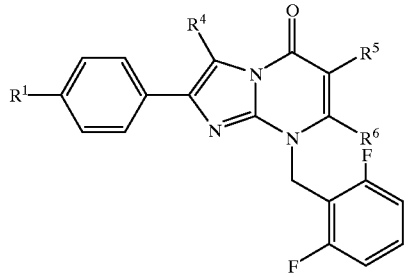

wherein each symbol is as defined in claim 1, or a salt thereof.

22. The compound of claim 21 or a salt thereof, wherein
$R^1$ is (1) an amino group which may be substituted by (i) carbamoyl which may be substituted by $C_{1-6}$ alkyl or $C_{1-6}$ alkoxy, or (ii) $C_{1-6}$ alkyl-carbonyl, or (2) a $C_{1-6}$ alkoxy group which may be substituted by $C_{3-6}$ cycloalkyl;
$R^4$ is a N—$C_{1-6}$ alkyl-N-benzylaminomethyl group;
$R^5$ is (1) a $C_{1-6}$ alkoxy-carbonyl group, (2) a $C_{6-10}$ aryl group which may be substituted by halogen or $C_{1-6}$ alkoxy, or (3) a phenyl-$C_{1-3}$ alkyl group; and
$R^6$ is hydrogen.

23. The compound of claim 21 or a salt thereof, wherein $R^1$ is
  (1) a nitro group,
  (2) an amino group which may be substituted by 1 or 2 substituents selected from the group consisting of (i) $C_{1-6}$ alkyl which may be substituted by hydroxy, (ii) $C_{1-6}$ alkyl-carbonyl which may be substituted by hydroxy, halogen or thienyl, (iii) $C_{6-10}$ aryl-carbonyl which may be substituted by $C_{1-6}$ alkyl, $C_{1-6}$ alkoxy or halogen, (iv) $C_{3-6}$ cycloalkyl-carbonyl, (v) $C_{2-4}$ alkenyl-carbonyl, (vi) $C_{1-6}$ alkoxy-carbonyl, (vii) $C_{1-6}$ alkylamino-carbonyl, (viii) $C_{1-6}$ alkoxyamino-carbonyl, (ix) phenylaminocarbonyl, (x) an isoxazolylcarbonyl, thienylcarbonyl, thiazolylcarbonyl, pyrazolylcarbonyl or furylcarbonyl group which may be substituted by 1 or 2 substituents selected from the group consisting of $C_{1-6}$ alkyl, nitro and $C_{1-6}$ alkoxy, (xi) pyridylcarbonyl, (xii) $C_{1-6}$ alkylsulfonyl, (xiii) thienylsulfonyl and (xiv) phenylsulfonyl which may be substituted by $C_{1-6}$ alkyl,
  (3) a pyrrolyl group or
  (4) a hydroxy group which may be substituted by $C_{1-6}$ alkyl, $C_{3-6}$ cycloalkyl-$C_{1-3}$ alkyl or $C_{1-6}$ alkyl-carbonyl;
$R^4$ is a $C_{1-6}$ alkyl group which may be substituted by 1 or 2 substituents selected from the group consisting of (1) halogen, (2) hydroxy and (3) amino which may be substituted by 1 or 2 substituents selected from the group consisting of $C_{1-6}$ alkyl, phenyl-$C_{1-3}$ alkyl and di-$C_{1-6}$ alkylamino-$C_{1-3}$ alkyl;
$R^5$ is (1) halogen, (2) a phenyl group which may be substituted by halogen or $C_{1-6}$ alkyl, or (3) a carbonyl group substituted by (i) $C_{1-6}$ alkyl, (ii) amino substituted by $C_{1-6}$ alkyl and $C_{1-6}$ alkoxy or (iii) $C_{1-6}$ alkoxy; and
$R^6$ is hydrogen or a $C_{1-3}$ alkyl group.

24. A process for producing a compound of claim 19 or a salt thereof, which comprises reacting a compound of the formula (iv):

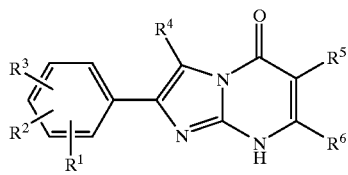

wherein each symbol is as defined in claim 19, or a salt thereof, with a compound of the formula: $X^2$—$(CH_2)m$—$R^7$ wherein $X^2$ is a leaving group; and the other symbols are as defined in claim 19, or a salt thereof.

25. A pharmaceutical composition comprising a compound of claim 1 or a salt thereof in a pharmaceutically acceptable carrier.

26. A method for antagonizing gonadotropin-releasing hormone in a mammal in need thereof which comprises administering to said mammal an effective amount of the compound of claim 1 or a salt thereof.

27. A method for treating prostatic cancer, uterine cancer or breast cancer, wherein the method comprises administering to a mammal an effective amount of the compound of claim 1 or a salt thereof.

28. A method for treating prostatic hypertrophy, endometriosis, hysteromyoma or precocious puberty, wherein the method comprises administering to a mammal an effective amount of the compound of claim 1 or a salt thereof.

29. A method for regulating pregnancy, wherein the method comprises administering to a mammal an effective amount of the compound of claim 1 or a salt thereof.

30. A method for regulating menstruation cycle, wherein the method comprises administering to a mammal an effective amount of the compound of claim 1 or a salt thereof.

31. A method for treating prostatic cancer, uterine cancer, breast cancer, pituitary tumor, prostatic hypertrophy, hysteromyoma, endometriosis, precocious puberty, amenorrhea, premenstrual syndrome, multilocular ovary syndrome or pimples, wherein the method comprises administering to a mammal an effective amount of the compound of claim 1 or the salt thereof.

* * * * *